United States Patent [19]

Schieven

[11] Patent Number: 5,877,210
[45] Date of Patent: Mar. 2, 1999

[54] PHOSPHOTYROSINE PHOSPHATASE INHIBITORS OR PHOSPHOTYROSINE KINASE ACTIVATORS FOR CONTROLLING CELLULAR PROLIFERATION

[75] Inventor: Gary L. Schieven, Seattle, Wash.

[73] Assignee: Bristol-Myers Squibb Company, Princeton, N.J.

[21] Appl. No.: 465,813

[22] Filed: Jun. 5, 1995

Related U.S. Application Data

[63] Continuation-in-part of PCT/US95/01234, Jan. 30, 1995, which is a continuation-in-part of Ser. No. 189,330, Jan. 31, 1994, Pat. No. 5,565,491.

[51] Int. Cl.$^6$ .................. A01N 55/02; A61K 39/395; C07F 53/00
[52] U.S. Cl. .................. 514/492; 556/1; 556/42; 556/44; 424/178.1; 424/179.1; 424/181.1; 435/184; 435/244
[58] Field of Search .................. 424/178.1, 179.1, 424/181.1; 435/184, 244; 514/492, 499; 556/1, 42, 44

[56] References Cited

U.S. PATENT DOCUMENTS

| | | | |
|---|---|---|---|
| 5,023,358 | 6/1991 | Lazaro et al. | 556/42 |
| 5,175,001 | 12/1992 | Lazaro et al. | 424/451 |

FOREIGN PATENT DOCUMENTS

WO 93/06811   4/1993   WIPO .

OTHER PUBLICATIONS

G.J.V. Nossal, "Cellular Mechanisms of Immunologic Tolerance", *Annu. Rev. Immunol.* 1:33–62 (1983).

F.M. Uckun & J.A. Ledbetter, "Immunobiologic Differences Between Normal and Leukemic Human Cell Precursors", *Proc.Natl.Acad.Sci.USA* 85: 8603–8607 (1988).

T.R. Burke et al., "Preparation of Fluoro–and Hydroxy–4–(Phosphonomethyl)–D,L–Phenylalanine Suitably Protected for Solid–Phase Synthesis of Peptides Containing Hydrolytically Stable Analogues of O–Phosphotyrosine", *J.Org.Chem.* 48: 1336–1340 (1993).

D.B.A. de Bont et al., "Solid–Phase Synthesis of O–Phosphorothioylserine–and Threonine–Containing Peptides as Well as of O–Phosphoserine–and–Theronine–Containing Peptides", *J. Org. Chem.* 58: 1309–1317 (1993).

K. Guan et al., "A Tyr/Ser Protein Phosphatase Encoded by Vaccinia Virus", *Nature* 350: 359–362 (1991).

D. Dailey et al., "Novel Yeast Protein Kinae (YPK1 Gene Product) Is a 40–Kilodalton Phosphotyrosyl Protein Associated with Protein–Tyrosine Kinase Activity", *Mol. Cell. Biol.* 10: 6244–6256 (1990).

M. Imoto et al., "Dephostatin, a Novel Protein Tyrosine Phosphatase Inhibitor Produced by *Streptomyces*. I. Taxonomy, Isolation, and Characterization", *J. Antibiotics* 46: 1342–1346 (1993).

J. H. McNeill et al., "Bis(maltolato) oxovanadium (IV) Is a Potent Insulin Mimic", *J.Med.Chem.* 35: 1489–1491 (1992).

R.R. Bartlett et al., Leflunomide (HWA 486), a Novel Immunomodulating Compound for the Treatment of Autoimmune Disorders and Reactions Leading to Transplantation Rejection, *Agents & Actions* 32: 10–21 (1991).

J.K. Myers & T.S. Widlanski, Mechanism–Based Inactivation of Prostatic Acid Phosphatase, *Science* 262: 1451–1453 (1993).

L.B. Justement et al., "Regulation of B Cell Antigen Receptor Signal Transduction and Phosphorylation of CD45", *Science* 252: 1839–1842, (1991).

M.R. Gold et al, "Stimulation of Protein Tyrosine Phosphorylation by the B–Lymphocyte Antigen Receptor", *Nature* 345: 810–843 (1990).

M.C. Cam et al., "In Vivo Antidiabetic Actions of Naglivan, An Organic Vanadyl Compound in Streptozotocin–Induced Diabetes", *Diabetes Res. & Clin. Pract.* 20: 111–121 (1993).

A.L. Burkhardt et al., "Anti–Immunoglobulin Stimulation of B Lymphocytes Activates src–Related Protein–Tyrosine Kinases," *Proc. Natl. Acad. Sci. USA* 88: 7410–7414 (1991).

F.M. Uckun et al., "Tyrosine Phosphorylation Is a Mandatory Proximal Step in Radiation–Induced Activation of the Protein Kinase C Signaling Pathway in Human B–Lymphocyte Precursors," *Proc. Natl. Acad. Sci. USA* 90: 252–256 (1993).

C.P. Stewart & A.L. Prote, "Electron Paramagnetic Resonance Spectra of Some Oxovanadium (IV) Chelates," *J. Chem. Soc. Dalton Trans.* 1661–1666 (1972).

(List continued on next page.)

*Primary Examiner*—Ponnathapura Achutamurthy
*Assistant Examiner*—P. Ponnaluri
*Attorney, Agent, or Firm*—Merchant, Gould, Smith, Edell, Welter & Schmidt

[57] ABSTRACT

A method of inhibiting the proliferation of B cells by using inhibitors of phosphotyrosine phosphatase can be used to regulate the immune response and to treat diseases such as leukemias or lymphomas marked by malignant proliferation of B cells or T cells. Antitumor activity is seen in vivo against tumors and against tumor cell lines. The use of such inhibitors can be combined with radiation, which produces a synergistic effect. Several types of inhibitors can be used, including: (1) compounds comprising a metal coordinate-covalently bound to an organic moiety that can form a five- or six-membered ring, in which the metal is preferably vanadium (IV); (2) compounds in which vanadium (IV) is coordinate-covalently bound to an organic moiety such as a hydroxamate, α-hydroxypyridinone, α-hydroxypyrone, α-amino acid, hydroxycarbonyl, or thiohydroxamate; (3) coordinate-covalent complexes of vanadyl and cysteine or a derivative thereof; (4) nonhydrolyzable phosphotyrosine phosphatase analogues; (5) dephostatin; (6) 4-(fluoromethyl)phenyl phosphate and esterified derivatives; and (7) coordinate-covalent metal-organic compounds containing at least one oxo or peroxo ligand bound to the metal, in which the metal is preferably vanadium (V), molybdenum (VI), or tungsten (VI). Methods of stimulating signaling in T cells and conjugates of a modulator of phosphotyrosine metabolism with a specific binding partner for a B cell surface antigen are also disclosed.

26 Claims, 36 Drawing Sheets

OTHER PUBLICATIONS

X.-R. Yao & D.W. Scott, "Expression of Protein Tyrosine Kinases in the Ig Complex of Anti–μ–Sensitive and Anti–μ–Resistant B–Cell Lymphomas: Role of the p55$^{blk}$ Kinase in Signalling Growth Arrest and Apoptosis," *Immunol. Rev.* 132: 163–186 (1993).

X.-R. Yao & D.W. Scott, "Antisense Oligodeoxynucleotidase to the blk Tyrosine Kinase Prevent Anti–μ–Chain–Mediated Growth Inhibition and Apoptosis in a B–Cell Lymphoma," *Proc. Natl. Acad. Sci. USA* 90: 7946–7950 (1993).

F.M. Uckun et al., "Ionizing Radiation Stimulates Unidentified Tyrosine–Specific Protein Kinases in Human B–Lymphocyte Precursors, Triggering Apoptosis and Clonogenic Cell Death," *Proc. Natl. Acad. Sci. USA* 89: 9005–9009 (1992).

P.J.L. Lane et al., "The Role of Tyrosine Phosphorylation in Signal Transduction Through Surface Ig in Human B Cells," *J. Immunol.* 146: 715–722 (1991).

F.M. Uckun et al., "Use of Novel Colony Assay to Evaluate the Cytotoxicity of an Immunotoxin Containing Pokeweed Antiviral Protein Against Blast Progenitor Cells Freshly Obtained from Patients with Common B–Lineage Acute Lymphoblastic Leukemia," *J. Exp. Med.* 163; 347–368 (1986).

M.A. Campbell & B.M. Sefton, "Protein Tyrosine Phosphorylation is Induced in Murine B Lymphocytes in Response to Stimulation with Anti–Immunoglobulin," *EMBO J.* 9: 2125–2131 (1990).

Abstract, Meeting of the Oxygen Society, Charleston, South Carolina, on Nov. 12–17, 1993, by G.L. Schieven, et al., entitled "Identification of Reactive Oxygen Intermediate Responsive Tyrosine Kinases in Lymphocytes".

Abstract, Ninth International Symposium on Cellular Endocrinology: "Cell Signalling and the Molecular Stress Response", Lake Placid, New York, Sep. 23–26, 1993, by G.L. Schieven et al., entitled Identification of Reactive Oxygen Intermediate Responsive Tyrosine Kinases in Lymphocytes.

A. Shaver et al., "Insulin–Mimetic Peroxovanadium Complexes: Preparation and Structure of Potassium Oxodiperoxo (pyridine–2–carboxylato)vanadate(V), $K_2[VO(O_2)_2(C_5H_4NCOO)] \cdot 2H_2O$, and Potassium Oxidiperoxo (3–hydroxypyridine–2–carboxylato) vanadate(V), $K_2[VO(O_2)_2(OHC_5H_3NCOO)] \cdot 3H_2O$, and Their Reactions with Cysteine," *Inorg. Chem.* 32: 3109–3113 (1993).

J.P. Secrist et al., "Stimulatory Effects of the Protein Tyrosine Phosphatase Inhibitor, Pervanadate, on T–Cell Activation Events," *J. Biol. Chem.* 268:5886–5893 (1993).

F.M. Uckun et al., "Biotherapy of B–Cell Precursor Leukemia by Targeting Genistein to CD19–Associated Tyrosine Kinases," *Science* 267: 886–891 (1995).

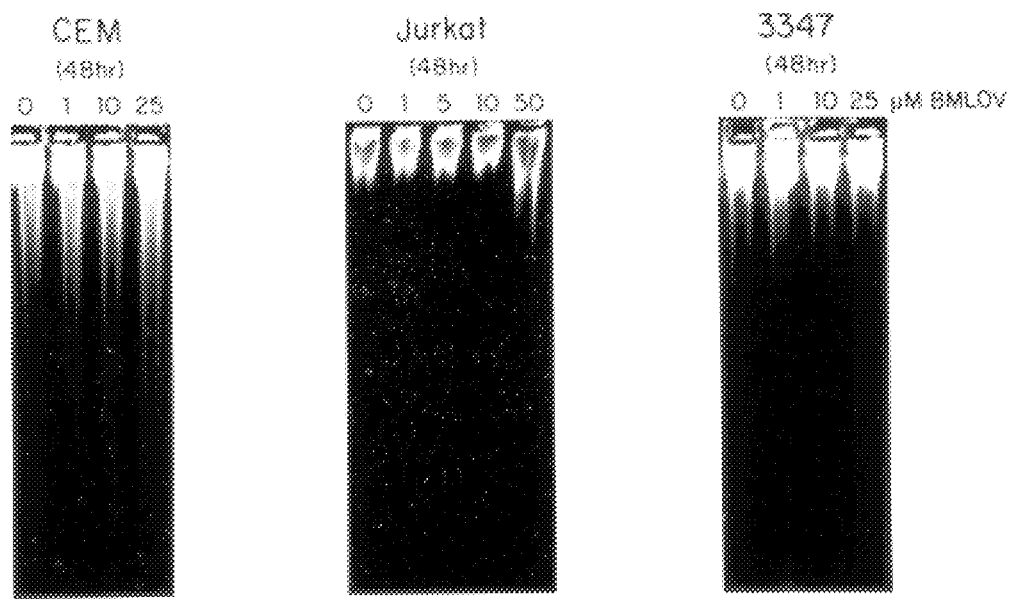

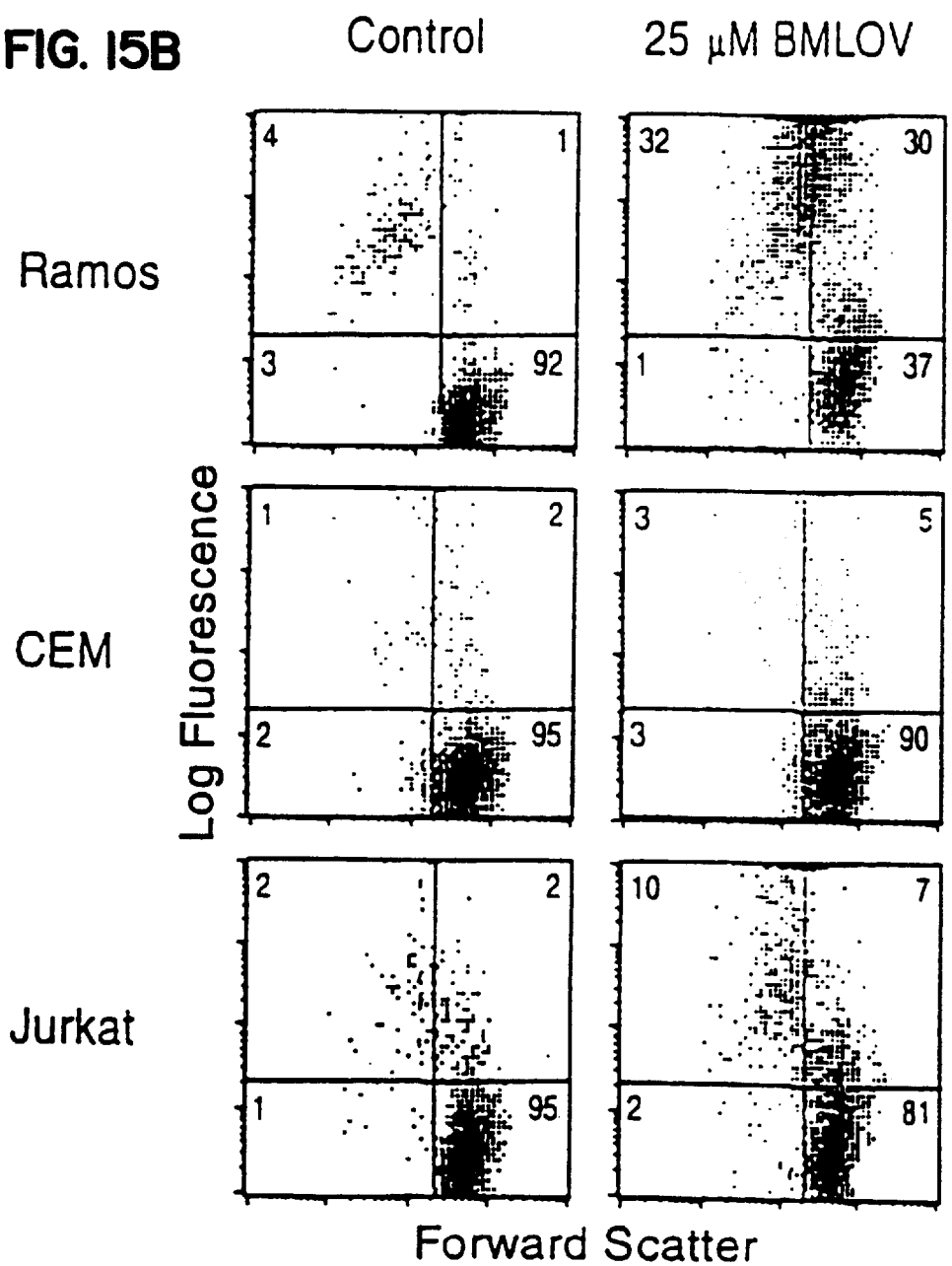

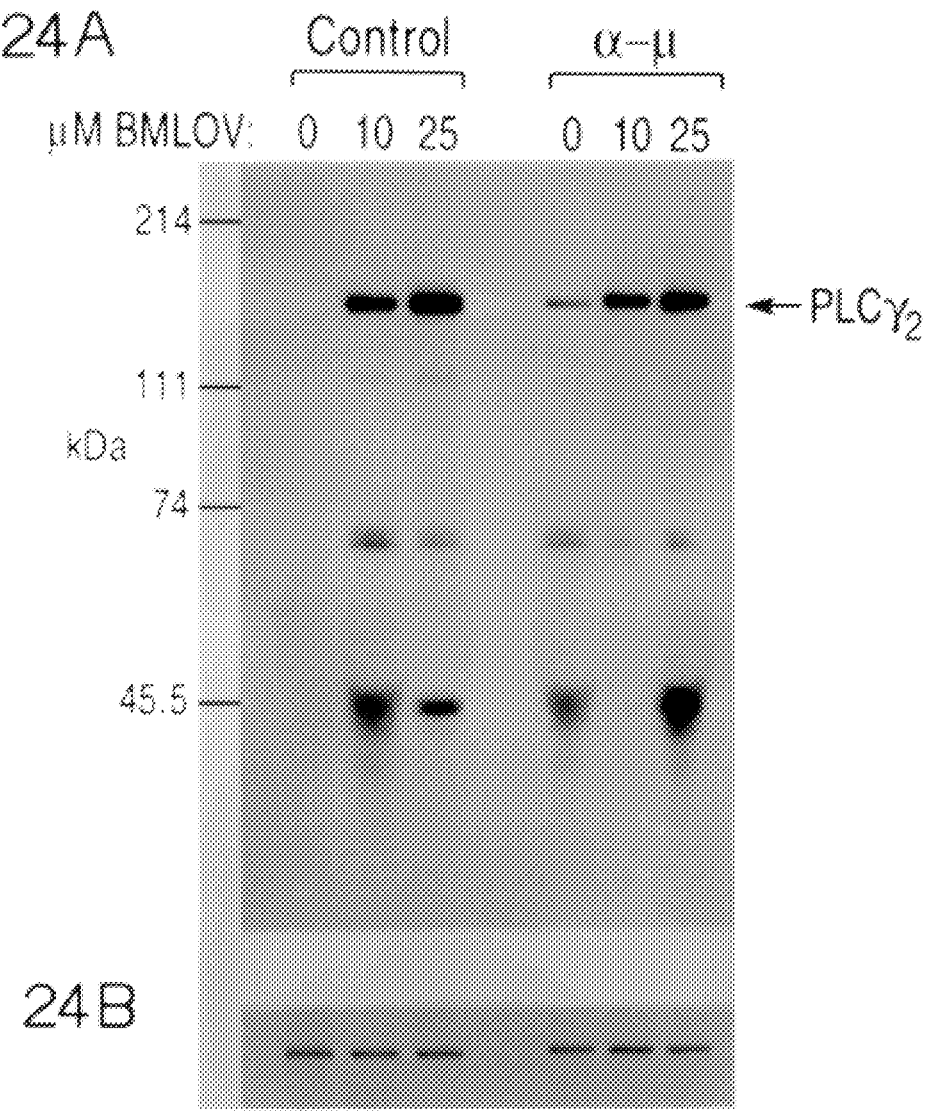

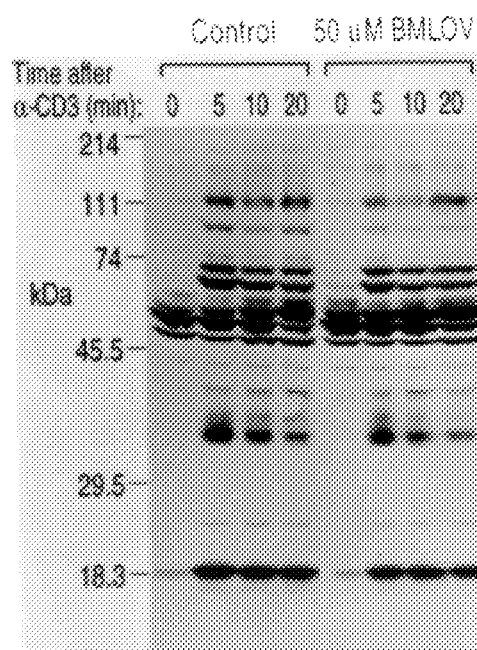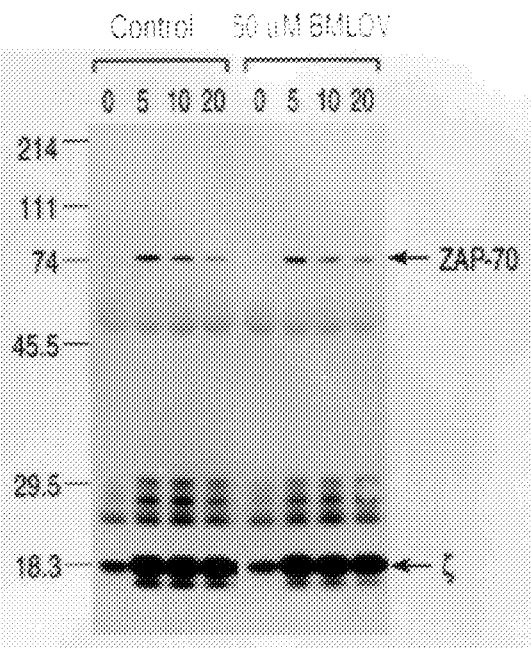
FIG. 26A
FIG. 26B
FIG. 26C

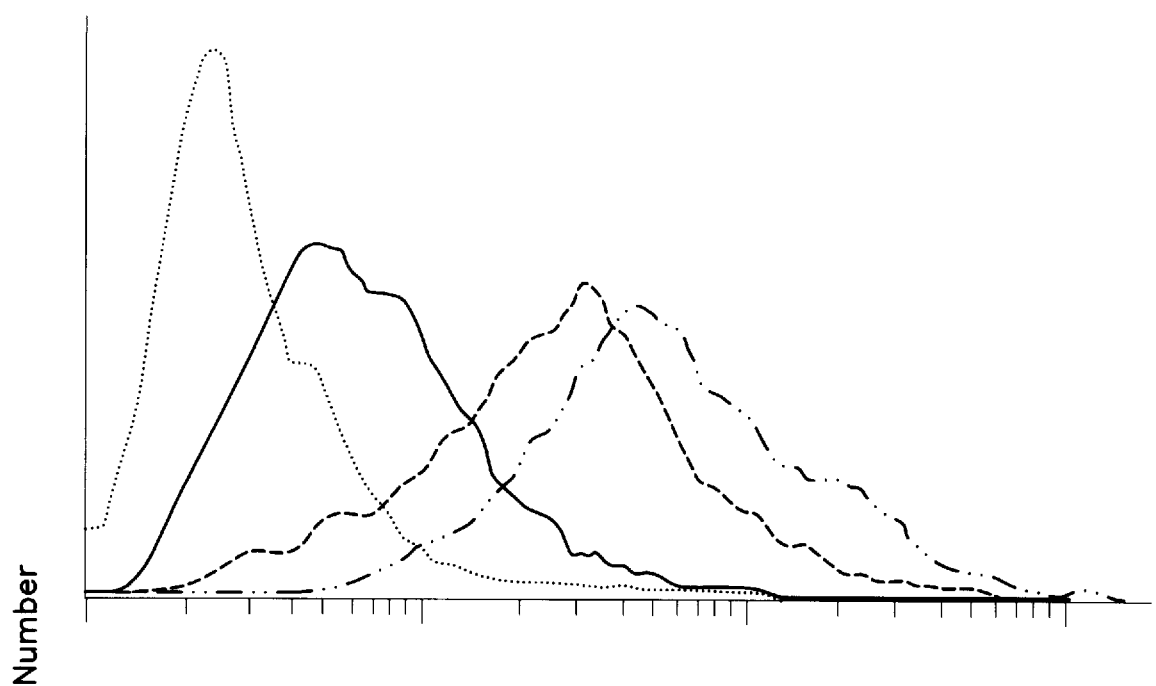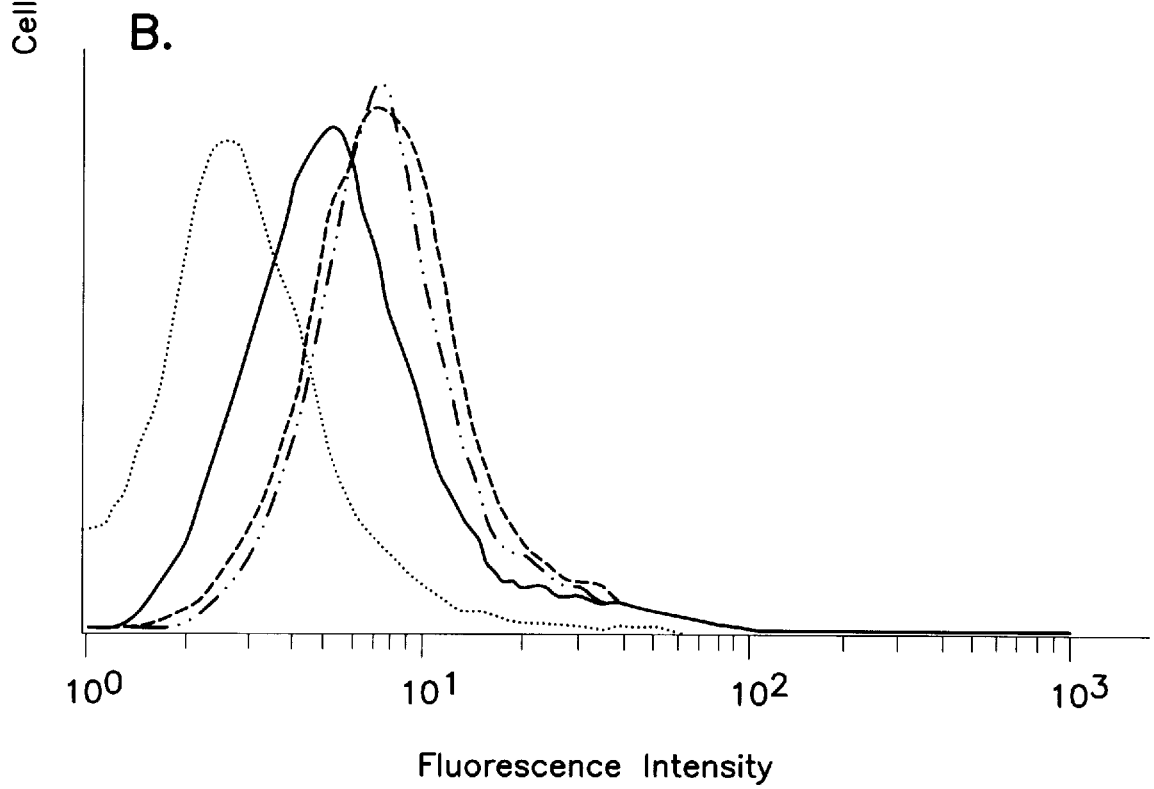
FIG. 28

PHOSPHOTYROSINE PHOSPHATASE INHIBITORS OR PHOSPHOTYROSINE KINASE ACTIVATORS FOR CONTROLLING CELLULAR PROLIFERATION

CROSS-REFERENCES

This application is a continuation-in-part of PCT Application Ser. No. PCT/US95/01234, filed Jan. 30, 1995 and designating the United States, entitled "Use of Phosphotyrosine Phosphatase Inhibitors or Phosphotyrosine Kinase Activators for Controlling Cellular Proliferation," by Gary L. Schieven, which was itself a continuation-in-part of U.S. application Ser. No. 08/189,330, filed Jan. 31, 1994, now U.S. Pat. No. 5,565,491, also entitled "Use of Phosphotyrosine Phosphatase Inhibitors or Phosphotyrosine Kinase Activators for Controlling Cellular Proliferation," by Gary L. Schieven. The disclosures of these two prior applications are incorporated herein in their entirety by this reference.

BACKGROUND OF THE INVENTION

This invention is directed to the use of phosphotyrosine phosphatase inhibitors and tyrosine kinase activators for controlling cellular proliferation, particularly proliferation of lymphocytes.

Tyrosine phosphorylation is known to play an essential role in the control of lymphocyte function. This control is exerted by a network of tyrosine kinases and phosphotyrosine phosphatases.

Apoptosis is a pattern of programmed cell death that involves a breakup of the cellular DNA and can be recognized by electrophoresis. Apoptosis is an important lymphocyte response believed to play a prominent role in T and B lymphocyte maturation in the thymus (T cells) and in germinal centers (B cells), an example being the process of negative selection of self-reactive cells (J. J. Cohen et al., "Apoptosis and Programmed Cell Death in Immunity," *Annu. Rev. Immunol.* 10:267–293 (1992); D. R. Green et al., "Activation-Induced Apoptosis in Lymphoid Systems," *Sem. Immunol.* 4:379–388 (1992)).

Three different means of inducing apoptosis in lymphocytes all appear to require tyrosine phosphorylation. First, stimulation of the antigen receptor can lead to lymphocyte apoptosis. In the case of B cells, treatment of immature B cell lymphomas, but not mature B cells, with soluble anti-Ig antibodies often induces apoptosis (L. E. Benhamou et al., "Anti-Immunoglobulins Induce Death by Apoptosis in WEHI-231 B Lymphoma Cells," *Eur. J. Immunol.* 20:1405–1407 (1990); J. Hasbold & G. G. B. Klaus, "Anti-Immunoglobulin Antibodies Induce Apoptosis in Immature B Cell Lymphomas," *Eur. J. Immunol.* 20:1685–1690 (1990) ). Signaling by anti-Ig antibodies requires tyrosine phosphorylation as an early and essential step (A. L. DeFranco, "Structure and Function of the B Cell Antigen Receptor," *Annu. Rev. Cell Biol.* 9:377–410 (1993)).

In immature B cells, stimulation of sIgM (surface immunoglobulin M) by either antigen or anti-immunoglobulin antibodies activates the cells (G. J. V. Nossal, *Annu. Rev. Immunol.* 1:33–62 (1983)). Stimulation of sIg (surface immunoglobulin) in B cells induces tyrosine phosphorylation (M. R. Gold et al., *Nature* 345:810–813 (1990); M. A. Campbell & B. M. Sefton, *EMBO J.* 9:2125–2131 (1990), which is essential for productive sIg signaling (P. J. L. Lane et al., *J. Immunol.* 146:715–722 (1991)).

Furthermore, specific tyrosine kinases appear to be involved in the B cell signaling that leads to apoptosis or growth arrest. For example, as a result of sIg stimulation, Src family kinases are activated (A. L. Burkhardt et al., *Proc. Natl. Acad. Sci. USA* 88:7410–7414 (1991)). Additionally, expression of the Src family tyrosine kinase Blk was found to be essential in B cell lymphomas where sIgM stimulation leads to growth arrest and apoptosis (X. R. Yao & D. W. Scott, "Expression of Protein Tyrosine Kinases in the Ig Complex of Anti-μ-Sensitive and Anti-μ-Resistant B Cell Lymphomas: Role of the $p55^{blk}$ Kinase in Signaling Growth Arrest and Apoptosis," *Immunol. Rev.* 132:163–186 (1993)). Similarly, the expression of the Blk tyrosine kinase has been found to be necessary for antigen receptor induced apoptosis in CH31 lymphoma cells (X. R. Yao & D. W. Scott, "Antisense Oligodeoxynucleotides to the blk Tyrosine Kinase Prevent Anti-μ-Chain-Mediated Growth Inhibition and Apoptosis in a B Cell Lymphoma," *Proc. Natl. Acad. Sci. USA* 90:7946–7950 (1993)), wherein the Lyn tyrosine kinase has been shown to be necessary for antigen receptor induced growth arrest in both human and murine B cell lymphoma lines (R. H. Scheuermann et al., "Lyn Tyrosine Kinase Signals Cell Cycle Arrest but Not Apoptosis in B-Lineage Lymphoma Cells," *Proc. Natl. Acad. Sci. USA* 91:4048–4052 (1994)).

Thus, on sIgM stimulation, tyrosine kinases such as Blk phosphorylate one or more proteins on tyrosine residues, and once phosphorylated, these proteins are then able to induce apoptosis. However, it has also been shown that the abundant phosphotyrosine phosphatase CD45 is required for sIg signal transduction (L. B. Justement et al., *Science* 252:1839–1842 (1991)).

The correlation of the ability of monoclonal anti-idiotypic antibodies to induce tyrosine phosphorylation signaling and their ability to produce lymphoma regression in human patients also supports the role of tyrosine phosphorylation in these processes (W. M. J. Vuist et al., "Lymphoma Regression Induced by Monoclonal Anti-Idiotypic Antibodies Correlates with Their Ability to Induce Ig Signal Transduction and Is Not Prevented by Tumor Expression of High Levels of Bcl-2 Protein," *Blood* 83:899–906 (1994)). In the case of T cells, the tyrosine kinase inhibitor herbimycin A prevented superantigen induced cell death that otherwise resulted from cross-linking multiple antigen receptors (N. K. Damle et al., "Activation with Superantigens Induces Programmed Death in Antigen-Primed CD4+ Class II+ Major Histocompatibility Complex T Lymphocytes Via a CD11a/CD18-Dependent Mechanism," *Eur. J. Immunol.* 23:1513–1522 (1993)).

A second example of the role of tyrosine phosphorylation in lymphocyte apoptosis is the case of Fas induced cell death in T cells. Crosslinking of Fas antigen on Jurkat T cell leukemia cells with anti-Fas antibodies induces both apoptosis and activation of tyrosine kinases leading to cellular tyrosine phosphorylation (C. M. Eischen et al., "Tyrosine Kinase Activation Provides an Early and Requisite Signal for Fas-Induced Apoptosis," *J. Immunol.* 153:1947–1954 (1994)). Herbimycin A blocked both the Fas induced tyrosine phosphorylation and death in these cells, demonstrating the essential role of the tyrosine kinases.

Apoptosis induced by ionizing radiation provides a third example. Ionizing radiation causes tyrosine kinase activation in human B cell lymphocyte precursors at therapeutically relevant doses that lead to growth arrest in apoptotic cell death (F. M. Uckun et al., "Ionizing Radiation Stimulates Unidentified Tyrosine-Specific Protein Kinases in Human B-Lymphocyte Precursors Triggering Apoptosis and Clonogenic Cell Death," *Proc. Natl. Acad. Sci. USA* 89:9005–9009 (1992)). Ionizing radiation is standard therapy for B cell malignancies such as leukemias and lymphomas. Tyrosine kinase inhibitors blocked the radiation-induced tyrosine phosphorylation and apoptosis. The phosphotyrosine phosphatase (PTP) inhibitor vanadate, which when used alone had little effect, greatly augmented the radiation-induced tyrosine phosphorylation and cell death (F. M. Uckun et al. (1992), supra). The activation of tyrosine kinases by ionizing radiation was essential for the induction of apoptosis because the tyrosine kinase inhibitors genistein and herbimycin A blocked the effects of the radiation. These results indicate that not only is tyrosine kinase activation essential for radiation induced apoptosis in B cells, but also suggest that phosphatases can act to limit these responses. The state of lymphocyte development also appears to be important in apoptotic responses since immature B cell lines frequently respond to Ig antibody treatment with apoptosis or growth arrest, whereas mature B cells respond by proliferation (R. H. Scheuermann et al. (1994), supra; X. R. Yao & D. W. Scott, Immunol. Rev. (1993), supra; G. J. V. Nossal, "Cellular and Molecular Mechanisms of B Lymphocyte Tolerance," Adv. Immunol. 52:283–331 (1992)).

Tyrosine kinase activation and the phosphorylation of key signaling molecules such as PLCγ are early and essential steps in lymphocyte antigen receptor signal transduction (A. Weiss & D. R. Littman, Cell 76: 263–274 (1994)). Src-family kinases are believed to act first, followed by the Syk family kinases Syk in B cells (S. J. Saouaf et al., Proc. Natl. Acad. Sci. USA 91: 9524–9528 (1994)) and ZAP-70 in T cells (M. Iwashima et al., Science 263: 1136–1139 (1994)). Phosphotyrosine phosphatases (PTP) provide both positive and negative regulation of these signals. CD45 is essential for signaling in both T and B cells, acting at least in part by dephosphorylating the negative regulatory C-terminal phosphorylation site in Src-family kinases, permitting them to become activated (A. Weiss & D. R. Littman (1994), supra; L. B. Justement et al., Science 252: 1839–1842 (1991)). However, CD45 can also negatively regulate T cell signaling by dephosphorylating specific substrates such as the ζ chain of the T cell receptor (T. Furukawa et al., Proc. Natl. Acad. Sci. USA 91: 10928–10932 (1994)). In addition, PTP1C has recently been reported to negatively regulate B cell antigen receptor signals (J. G. Cyster & C. C. Goodnow, Immunity 2: 13–24 (1995)). It is likely that additional PTPs are also involved in regulating lymphocyte signal transduction.

Although mature B cells usually respond to antigen receptor signals by proliferation, immature B cell lines frequently respond by undergoing apoptosis or programmed cell death (X. R. Yao & D. W. Scott, Immunol. Rev. 132: 163–186 (1993); R. H. Scheuermann et al., Proc. Natl. Acad. Sci. USA 91: 4048–4052 (1994); G. J. V. Nossal, Adv. Immunol. 52: 283–331 (1992)). This response permits the process of negative selection that eliminates self-reactive immature B cells. This activation induced B cell death requires specific tyrosine kinases involved in antigen receptor signaling, such as the Blk tyrosine kinase (X. R. Yao & D. W. Scott, Proc. Natl. Acad. Sci. USA 90: 7946–7950 (1993)). Recently, it has been reported that mice deficient in PTP1C more readily eliminate self-reactive B cells (J. G. Cyster & C. C. Goodnow (1995), supra), indicating a role for phosphotyrosine phosphatases in this process. Tyrosine kinase activation has also been found to be essential for the ability of therapeutically relevant doses of ionizing radiation to induce tyrosine phosphorylation and apoptosis in human leukemic B cells (F. M. Uckun et al., Proc. Natl. Acad. Sci. USA 89: 9005–9009 (1992)). Tyrosine kinase inhibitors blocked the radiation-induced tyrosine phosphorylation and apoptosis. The PTP inhibitor vanadate, which when used alone had little effect, greatly augmented the radiation-induced tyrosine phosphorylation and cell death (F. M. Uckun et al. (1992), supra). These results indicate that not only is tyrosine kinase activation essential for radiation induced apoptosis in B cells, but also suggest that phosphatases can act to limit these responses.

Despite these findings, the currently available PTP inhibitors are unsatisfactory for in vivo or clinical use. The PTP inhibitors phenylarsine oxide (PAO) (P. G. Garcia-Morales et al., Proc. Natl. Acad. Sci. USA 87: 9255–9259 (1990); M. C. Fletcher et al., J. Biol. Chem. 268: 23697–23703 (1993)) and pervanadate (J. J. O'Shea et al., Proc. Natl. Acad. Sci. USA 89: 10306–10310 (1993); G. L. Schieven et al., Blood 82: 1212–1220 (1993)) have properties that can limit their utility for biological studies and make them unsatisfactory for clinical use. PAO is a highly toxic molecule that has the potential to react with vicinal sulfhydryl groups on a wide variety of proteins (S. C. Frost & M. D. Lane, J. Biol. Chem. 260: 2646–2652 (1985)). Pervanadate is an unstable compound that can give extraordinary induction of tyrosine phosphorylation in the absence of biological stimulation in all cell types examined (D. Heffetz & Y. Zick, J. Biol. Chem. 264: 10126–10132 (1990); D. Heffetz et al., J. Biol. Chem. 265: 2896–2902 (1990)). Furthermore, the effect of PTP inhibition on B cell receptor signaling has not been addressed. Additionally, it would be highly desirable to be able to manipulate the state of tyrosine phosphorylation, such as by the use of phosphotyrosine phosphatase inhibitors, without the use of ionizing radiation.

In addition to blocking proliferation of malignant B cells or T cells in diseases such as leukemias and lymphomas, in a number of situations it may be desirable to slow the growth and/or differentiation of normal B cells or T cells. Such occasions include organ transplantation, in which the immune response, at least in the short term, must be suppressed. Limited control of the proliferation of B cells may also be desirable in the treatment of autoimmune diseases such as rheumatoid arthritis and lupus erythematosus.

Accordingly, there exists a need for improved methods of controlling proliferation of B cells or T cells in malignant and non-malignant conditions without requiring the use of radiation. Such an approach preferably involves the production of programmed cell death (apoptosis) in susceptible cells. Preferably, such methods should be specific for lymphocytes and not cause neutropenia. Also, such methods should be of value in treating tumors overexpressing one or more members of the EGF receptor family, other receptor tyrosine kinases, or other tyrosine kinases.

SUMMARY

I have developed a method of inhibiting the proliferation of B cells or T cells by using inhibitors of phosphotyrosine phosphatase and/or stimulators of tyrosine kinase.

Several types of inhibitors can be used, including: (1) compounds in which at least one peroxo group is bound to the metal; and (2) compounds in which no peroxo group is bound to the metal, but at least one oxo group is bound to the metal. In general, these compounds comprise:

(1) a metal ion selected from the group consisting of molybdenum (VI), vanadium (V), or tungsten (VI);

(2) at least one oxo group coordinate-covalently bound to the metal ion;

(3) at least one organic moiety coordinate-covalently bound to the metal ion through at least one N-containing, O-containing or As-containing moiety capable of donating electrons to a coordinate-covalent bond; and (4) optionally, one or two peroxo groups coordinate-covalently bound to the metal ion and occupying two sites in the coordination sphere of the metal ion. The coordinate-covalent complex has an affinity for the active site of a phosphotyrosine phosphatase sufficient to detectably inhibit the activity of one or more phosphotyrosine phosphatases. Preferably, the coordinate-covalent complex has an affinity for the active site of phosphotyrosine phosphatase at least about equal to the affinity of bis(maltolato) oxovanadium (IV) ("BMLOV") for the active site of phosphotyrosine phosphatase.

One particularly useful class of coordinate-covalent complex comprises:

(1) a metal ion selected from the group consisting of molybdenum (VI), tungsten (VI), and vanadium (V);

(2) an oxo group coordinate-covalently bound to the metal ion;

(3) at least one peroxo group coordinate-covalently bound to the metal ion; and (4) at least one organic moiety coordinate-covalently bound to the metal ion through at least one N-containing or O-containing functional group capable of donating electrons to a coordinate-covalent bond.

Preferred coordinate-covalent complexes include (1,10-phenanthroline) oxodiperoxovanadium (V) (known as pV(phen)), oxalato-oxodiperoxovanadium (V), (2,2'-bipyridine) oxodiperoxovanadium (V), (4,7-dimethyl-1,10-phenanthroline) oxodiperoxovanadium (V), (3,4,7,8-tetramethyl-1,10-phenanthroline) oxodiperoxovanadium (V), (pyridine-2-carboxylic acid) oxodiperoxovanadium (V), (5-hydroxypyridine-2-carboxylic acid) oxodiperoxovanadium (V), (pyridine-2,6-dicarboxylic acid) oxodiperoxovanadium (V), and derivatives thereof possessing substantially equivalent affinity for the active site of phosphotyrosine phosphatase. Other preferred coordinate-covalent complexes include (pyridine-2,6-dicarboxylato) (hydrato) oxoperoxovanadium (V), bis (dimethylformamido) oxodiperoxomolybdenum (VI), hydrogen (pyridine-2-carboxylato) oxodiperoxomolybdenum (VI) hydrate, [(N-salicylidene)-2-hydroxybenzeneamine] [ethanol] oxoperoxomolybdenum (VI), (pyridine-2,6-dicarboxylato) (hydrato) oxoperoxomolybdenum (VI), and bis(N-phenylbenzohydroxamato) oxoperoxomolybdenum (VI).

Another class of metal-organic coordinate-covalent complexes suitable for processes according to the present invention includes an oxo group coordinate-covalently bound to the metal ion, but no peroxo group. These complexes comprise:

(1) a metal ion selected from the group consisting of molybdenum (VI), tungsten (VI), and vanadium (V);

(2) an oxo group coordinate-covalently bound to the metal ion; and (3) at least one organic moiety coordinate-covalently bound to the metal ion through at least one N-containing or O-containing moiety capable of donating electrons to a coordinate-covalent bond. The coordinate-covalent complex has an affinity for the active site of phosphotyrosine phosphatase at least about equal to bis(maltolato) oxovanadium (IV) for the active site of phosphotyrosine phosphatase.

Preferred coordinate-covalent complexes belonging to this class include bis[benzene-1,2-di(dimethylarsino)] [chloro] oxomolybdenum (VI) and meso-tartrato oxovanadium (V).

These coordinate-covalent complexes can be used in the following methods:

(1) a method for inhibiting proliferation of a cell type selected from the group consisting of B cells, T cells, and cells derived from malignant transformation of B cells or T cells, comprising the step of contacting proliferating cells selected from the group consisting of B cells, T cells, and cells derived from malignant transformation of B cells or T cells with a coordinate-covalent complex as described above;

(2) a method of treating a subject suffering from a malignant proliferative disorder selected from the group consisting of leukemias and lymphomas wherein proliferating malignant cells are selected from the group consisting of B cells, T cells, cells derived from malignant transformation of B cells or T cells, and myeloid cells, the method comprising the step of contacting the proliferating malignant cells with a coordinate-covalent complex as described above;

(3) a method of treating a subject suffering from a malignant proliferative disorder selected from the group consisting of leukemias and lymphomas wherein the proliferating malignant cells are selected from the group consisting of B cells, T cells, cells derived from malignant transformation of B cells or T cells, and myeloid cells, the method comprising:

(i) contacting the proliferating malignant cells with a coordinate-covalent complex as described above; and (ii) delivering ionizing radiation to the cells contacted with the coordinate-covalent complex, the ionizing radiation being delivered in a dose sufficient to induce a substantial degree of cell killing among the malignantly proliferating cells, the degree of cell killing induced being substantially greater than that induced by either the coordinate-covalent complex or the ionizing radiation alone;

(4) a method of preventing the class-switching of antibody-producing cells comprising administering to antibody-producing cells a quantity of a coordinate-covalent complex as described above;

(5) a method of inducing tyrosine phosphorylation in a cell type selected from the group consisting of B cells, T cells, and cells derived from malignant transformation of B cells or T cells, comprising the step of contacting cells selected from the group consisting of B cells, T cells, and cells derived from malignant transformation of B cells or T cells with a coordinate-covalent complex as described above;

(6) a method of suppressing growth of tumor cells overexpressing a tyrosine kinase, such as, but not necessarily limited to, a tyrosine kinase selected from the group consisting of HER1, HER2, HER3, HER4, and Src, the method comprising the step of contacting tumor cells overexpressing a tyrosine kinase with a coordinate-covalent complex as described above;

(7) a method of suppressing growth of tumor cells requiring phosphotyrosine phosphatase for their growth and/or survival comprising the step of contacting tumor cells requiring phosphotyrosine phosphatase for their growth and/or survival with a coordinate-covalent complex as described above; and (8) a method of activating a tyrosine kinase that is a member of the Syk family of tyrosine kinases comprising the step of contacting a cell containing a member of the Syk family of kinases with a coordinate-covalent complex as described above.

In particular, the compound pV(phen) demonstrates antitumor activity in vivo and against tumor cell lines in culture.

Another aspect of the present invention is novel coordinate-covalent metal-organic complexes. These coordinate-covalent metal-organic complexes include: (1,10-phenanthroline) oxodiperoxomolybdenum (VI), (1,10-phenanthroline) oxodiperoxotungsten (VI), oxolato oxodiperoxomolybdenum (VI), (4,7-dimethyl-1,10-phenanthroline) oxodiperoxomolybdenum (VI), (4,7-dimethyl-1,10-phenanthroline) oxodiperoxotungsten (VI), (3,4,7,8-tetramethyl-1,10-phenanthroline) oxodiperoxomolybdenum (VI), (3,4,7,8-tetramethyl-1,10-phenanthroline) oxodiperoxotungsten (VI), (pyridine-2-carboxylic acid) oxodiperoxomolybdenum (VI), (pyridine-2-carboxylic acid) oxodiperoxotungsten (VI), (5-hydroxypyridine-2-carboxylic acid) oxodiperoxomolybdenum (VI), (5-hydroxypyridine-2-carboxylic acid) oxodiperoxotungsten (VI), (pyridine-2,6-dicarboxylic acid) oxodiperoxomolybdenum (VI), and pyridine-2,6-dicarboxylic acid) oxodiperoxotungsten (VI).

Yet another aspect of the invention is a method for stimulating $Ca^{2+}$ signaling in T cells with phosphotyrosine phosphatase inhibitors as described above.

Another aspect of the invention is a conjugate comprising a modulator of phosphotyrosine metabolism covalently conjugated to a specific binding partner for a cell surface receptor found on B cells. Preferably, the specific binding partner is anti-CD19 antibody. The modulator of phosphotyrosine metabolism can be either an inhibitor of phosphotyrosine phosphatase or an activator of tyrosine kinase. Conjugates according to the present invention can be used in methods of inhibiting B cell proliferation and in other methods.

BRIEF DESCRIPTION OF THE DRAWINGS

This file contains at least one drawing executed in color.

These and other features, aspects, and advantages of the present invention will become better understood with reference to the following description, appended claims, and accompanying drawings where:

FIG. 1, section B is a similar photograph of an anti-phosphotyrosine western blot showing the effects of treating the cells with 100 μM BMLOV for varying times;

FIG. 1, section C is a similar photograph of an anti-phosphotyrosine western blot, showing the high levels of phosphorylation reached after exposure to 50 μM BMLOV for 16 hours;

FIG. 2B is a similar photograph of a stained electropherogram of an agarose gel of DNA from the human T cell leukemia cell lines Jurkat and CEM, and the human colon carcinoma cell line 3347, after treatment of the cells with BMLOV, showing that apoptosis did not occur, demonstrating the selectivity of BMLOV;

FIG. 15B shows graphs of flow cytometric results to determine the viability of cells after growth in the presence of BMLOV; viability was measured by staining with propidium iodine followed by cytometric analysis, with the percentage of cells in each quadrant being indicated; the lower right quadrant contains the viable cells;

FIG. 24 shows the effect of BMLOV on phosphorylation of PLCγ2; Ramos B cells were treated 16 h with the indicated concentrations of BMLOV and then stimulated for 2 min with α-μ; antibody binding in immunoblots was detected by ECL; Panel A shows the anti-phosphotyrosine immunoblot of anti-PLCγ2 immunoprecipitates; in Panel B, the blot was stripped and reprobed with anti-PLCγ2 antibody to show recovery of the PLCγ2 protein;

FIG. 26 shows the minimal effect of BMLOV on basal or T cell receptor induced cellular tyrosine phosphorylation; cells were treated 16 h with BMLOV and then stimulated with anti-CD3 mAb G19-4 for 5 min; cells were then washed and resuspended in fresh media at equal concentrations of BMLOV at 37° C.; cells were then harvested and lysed at times following the initiation of CD3 stimulation as indicated; antibody binding in immunoblots was detected by ECL; Panel A shows anti-phosphotyrosine immunoblots of whole cell lysates; Panel B shows anti-phosphotyrosine immunoblots of anti-ZAP-70 immunoprecipitates prepared from the same samples; and Panel C shows anti-ZAP-70 immunoblots of anti-ZAP-70 immunoprecipitates prepared from the same samples;

FIG. 28 shows the results of TUNEL analysis; cells were treated with BMLOV for 48 h and TUNEL analysis was performed by flow cytometry; TUNEL analysis was performed without TDT as a control ( . . . ) and with TdT on cells treated with 0 (-), 25 μm (- - -),or 50 μM BMLOV (- . . . -); Panel A shows Ramos B cells; Panel B shows Jurkat T cells;

DESCRIPTION

Figure 1:
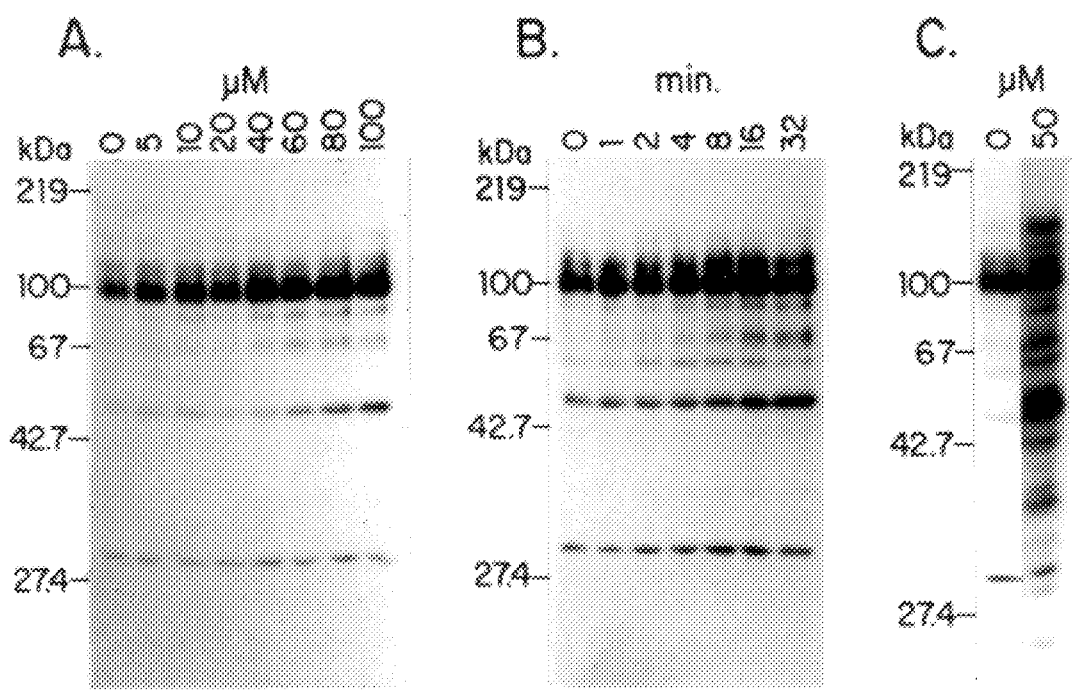
FIG. 1, section A is a photograph of an anti-phosphotyrosine western blot following sodium dodecyl sulfate-polyacrylamide electrophoresis of cell lysates from Ramos cells, a human B cell lymphoma cell line, after treatment with bis(maltolato)oxovanadium (IV) (BMLOV), showing the dose dependence of the resulting phosphorylation after a one-hour exposure to BMLOV.

I have developed an effective means of inhibiting phosphotyrosine phosphatase, particularly in B cells as well as in T cells, as well as novel compounds, including vanadyl compounds, molybdate compounds, and tungstate compounds, possessing inhibitory activity for phosphotyrosine phosphatase, and in some cases, stimulatory activity for tyrosine kinase.

The inhibition of phosphotyrosine phosphatase, as well as the stimulation of tyrosine kinase, can be used to inhibit the proliferation of both malignant and normal B cells or T cells, as well as other physiological functions depending on the balance between phosphorylated and dephosphorylated tyrosine residues.

I. PHOSPHOTYROSINE PHOSPHATASE INHIBITORS

In general, two types of phosphotyrosine phosphatase inhibitors are useful in the methods of the present invention. These are metal-organic coordinate-covalent compounds and nonhydrolyzable phosphotyrosine analogs. Other phosphotyrosine phosphatase inhibitors are also useful in the methods of the present invention.

A. Metal-Organic Coordinate-Covalent Compounds

Metal-organic coordinate-covalent compounds useful in the methods of the present invention include metal-organic coordinate-covalent compounds lacking an oxo or peroxo ligand coordinate-covalently bound to the metal, and metal-organic coordinate-covalent compounds having at least one oxo or peroxo ligand bound to the metal ion.

1. Compounds Lacking an Oxo or Peroxo Ligand

Metal-organic coordinate-covalent compounds lacking at least one oxo or peroxo ligand bound to the metal ion and useful in the methods of the present invention comprise a metal selected from the group consisting of vanadium (IV), copper (II) and gallium (II) coordinate-covalently bound to an organic moiety that can be either: (1) a keto-enol tautomer with keto and enol groups on adjacent carbon atoms and that forms a 5-membered ring including the metal; (2) a beta diketone in which the two keto groups are separated by one carbon atom that forms a 6-membered ring including the metal; (3) complexes in which the metal is preferably vanadium and the organic moiety contains at least one carbon-oxygen or carbon-nitrogen double bond; or (4) complexes of vanadyl and cysteine or cysteine derivatives.

For those compounds where the metal can be selected from the group consisting of vanadium (IV), copper (II) and gallium (II), the metal is preferably vanadium (IV). Other metals can give different patterns of inhibition in particular cell types.

a. Keto-Enol Tautomers

If the organic moiety is a keto-enol tautomer forming a 5-membered ring including the metal, it is preferably one of the following moieties: maltol, kojic acid, 2-hydroxy-2,4,6-cycloheptatrien-1-one, 3-bromo-2-hydroxy-2,4,6-cycloheptatrien-1-one, 2-hydroxy-4-isopropyl-2,4,6-cycloheptatrien-1-one, 2-hydroxy-4-methyl-2,4,6-cycloheptatrien-1-one, 3-hydroxy-1,2-dimethyl-4(1H)-pyridone, 3-ethyl-2-hydroxy-2-cyclopenten-1-one, 3,4-dihydroxy-3-cyclobuten-1,2-dione, ethyl 2-hydroxy-4-oxo-2-pentenone, 2,3,5,6-tetrahydroxy-1,4-benzoquinone, 2',4'-dihydroxy-2-methoxyacetophenone, 4-hydroxy-5-methyl-4-cyclopenten-1,3-dione, 2-chloro-3-hydroxy-1,4-naphthoquinone, 2-(4-bromophenyl)-3-hydroxymaleimide, 2-hydroxy-3-methyl-2-cyclopenten-1-one, 2',3',4'-trihydroxyacetophenone, furoin, 2-hydroxy-2-methylpropiophenone, maclurin, 6-(pyrrolidinomethyl) kojic acid, alpha-acetyl-4-hydroxy-beta-(hydroxymethyl)-3-methoxycinnamic acid gamma-lactone, 4-hydroxy-5-phenyl-4-cyclopenten-1,3-dione, 6-(morpholinomethyl) kojic acid, 1-(4,5-dimethoxy-2-hydroxyphenyl)-3-methyl-2-buten-1-one, purpurogallin, 2,3-dihydroxy-1,4-phenazinedione, alizarin orange, 1-hydroxy-1-methylnaphthalen-2(1H)-one, alizarin, 6-(piperidinomethyl) kojic acid, 1,2,7-trihydroxyanthraquinone, 6-(4-methylpiperazinomethyl) kojic acid, fisetin, 3-oxo-4,5,6-trihydroxy-3(H)-xanthene-9-propionic acid, benzoin, 4'-chlorobenzoin, quercetin, morin, myricetin, or 4,4'-dimethylbenzoin. More preferably, the organic moiety is maltol, and the resulting compound is bis(maltolato) oxovanadium (IV) ("BMLOV").

b. Beta Diketones

If the organic moiety is a beta diketone, the organic moiety is preferably one of the following moieties: acetylacetone, 2-acetyl-1-tetralone, benzoylacetone, 1-benzoylacetylacetone, 1,1,1-trifluoro-2,4-pentanedione, S-methyl-4,4,4-trifluoro-3-oxothiobutyrate, 2-acetyl-1,3-cyclopentanedione, 3-chloro-2,4-pentanedione, 1,1,1,5,5,5-hexafluoro-2,4-pentanedione, 3-ureidomethylene-2,4-pentanedione, 2-acetylcyclopentanone, 2-acetylcyclohexanone, 3-methyl-2,4-pentanedione, 2,4,6-heptatrione, 3-ethyl-2,4-pentanedione, thianoyltrifluoroacetone, S-t-butyl-acetothioacetate, 3-acetyl-5-methylhexan-2-one, 3-acetyl-2-heptanone, 2,2-dimethyl-6,6,7,7,8,8,8-heptafluoro-3,5-octanedione, 4-hydroxy-5-phenyl-4-cyclopenten-1,3-dione, 4,4,4-trifluoro-1-phenyl-1,3-butanedione, 3-acetyl-2-octanone, 1(2-hydroxy-4-methylphenyl)-1,3-butanedione, 1-(2-hydroxy-5-methylphenyl)-1,3-butanedione, 3-benzylidene-2,4-pentanedione, 1-(2-hydroxy-5-methylphenyl)-1,3-pentanedione, 2,2,6,6-tetramethyl-3,5-heptanedione, 3-acetyl-5-hydroxy-2-methylchromone, (+)-3-(trifluoroacetyl)camphor, 4,9-dihydro-6-methyl-5H-furo(3,2-g) (1) benzopyran-4,5,9-trione, 3-(2-nitrobenzylidene)-2,4-pentanedione, 1,3-bis(4-chlorophenyl)-1,3-propanedione, 1,3-bis-(4-fluorophenyl)-1,3-propanedione, 4,4,4-trifluoro-1-(2-naphthyl)-1,3-butanedione, 1-(2-hydroxyphenyl)-3-(4-methoxyphenyl)-1,3-propanedione, 2-bromo-1,3-diphenyl-1,3-propanedione, dibenzoylmethane, 2-(4-chlorobenzylidene)-1-phenyl-1,3-butanedione, 2-(2-nitrobenzylidene)-1-phenyl-1,3-butanedione, bis(4-methoxybenzoyl) methane, and curcumin. Preferably, the organic moiety is acetylacetone, and the resulting compound is vanadyl acetylacetonate.

Among novel compounds containing vanadium coordinate-covalently bound to an organic moiety that are believed to have activity as phosphotyrosine phosphatase inhibitors are the compounds vanadyl 2-acetyl-1-tetralone, vanadyl 2-hydroxy-4-isopropyl-2,4,6-cycloheptatrien-1-one, and vanadyl 2-hydroxy-4-methyl-2,4,6-cycloheptatrien-1-one.

c. Complexes in which the Metal is Preferably Vanadium and the Organic Moiety Contains at Least one Carbon-Oxygen or Carbon-Nitrogen Double Bond Other metal-organic coordinate covalent compounds useful for the processes of the present invention include complexes in which the metal is preferably vanadium and the organic moiety is one of formulas I through IX, of which formula I is a general formula and formulas II through IX represent particular classes of compounds of formula I.

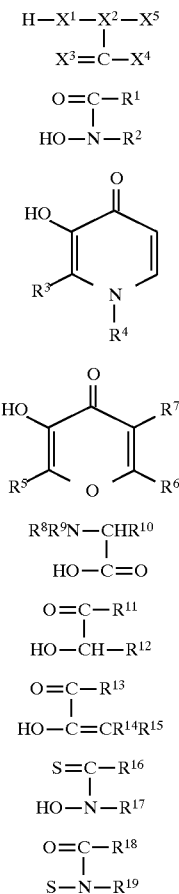

In formula I, $X^1$ and $X^3$ are independently oxygen, sulfur, or $NX^6$, preferably oxygen or $NX^6$. $X^2$ is nitrogen or $CX^7$. $X^4$, $X^5$, $X^6$, and $X^7$ are independently non-labile protons or optionally substituted alkyl, aryl, aralkyl or alkaryl. Alternatively, at least one pair of $X^4$ to $X^7$, preferably $X^4$ and $X^5$, together with the intervening atoms can represent an optionally substituted, saturated or unsaturated homocyclic or heterocyclic ring. Alternatively, where $X^1$ is a $NX^6$ group, $X^4$ can represent a group $X^8H$ where $X^8$ is oxygen or sulfur, and one proton attached to $X^1$ or $X^8$, preferably a proton attached to $X^1$, is labile.

Typical organic moieties of formula I are α-amino acids (other than cysteine), hydroxamates, thiohydroxamates, α-hydroxycarbonyls such as α-hydroxypyridinones or α-hydroxypyrones.

When the organic moiety comprises a homocyclic or heterocyclic ring, the ring is preferably a 5-, 6-, or 7-membered ring. If the ring is heterocyclic, it can contain 1, 2, or 3 heteroatoms, typically 1. The heteroatoms are selected from O, N, and S, and are preferably O or N. Each aryl group is preferably phenyl or naphthyl, typically phenyl. Each alkyl group or moiety contains 1 to 6 carbon atoms, typically 1 to 4. The optional substituents, which do not include thiol groups, are preferably selected from hydroxy, alkoxy, oxo, amide, and amine groups, as well as alkyl groups carrying such substituents. These groups can be selected for their ability to enhance the hydrophilicity or lipophilicity of the complex or to enable the complex to be conjugated to another molecule such as a protein, a polymer, or another biologically active molecule.

Particularly suitable organic moieties include the hydroxamates of formula II, the α-hydroxypyridinones of formula III, the α-hydroxypyrones of formula IV, the α-amino acids of formula V, the hydroxycarbonyls of formulas VI and VII, and the thiohydroxamates of formulas VIII and IX. In these formulas, $R^1$ to $R^{19}$ are hydrogen or optionally substituted, e.g., hydroxylated, $C_1$ to $C_4$ alkyl.

d. Complexes of Vanadyl and Cysteine or Cysteine Derivatives

Still other metal-organic coordinate covalent compounds are useful in processes according to the present invention. These coordinate covalent compounds are complexes of vanadyl and cysteine or cysteine derivatives and have the general structure shown in formula X:

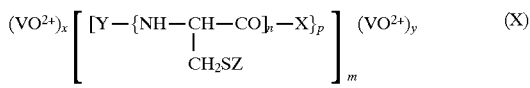

In formula X, either x is 1 and y is 0 or x is 0 and y is 1. The values of n, p, and m are 1 or 2. The cysteine moiety can be D-cysteine or L-cysteine.

When p is equal to 1, then Y is selected from the group consisting of a hydrogen atom and a R'-CO group.

When n is equal to 1 and m is equal to 2, X is selected from the group consisting of an OH group, an OR group, and an NHR group wherein R is selected from the group consisting of an alkyl group comprising from 2 to 9 carbon atoms, an aryl group, or an aralkyl group. In this structure, when X is an OH group, Y is a R'-CO group wherein R' is selected from the group consisting of an alkyl group comprising from 2 to 9 carbon atoms, and, when X is selected from the group consisting of an OR group and a NHR group, Y is H.

When n is equal to 2 and m is equal to 1, X is selected from the group consisting of a difunctional amine of formula $WC[CH_2NH-]_2$, a difunctional alcohol of formula $WC[CH_2O-]_2$, and a difunctional amine-alcohol of formula $WC(CH_2NH-)(CH_2O-)$, wherein W is an alkyl group of from 2 to 9 carbon atoms.

When p is equal to 2, then n is equal to 1, m is equal to 1, X is an OH group, and Y is selected from the group consisting of $ZCH(CO-)_2$, $-CH_2-$, or $ZCH(CH_2-)_2$ in which Z is an alkyl, aryl, or aralkyl group.

One class of compounds of this type has x equal to 1, y equal to 0, and p equal to 1. In this class of compounds, Y is hydrogen and Z is a minus charge. This class of compounds has a free amine group that is bound to the vanadyl; the ligand bound to the vanadyl is bimolecular, in that two organic moieties are complexed to a single vanadyl ion. The ligand has a negative charge on a sulfur atom. This class of compounds is depicted in formula XI.

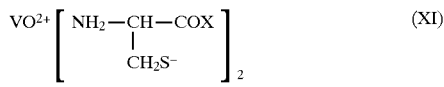

(XI)

In formula XI, X is an —OR group or a —NHR (amine) group, in which the R moiety is an aryl or aralkyl group or an alkyl group other than methyl. Where X is a —NHR group, the compound is a complex of vanadyl with an amide of cysteine such as a butylamide of cysteine or an octylamide of cysteine. The vanadyl-octylamide complex of L-cysteine is shown in formula XIa.

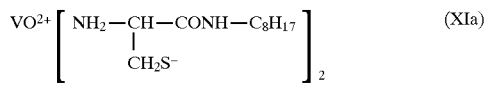

(XIa)

Where X is an -OR group, the compound is, for example, a complex of vanadyl with an ester of the cysteine, such as an octylester of cysteine or a butylester of cysteine.

Another class of compounds of this type has n equal to 2 and m equal to 1. In this class of compounds, the ligand is monomolecular. This class of compounds is depicted in formula XII.

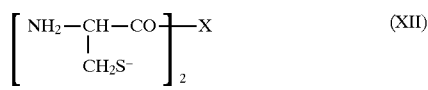

(XII)

In formula XII, X corresponds to a difunctional amine of formula $WC[CH_2NH—]_2$, a difunctional alcohol of formula $WC[CH_2O—]_2$, or a difunctional amine-alcohol of formula $WC(CH_2NH—)(CH_2O—)$. R is an alkyl group of from 2 to 9 carbon atoms.

Yet another class of compounds of this type has x equal to 0, y equal to 1, and n equal to 1. In this class of compounds, X is a O group and Z is hydrogen. This class of compounds includes a bimolecular ligand comprising a free carboxyl group and is depicted in formula XIII.

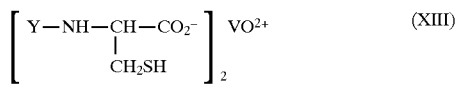

(XIII)

In molecules of formula XIII, Y corresponds to a R-CO (ketone) group in which the R moiety is an alkyl, aryl, or aralkyl group.

Yet another class of compounds of this type has p equal to 2 and m equal to 1. This class of compounds includes a monomolecular ligand comprising two free carboxyl groups and is depicted in formula XIV.

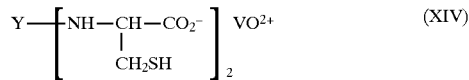

(XIV)

In molecules of formula XIV, Y corresponds to a group of formula $ZCH(CO—)_2$, $—CH_2—$, or $ZCH(CH_2—)_2$ in which Z is an alkyl, aryl, or aralkyl group.

Still another class of compounds of this type has x equal to 0, y equal to 1, Y a $CH_2$ group, and Z a minus charge. In this class of compounds, n and p are each 1 and m is 2. This class of compounds includes a monomolecular ligand with substituted amino and carboxyl groups and is depicted in formula XV.

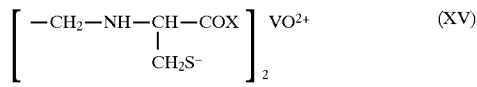

(XV)

In formula XV, X is an —OR group or a —NHR (amine) group, in which the R moiety is an aryl or aralkyl group or an alkyl group other than methyl.

B. Coordinate-Covalent Metal-Organic Compounds Containing at Least One Oxo or Peroxo Ligand Bound to the Metal Another class of metal-organic coordinate-covalent compounds useful in the processes of the present invention has at least one oxo or peroxo ligand coordinate-covalently bound to the metal. These coordinate-covalent metal-organic compounds include: (1) compounds in which at least one peroxo group is bound to the metal; and (2) compounds in which no peroxo group is bound to the metal, but at least one oxo group is bound to the metal. In general, these compounds comprise:

(1) a metal ion selected from the group consisting of molybdenum (VI), vanadium (V), or tungsten (VI);

(2) at least one oxo group coordinate-covalently bound to the metal ion;

(3) at least one organic moiety coordinate-covalently bound to the metal ion through at least one N-containing, O-containing or As-containing moiety capable of donating electrons to a coordinate-covalent bond; and (4) optionally, one or two peroxo groups coordinate-covalently bound to the metal ion and occupying two sites in the coordination sphere of the metal ion. The coordinate-covalent complex has an affinity for the active site of a phosphotyrosine phosphatase sufficient to detectably inhibit the activity of one or more phosphotyrosine phosphatases. As used herein, the term "detectably inhibit" means a degree of inhibition that can be determined, within experimental error, by assays measuring the dephosphorylation of a suitable substrate for phosphatases, such as phosphorylated myelin basic protein. Typical phosphotyrosine phosphatases that can be used to determine the activity of compounds include, but are not limited to, the phosphatases PTP1B and CD45. Preferably, the coordinate-covalent complex has an affinity for the active site of phosphotyrosine phosphatase at least about equal to the affinity of bis(maltolato) oxovanadium (IV) for the active site of phosphotyrosine phosphatase.

1. Coordinate-Covalent Metal-Organic Compounds With at Least One Peroxo Ligand Bound to the Metal Ion One particularly useful class of coordinate-covalent complex comprises:

(1) a metal ion selected from the group consisting of molybdenum (VI), tungsten (VI), and vanadium (V);

(2) an oxo group coordinate-covalently bound to the metal ion;

(3) at least one peroxo group coordinate-covalently bound to the metal ion; and (4) at least one organic moiety coordinate-covalently bound to the metal ion through at least one N-containing or O-containing functional group capable of donating electrons to a coordinate-covalent bond.

The coordinate-covalent complex has an affinity for the active site of a phosphotyrosine phosphatase sufficient to detectably inhibit the activity of one or more phosphotyrosine phosphatases. Preferably, the coordinate-covalent complex has an affinity for the active site of phosphotyrosine phosphatase at least about equal to the affinity of bis (maltolato) oxovanadium (IV) for the active site of phosphotyrosine phosphatase.

In one group of metal-organic compounds useful in the processes of the present invention, the metal ion is vanadium (V).

In one group of metal-organic compounds useful for the processes of the present invention, the coordinate-covalent complex has two peroxo groups bound to the metal ion. Each of the peroxo groups occupies two sites in the coordination sphere of the metal ion.

When the metal is vanadium (V), preferred coordinate-covalent complexes include (1,10-phenanthroline) oxodiperoxovanadium (V), oxalato-oxodiperoxovanadium (V), (2,2'-bipyridine) oxodiperoxovanadium (V), (4,7-dimethyl-1,10-phenanthroline) oxodiperoxovanadium (V), (3,4,7,8-tetramethyl-1,10-phenanthroline) oxodiperoxovanadium (V), (pyridine-2-carboxylic acid) oxodiperoxovanadium (V), (5-hydroxypyridine-2-carboxylic acid) oxodiperoxovanadium (V), (pyridine-2,6-dicarboxylic acid) oxodiperoxovanadium (V), and derivatives thereof possessing substantially equivalent affinity for the active site of phosphotyrosine phosphatase. In particular, the 1,10-phenanthroline, 2,2'-bipyridine, 4,7-dimethyl-1,10-phenanthroline, 3,4,7,8-tetramethyl-1,10-phenanthroline, pyridine-2-carboxylic acid, 5-hydroxypyridine-2-carboxylic acid, and pyridine-2,6-dicarboxylic acid nuclei can be substituted with hydroxy, lower alkyl ($C_1$–$C_5$), or other substituents that do not significantly affect the binding to the metal ion.

One particularly preferable coordinate-covalent complex for use in methods according to the present invention is (1,10-phenanthroline) oxodiperoxovanadium (V), also referred to as pV(phen).

When the metal is vanadium and the coordinate-covalent complex has one peroxo group bound to the metal ion, a preferred coordinate-covalent complex is (pyridine-2,6-dicarboxylato) (hydrato) oxoperoxovanadium (V).

When the metal ion in the coordinate-covalent complex is molybdenum (VI), and the coordinate-covalent complex has two peroxo groups bound to the metal ion, preferred coordinate-covalent complexes include bis (dimethylformamido) oxodiperoxomolybdenum (VI) and hydrogen (pyridine-2-carboxylato) oxodiperoxomolybdenum (VI) hydrate.

When the metal is molybdenum (VI) and the coordinate-covalent complex has one peroxo group bound to the metal ion, preferred coordinate-covalent complexes include [(N-salicylidene)-2-hydroxybenzeneamine] [ethanol] oxoperoxomolybdenum (VI), (pyridine-2,6-dicarboxylato) (hydrato) oxoperoxomolybdenum (VI), and bis(N-phenylbenzohydroxamato) oxoperoxomolybdenum (VI).

2. Coordinate-Covalent Complexes Including an Oxo Group Coordinate-Covalently Bound to the Metal Ion but Without a Peroxo Group Another class of metal-organic coordinate-covalent complexes suitable for processes according to the present invention includes an oxo group coordinate-covalently bound to the metal ion, but no peroxo group. These complexes comprise:

(1) a metal ion selected from the group consisting of molybdenum (VI), tungsten (VI), and vanadium (V);

(2) an oxo group coordinate-covalently bound to the metal ion; and (3) at least one organic moiety coordinate-covalently bound to the metal ion through at least one N-containing or O-containing moiety capable of donating electrons to a coordinate-covalent bond. The coordinate-covalent complex has an affinity for the active site of a phosphotyrosine phosphatase sufficient to detectably inhibit the activity of one or more phosphotyrosine phosphatases. Preferably, the coordinate-covalent complex has an affinity for the active site of phosphotyrosine phosphatase at least about equal to bis(maltolato) oxovanadium (IV) for the active site of phosphotyrosine phosphatase.

When the metal ion is molybdenum in a complex containing an oxo group but no peroxo group, a preferred coordinate-covalent complex is bis[benzene-1,2-di (dimethylarsino)] [chloro] oxomolybdenum (VI).

When the metal ion is vanadium in a complex containing an oxo group but no peroxo group, a preferred coordinate-covalent complex is meso-tartrato oxovanadium (V).

For these coordinate-covalent complexes as well, the organic moiety can be substituted with hydroxy or lower alkyl that does not interfere with the coordinate-covalent bond between the N-containing or O-containing moiety and the metal ion.

C. Nonhydrolyzable Phosphotyrosine Analogs

Another class of phosphotyrosine phosphatase inhibitors useful in the methods of the present invention is nonhydrolyzable phosphotyrosine analogs. These analogs can be either: (1) N-aryl phosphoramidates; (2) N-aryl phosphorothioates; or (3) N-aryl phosphonates. The N-aryl phosphoramidates have the structure shown in formula XVI, the N-aryl phosphorothioates have the structure shown in formula XVII, and the N-aryl phosphonates have the structure shown in formula XVIII.

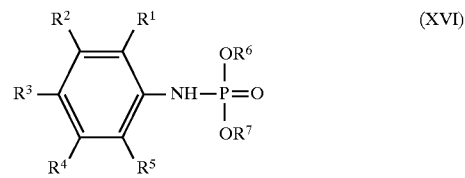

(XVI)

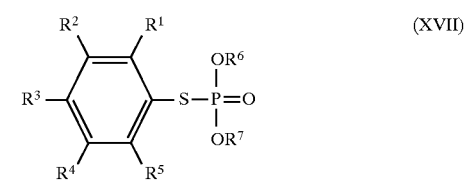

(XVII)

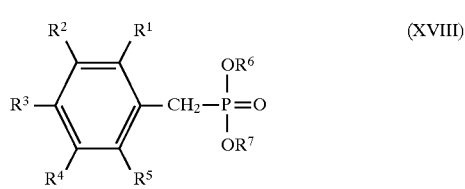

(XVIII)

In either the N-aryl phosphoramidates, the N-aryl phosphorothioates, or the N-aryl phosphonates, the aryl moiety can be optionally substituted at any of the ortho, meta, and/or para positions. Similarly, one or two of the oxygen atoms bound to the phosphorus are optionally esterified.

In the N-aryl phosphoramidate of formula XVI, each of $R_1$ through $R_7$ can be selected from the group consisting of hydrogen and $C_1$–$C_5$ alkyl, which can be either straight-chain or branched-chain. Preferably, each of $R_1$ through $R_5$ is hydrogen. Preferably, when each of $R_1$ through $R_5$ is hydrogen, at least one of $R_6$ and $R_7$ is other than hydrogen.

When the nonhydrolyzable phosphotyrosine analog is a phosphorothioate of formula XVII, preferably each of $R_1$ through $R_7$ is hydrogen or $C_1$–$C_5$ alkyl, which can be either straight-chain or branched-chain. Preferably, each of $R_1$ through $R_5$ is hydrogen. Preferably, each of $R_1$ through $R_5$ is hydrogen, at least one of $R_6$ and $R_7$ is other than hydrogen.

Similarly, when the nonhydrolyzable phosphotyrosine analogue is a phosphonate of formula XVIII, preferably each of $R_1$ through $R_7$ is hydrogen or $C_1$–$C_5$ alkyl, which can be either straight-chain or branched-chain. Preferably, each of $R_1$ through $R_5$ is hydrogen. Preferably, when each of $R_1$ through $R_5$ is hydrogen, at least one of $R_6$ and $R_7$ is other than hydrogen.

D. Additional Phosphotyrosine Phosphatase Inhibitors

Additional phosphotyrosine phosphatase inhibitors exist that are useful in methods according to the present invention. These additional phosphotyrosine phosphatase inhibitors include dephostatin and 4-(fluoromethyl)phenyl phosphate and its esterified derivatives.

1. Dephostatin

Dephostatin is a phosphotyrosine phosphatase inhibitor isolated from Streptomyces sp. MJ742-NF5 (M. Imoto et al., "Dephostatin, a Novel Protein Tyrosine Phosphatase Inhibitor Produced by Streptomyces. I. Taxonomy, Isolation, and Characterization," *J. Antibiotics* 46: 1342–1346 (1993)). It has structure XIX shown below.

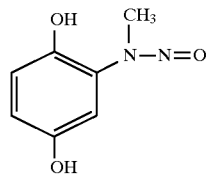

(XIX)

and is a competitive inhibitor of phosphotyrosine phosphatase, competing with the substrate for the enzyme. Dephostatin can be extracted from the broth filtrate of a Streptomyces culture with ethyl acetate and purified by silica gel chromatography and high-pressure liquid chromatography (HPLC).

2. 4-(Fluoromethyl)Phenyl Phosphate and Its Esterified Derivatives

The inhibitor of human prostatic acid phosphatase 4-(fluoromethyl)phenyl phosphate (formula XX; $R_1$ and $R_2$ each H) (J. K. Myers & T. S. Widlanski, "Mechanism-Based Inactivation of Prostatic Acid Phosphatase," *Science* 262: 1451–1453 (1993)), together with its esterified derivatives, are also phosphotyrosine phosphatase inhibitors that are useful in processes according to the present invention. In compounds of formula XX useful in processes according to the present invention, $R_1$ and $R_2$ are either hydrogen or $C_1$–$C_5$ alkyl, which can be either straight-chain or branched-chain. Preferably, at least one of $R_1$ and $R_2$ is $C_1$–$C_5$ alkyl.

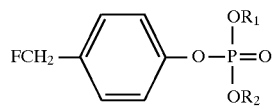

(XX)

E. Synthesis of Compounds

1. Synthesis of Metal-Organic Coordinate-Covalent Compounds

Metal-organic coordinate-covalent compounds can be synthesized by the general method described for bis (maltolato) oxovanadium (IV) in J. H. McNeill et al., "Bis(maltolato) Oxovanadium (IV) Is a Potent Insulin Mimic," *J. Med. Chem.* 35:1489–1491 (1992).

In general, the compounds are prepared by combining the organic ligand (maltol for BMLOV) and vanadyl sulfate in a 2:1 ratio, raising the pH of the solution to 8.5, refluxing overnight, and collecting the compound that precipitates on cooling.

In a generalization of this method, the organic moiety is dissolved in water at alkaline pH. Depending upon the compound, a higher pH may be required for solubilization. For some compounds, a water-miscible, less polar solvent may need to be added to dissolve the compound. Such solvents can include aprotic solvents such as acetonitrile, dimethylsulfoxide, or dimethylformamide, although other suitable solvents are also known in the art. Vanadyl sulfate, or another metal salt if desired, is then added in a sufficient quantity to achieve a 2:1 molar ratio between the organic moiety and the metal salt. The solution is then heated with a condenser attached to the reaction flask to permit refluxing. Following the reaction, the solution is then cooled and the product is recovered as a precipitated solid. In some cases, the product may not precipitate, and can then be recovered by rotary evaporation of the solvent or by other means, such as chromatography.

Vanadium chelates with ligands of Formula I could be prepared in a one-pot synthesis analogous to that described for gallium, aluminum, or indium complexes by Zhang et al., *Can. J. Chem.* 67:1708–1710 (1989).

In general, the compounds of Formula X are synthesized by the following process: (1) reacting a mono- or bifunctional amine or mono- or bifunctional alcohol, or an amine alcohol, with cysteine or a derivative thereof, which is protected on the amine function and on the thiol function by a t-butyloxycarbonyl group in the presence of dicyclohexylcarbodiimide/hydroxybenzotriazole; (2) eliminating the butyloxycarbonyl group by acidolysis; (3) adding vanadyl sulfate dissolved in water under a nitrogen atmosphere to the hydrochloride of the cysteine derivative in a dimethylformamide-borate buffer mixture at a pH of about 10, with a cysteine:vanadyl ratio of about 5:1; (4) recovering the precipitated complex; and (5) washing the recovered precipitate with water and drying the precipitate.

A second method for preparing compounds according to Formula I having one free amine group or substituted amine and carboxyl groups comprises: (1) reacting the cysteine or a derivative thereof with vanadyl sulfate at a pH of about 7.0 in water; (2) recovering the complex obtained after evaporation; (3) redissolving the complex in dimethylformamide; (4) coupling with a mono- or bifunctional amine, a mono- or bifunctional alcohol, or an amine-alcohol, in the presence of dimethylaminopropylethyl carbodiimide; and (5) recovering the complex after vacuum evaporation of the solvent, and washing the complex with ether and with water.

In general, a method for preparing the compounds of Formula XI or XV comprises: (1) reacting a monofunctional amine or a monofunctional alcohol with cysteine or a derivative thereof protected on the amine function and on the thiol function by a t-butyloxycarbonyl group in the presence of dicyclohexylcarbodiimide/ hydroxybenzotriazole; (2) eliminating the t-butyloxycarbonyl group by acidolysis with the aid of hydrochloric acid and dioxane; (3) adding vanadyl sulfate which is dissolved in water, under a nitrogen atmosphere, to the solution of the hydrochloride of the cysteine derivative in a dimethylformamide-borate buffer mixture at a pH of about 10 with a cysteine:vanadyl ratio of about 5:1; (4) stirring the mixture for 2 hours in a nitrogen atmosphere; (5) recovering the complex formed by precipitation by filtration; and (6) washing with water and drying the precipitate.

Another method for preparing the compound of Formula XI or XV comprises: (1) reacting with cysteine or a derivative thereof with vanadyl sulfate at a pH of about 7 in water; (2) recovering the complex after evaporation; (3) redissolving the complex formed in dimethylformamide as above; (4) coupling with a monofunctional amine or a monofunctional alcohol in the presence of dimethylaminopropylethylcarbodiimide; and (5) recovering the complex after vacuum evaporation of the solvent, washing with ether and with water, dissolving the product in methanol, evaporating, and reprecipitating by ethyl ether.

The preparation of the compound of XII comprises reacting a bifunctional amine or a bifunctional alcohol or an amine-alcohol with the cysteine or a derivative thereof. The remaining procedure is identical to that described above for the preparation of compounds XI and XV.

The preparation of the compound of Formula XIII where Y corresponds to a RCO- group comprises: (1) coupling an activated derivative (an ester or an acyl chloride) of the RCOOH acid with a cysteine previously protected on its thiol function by a t-butyloxycarbonyl group; (2) deprotecting the thiol function by acidolysis; and (3) complexing the resulting N-acylated derivative with the vanadyl sulfate in a DMF-water medium at a pH of 10.

A method for preparing the compound of Formula XI where Y corresponds to $RCH(CO-)_2$ comprises: (1) coupling an activated derivative (ester or acyl chloride) of the diacid $RCH(COOH)_2$ with a cysteine previously protected on its thiol function with a t-butyloxycarbonyl group; (2) deprotecting the thiol function by acidolysis; (3) reducing the N-acylated derivative thus obtained; and (4) complexing the reduced derivative in a DMF-water medium at a pH of 10 in the presence of vanadyl sulfate.

Other methods for producing coordinate-covalent complexes suitable for use in processes according to the present invention are also known in the art. For example, when the organic moiety is one of 1,10-phenanthroline, 4,7-dimethyl-1,10-phenanthroline, 3,4,7,8-tetramethyl-1,10-phenanthroline, bipyridine, oxalic acid dianion, pyridine-2-carboxylate, 5-hydroxypyridine-2-carboxylate, and pyridine-2,6-dicarboxylic acid dianion, a suitable method is dissolving $V_2O_5$ in aqueous KOH, followed by the addition of 30% hydrogen peroxide, the organic ligand, and, in some cases, ethanol to facilitate precipitation of the product.

In a typical procedure, (1,10-phenanthroline) oxodiperoxovanadium (V) (pV(phen)) can be prepared by adding $H_2O$ (30 ml) to $V_2O_5$ (2.75 g; 15 mmol) and KOH (1.95 g; 34 mmol) in a 125-ml Erlenmeyer flask followed by 1.5 ml of $H_2O_2$ (30%, w/v, solution). The mixture is then gently shaken until most of the solids dissolve (about 2 min). The brightly colored orange solution is then filtered through a sintered glass filter and is allowed to stand for 15 to 30 min. More $H_2O_2$ (30 ml) is then added to the filtrate followed almost immediately by phenanthroline (5.7 g; 32 mmol) in 25 ml of ethanol. The reaction is stirred for 30 min after which 100 ml of ethanol is added dropwise while stirring to effect precipitation of the product (4–5 g; 66–83% yield) as a fine yellow powder (B. I. Posner et al., "Peroxovanadium Compounds," *J. Biol. Chem.* 269:4596–4604 (1994)).

Similar methods can be used to prepare complexes including these organic ligands in which the metal is another metal such as molybdenum (VI) or tungsten (VI).

Other methods for preparing similar oxodiperoxovanadium (V) complexes with bidentate ligands such as oxalate or bipyridine, with various counterions, such as potassium or ammonium, are described in N. Vuletic & C. Djordjevic, "Oxodiperoxovanadate (V) Complexes with Bidentate Ligands," *J. Chem. Soc. Dalton Trans.* 1137–1141 (1973). For example, for the preparation of ammonium oxalato-oxodiperoxovanadium (V), ammonium trioxovanadate (V), $NH_4VO_3$ (0.59 g), is dissolved with cooling in hydrogen peroxide (20%, 15 ml) and added to a solution (10 ml) of ammonium oxalate (0.71 g) and hydrogen peroxide (20%). Ethanol is then added gradually until a precipitate starts to appear. The precipitate is redissolved with a small amount of hydrogen peroxide and the reaction mixture is set aside to crystallize at 5° C. The orange crystals obtained are filtered off and dried on the filter paper.

For the preparation of potassium (oxalato) oxodiperoxovanadium (V), vanadium pentoxide (0.91 g) and potassium hydroxide (1.95 g) are dissolved in water (20 ml) and to the solution oxalic acid (1.26 g) dissolved in water (10 ml) and hydrogen peroxide (30%, 20 ml) are added. Precipitation is initiated by ethanol as described above, the precipitate redissolved, and the reaction mixture set aside to crystallize at room temperature or in a cool place. The orange crystals obtained are filtered off and dried on the filter paper.

For ammonium (2,2'-bipyridine) oxodiperoxovanadium (V), ammonium trioxovanadate (V) is dissolved under cooling in hydrogen peroxide (20%, 20 ml), and 2,2'-bipyridine (0.8 g), dissolved in ethanol (10 ml), is added with stirring. After 2–3 minutes, more ethanol (20 ml) is added and the reaction mixture is set aside to crystallize at 5° C. Yellow crystals obtained are filtered off, washed once with ethanol, and dried in air.

For ammonium (1,10-phenanthroline) oxodiperoxovanadium (V), a similar preparation can be used, but the quantities of water and hydrogen peroxide are preferably reduced to half the above quantities because of the solubility properties of this complex.

For sodium (2,2'-bipyridine) oxodiperoxovanadium (V), and sodium (1,10-phenanthroline) vanadium (V), the above procedures can generally be followed. However, crystallization typically takes place more slowly for complexes with these counterions. Crystals are dried on the filter paper in air.

For potassium (2,2'-bipyridine) oxodiperoxovanadium (V), vanadium pentoxide (0.91 g) and potassium hydroxide (0.65 g) are dissolved in water (10 ml), cooled, and, if necessary, the dissolution is completed with a small amount of hydrogen peroxide. To the clear, cooled solution, hydrogen peroxide (10 ml) and 2,2'-bipyridine (1.6 g) dissolved in ethanol (7–8 ml) are added. Pure crystals are obtained as described for the analogous oxalato-derivative of potassium. Potassium (1,10-phenanthroline) vanadium (V) can be obtained similarly.

In general, other complexes can be prepared according to these methods. In some cases, the volumes or quantities of vanadium or other metal ions used can be adjusted depending on the solubility of the complex. In addition, the conditions used for the filtration and washing steps can also be varied. These variations would be known to one of ordinary skill in the art and need not be described further; they also depend on the solubility of the complexes involved.

2. Synthesis of Non-Hydrolyzable Phosphotyrosine Analogs

The nonhydrolyzable phosphotyrosine analogs, which are phosphoramidates, phosphorothioates, or phosphonates, can be synthesized by methods well understood in the art for synthesis of these compounds. Phosphorothioyltyrosine can be synthesized by sulfurization of the intermediate phosphite triester using phenylacetyl disulfide (D. B. A. Debont et al., "Solid-Phase Synthesis of O-Phosphothioylserine-Containing and O-Phosphorothreonine-Containing Peptides as Well as of O-Phosphoserine-Containing and O-Phosphothreonine-Containing Peptides," *J. Org. Chem.* 58: 1309–1317 (1993)). Phosphonates of tyrosine can be synthesized with the use of the reagent 4-[(di-t-butylphosphono)methyl]-N-(fluoren-9-ylmethoxycarbonyl)-D,L-phenylalanine (T. R. Burke et al., "Preparation of Fluoro-4-(Phosphonomethyl)-D,L-Phenylalanine and Hydroxy-4-(Phosphonomethyl)-D,L-Phenylalanine Suitably Protected for Solid-Phase Synthesis of Peptides Containing Hydrolytically Stable Analogues of O-Phosphotyrosine," *J. Org. Chem.* 58: 1336–1340 (1993)).

II. USE OF PHOSPHOTYROSINE PHOSPHATASE INHIBITORS AND TYROSINE KINASE ACTIVATORS

Phosphotyrosine phosphatase inhibitors and tyrosine kinase activators, including metal-organic coordinate covalent compounds such as vanadyl compounds and non-hydrolyzable phosphotyrosine analogs, can be used to block or alter a number of processes involving phosphotyrosine metabolism.

The exact physiological effects seen depend on whether the compound used is an inhibitor of phosphotyrosine phosphatase, an activator of tyrosine kinase, or, as in some cases, both an inhibitor of phosphotyrosine phosphatase and an activator of tyrosine kinase.

A. Use of Phosphotyrosine Phosphatase Inhibitors

1. Inhibition of Proliferation of B Cells

In B cells, the level of tyrosine phosphorylation is used for metabolic regulation. Accumulation of an excessive level of tyrosine phosphorylation, such as by the continued activity of tyrosine kinases in the absence of significant phosphotyrosine phosphatase activity, leads to apoptosis, which is programmed cell death marked by fragmentation of cellular DNA. Therefore, the administration of inhibitors of phosphotyrosine phosphatase can be used to control the proliferation of B cells. This is particularly desirable for the treatment of malignancies of B cell origin, such as leukemias and lymphomas. Such treatment also has the effect of sensitizing the cells to ionizing radiation, so that the effects of ionizing radiation and phosphotyrosine phosphatase inhibitors are not merely additive but synergistic. When both the coordinate-covalent metal-organic complex and ionizing radiation are used, the degree of cell killing induced is substantially greater than that induced by either the coordinate-covalent complex or the ionizing radiation alone.

However, phosphotyrosine phosphatase inhibitors can also be used to control proliferation of normal B cells, particularly in situations in which downregulation of the immune response is desired. Such situations include induction of immunosuppression to prevent transplant rejection, as well as in the treatment of autoimmune diseases such as rheumatoid arthritis, Hashimoto's thyroiditis, and systemic lupus erythematosus, as well as other autoimmune diseases.

Phosphotyrosine is also involved in proliferation of protozoans, such as amoebae and trypanosomes, a number of species of which are serious parasites. Accordingly, such phosphotyrosine phosphatase inhibitors can also be useful in treating protozoan-based diseases. It is predicted that the developmentally stage-specific tyrosine phosphorylation is disrupted in these organisms. This disruption is predicted to lead to death of the protozoa (M. Parsons et al., "Distinct Patterns of Tyrosine Phosphorylation During the Life Cycle of *Trypanosoma brucei,*" *Molec. Biochem. Parasitol.* 45:241–248 (1990)).

The method of inhibiting B cell proliferation comprises the step of contacting proliferating B cells with a phosphotyrosine phosphatase inhibitor as described above. The compound is administered in a quantity sufficient to detectably inhibit proliferation of the cells as measured by incorporation of nucleotides into DNA. The term "detectably inhibit proliferation," as used herein, refers to a detectable decrease in either DNA synthesis or cell number, inasmuch as cell division follows DNA synthesis. Typically, the dose required is in the range of 1 $\mu$M to 100 $\mu$M, more typically in the range of 5 $\mu$M to 25 $\mu$M. The exact dose required can be readily determined from in vitro cultures of the cell and exposure of the cells to varying dosages of the phosphotyrosine phosphatase inhibitor. The effect of the phosphotyrosine phosphatase inhibitor, or other treatments such as radiation, can be judged by clonogenic assays, assays measuring the incorporation of radioactively labeled nucleotides into DNA, or other assays measuring cell proliferation.

For this and other treatment methods that are aspects of the present invention, one of ordinary skill in the art could determine effective dosages and other treatment modalities by animal studies. This approach is described in D. J. Brusick, "The Use of Short Term In Vitro and Submammalian Tests as Alternatives to Large Scale Animal Bioassays," in *The Role of Animals in Biomedical Research* (J. A. Sechzer, ed., New York Academy of Sciences, New York, N.Y., 1983 (Annals of the New York Academy of Sciences, vol. 406)), pp. 68–73, as well as in M. D. Rawlins, "What Is Expected from Repeated-Dose Studies by Clinical Pharmacologists," in *Long-Term Animal Studies: Their Predictive Value for Man* (S. R. Walker & A. D. Dayan, eds., MTP Press Ltd., Lancaster, 1986), pp. 13–22. Other approaches for determination of effective or optimal dosages and treatment modalities, such as the use of cell or tissue culture and mathematical modeling, are known to those of ordinary skill in the art.

2. Treatment Of Lymphoproliferative Disorders

Because of the effect of phosphotyrosine phosphatase inhibitors on proliferation of cells, particularly B cells, but also myeloid cells, such inhibitors can be used in a method of treating malignant proliferative disorders. The diseases that can be treated include leukemias and lymphomas, and the proliferating cells can be either B cells, or, alternatively, myeloid cells. The method comprises the step of contacting the proliferating malignant cells with a phosphotyrosine phosphatase inhibitor as described above. The compound is administered in a quantity sufficient to significantly inhibit proliferation of the malignantly proliferating cells, as that term is defined above. The dosage range in general is as described above. Further guidance for the dosage is given in the Examples below.

The compositions can be administered using conventional modes of administration including, but not limited to, intravenous, intraperitoneal, oral, or intralymphatic. Other routes of injection can alternatively be used. Oral or intraperitoneal administration is generally preferred. The composition can be administered in a variety of dosage forms which include, but are not limited to, liquid solutions or suspensions, tablets, pills, powders, suppositories, polymeric microcapsules or microvesicles, liposomes, and injectable or infusible solutions. The preferred form depends on the mode of administration and a quantity administered.

The compositions for administration including the phosphotyrosine phosphatase inhibitors preferably also include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate. The most effective mode of administration and dosage regimen for the phosphotyrosine phosphatase inhibitors as used in the methods of the present invention depend on the severity and course of the disease, the patient's health, the response to treatment, the particular type of malignantly proliferating cells characteristic of the particular leukemia or lymphoma, pharmacokinetic considerations such as the condition of the patient's liver and/or kidneys that can affect the metabolism and/or excretion of the administered phosphotyrosine phosphatase inhibitors, and the judgment of the treating physician. Accordingly, the dosages should be titrated to the original patient. Nevertheless, an effective dose of the phosphotyrosine phosphatase inhibitors for use in the treatment methods of the present invention can be in the range from about 1 $\mu$M to about 100 $\mu$M in the blood and/or tissues.

Preferably, the dose of phosphotyrosine phosphatase inhibitor used is sufficient to induce apoptosis in the malignantly proliferating cells.

The treatment method can further comprise a step of delivering ionizing radiation to the cells contacted with the phosphotyrosine phosphatase inhibitor. The ionizing radiation is delivered in a dose sufficient to induce a substantial degree of cell killing among the malignantly proliferating cells, as judged by assays measuring viable malignant cells. The degree of cell killing induced is substantially greater than that induced by either the phosphotyrosine phosphatase inhibitor alone or the ionizing radiation alone. Typical forms of ionizing radiation include beta rays, gamma rays, alpha particles, and X-rays. These can be delivered from an outside source, such as X-ray machine or a gamma camera, or delivered to the malignant tissue from radionuclides administered to the patient. The use of radionuclides is well understood in the art and need not be detailed further. The use of ionizing radiation in the treatment of malignancies is described, for example, in S. Hellman, "Principles of Radiation Therapy" in *Cancer: Principles & Practice of Oncology* (V. T. DeVita, Jr., S. Hellman, & S. A. Rosenberg, eds., 4th ed., 1993, J. B. Lippincott Co., Philadelphia), ch. 15, pp. 248–275.

A range of dosages that can be used is between about 1 and 500 cGy (i.e., from about 1 to about 500 rads).

When phosphotyrosine phosphatase inhibitors according to the present invention are used along with ionizing radiation, typically, the dose of the phosphotyrosine phosphatase inhibitor used is equal to or less than the dose that would be used if the phosphotyrosine phosphatase inhibitor were used alone.

3. Inhibition of Phosphotyrosine Phosphatases

Methods according to the present invention can also be used to inhibit phosphotyrosine phosphatases for purposes other than that of treating malignant disease.

In particular, phosphotyrosine phosphatase inhibitors can be used to suppress the immune system in order to prevent organ and tissue rejection during transplantation and also in the treatment of autoimmune diseases such as rheumatoid arthritis, Hashimoto's thyroiditis, systemic lupus erythematosus, Guillain-Barre Syndrome, and possibly multiple sclerosis.

Methods according to the present invention can also be used in the treatment of protozoan infections, such as amoebae and trypanosomes, whose proliferation also depends on phosphorylation.

Additionally, methods according to the present invention can be useful in the studies of B cells in culture, in order determine their susceptibility to ionizing radiation and other reagents, such as alkylating agents and intercalating agents that can interfere with DNA synthesis, and can be used to screen reagents for their activity to interfere with DNA synthesis. In particular, methods according to the present invention can be used to block B cell development in vitro in order to determine the effect of inhibition of proliferation of B cells on development of immune responses. For example, such methods could be used to augment signals and enhance calcium levels in cells (see Example 8). Such methods can also be used to block the effects of CD28. Accordingly, such methods can therefore be used to screen B cell cultures for abnormal UV-induced signals. Such screening could be clinically useful in determining susceptibility to conditions related to ultraviolet exposure, such as skin cancer. This may be particularly useful in studying conditions linked to abnormal ultraviolet sensitivity. Such conditions include Bloom's Syndrome and xeroderma pigmentosum.

4. Prevention of Class-Switching in Antibodies

Methods according to the present invention can further be used to prevent class-switching in antibodies from Ig or IgM to IgE. It is desirable to block IgE production because this type of antibody mediates many allergic responses, particularly immediate-type hypersensitivity reactions such as anaphylaxis, atopy, and urticaria. The CD40 ligand gp39 and the cytokine IL-4 act on B cells to induce the switching of the type of antibody produced from IgM to IgE. CD40 and IL-4 mechanisms of action are known to involve tyrosine phosphorylation. Phosphotyrosine phosphatase inhibitors such as BMLOV disrupt the normal pattern of tyrosine phosphorylation, thus disrupting the class-switching process. The administration of BMLOV, in particular, can markedly inhibit the production of IgE antibody while much less markedly inhibiting the production of IgG subclasses such as IgG1 and IgG4. This leads to the result that the ratio of IgG to IgE increases (Example 14). These results lead to the conclusion that phosphotyrosine phosphatase inhibitors such as BMLOV have value in the treatment of allergy.

Accordingly, a method of preventing the class-switching of antibody-producing cells comprises administering to antibody-producing cells a quantity of a phosphotyrosine phosphatase inhibitor sufficient to detectably reduce the production of IgE antibody by the cells. Typically, the cells also produce IgG antibody, and the quantity of the phosphotyrosine phosphatase inhibitor is such that the ratio of the quantity of IgG antibody produced by the cells to the quantity of IgE antibody produced by the cells increases.

Any of the phosphotyrosine phosphatase inhibitors disclosed above can be used to prevent class-switching, including metal-organic coordinate-covalent compounds, non-hydrolyzable phosphotyrosine analogs, dephostatin, and 4-(fluoromethyl) phenyl phosphate and its esterified derivatives. However, a preferred phosphotyrosine phosphatase inhibitor for preventing class-switching is BMLOV.

5. Purgation of Bone Marrow for Autologous Transplantation

Another use for phosphotyrosine phosphatase inhibitors according to the present invention is in purging bone marrow in preparation for autologous transplantation following whole body irradiation and/or chemotherapy. This type of therapy is often attempted for multiple myeloma, which is a B cell malignancy. Thus, reagents that inhibit replication of B cells, such as phosphotyrosine phosphatase inhibitors according to the present invention, would be expected to inhibit growth of the residual B cells present in bone marrow and assist in purging bone marrow prior to autologous transplantation.

6. Stimulation of $Ca^{2+}$ Signaling in T Cells

As shown below in Example 19, phosphotyrosine phosphatase inhibitors according to the present invention, particularly BMLOV, can be used to stimulate $Ca^{2+}$ signaling in T cells without inducing apoptosis. BMLOV enhanced productive T cell responses, including increased IL-2 receptor expression, after stimulation of the T cell antigen receptor (Example 19). Therfore, such inhibitors can be used to activate these cells by appropriate adjustment of the dosage; 25 μM BMLOV detectably stimulated $Ca^{2+}$ signaling. This provides lineage-specific effects.

B. Use of Reagents That Stimulate Tyrosine Kinases

Because the degree of phosphotyrosine phosphorylation in cells can be affected either by inhibition of phosphotyrosine phosphatase or the stimulation of tyrosine kinase, methods according to the present invention can also be practiced with reagents that either stimulate tyrosine kinases, or both inhibit phosphotyrosine phosphatase and stimulate tyrosine kinases.

Typically, reagents in this category are coordinate-covalent complexes comprising: (1) a metal ion selected from the group consisting of molybdenum (VI), vanadium (V), or tungsten (VI); (2) at least one oxo group coordinate-covalently bound to the metal ions; (3) at least one organic moiety coordinate-covalently bound to the metal ion through at least one N-containing, O-containing or As-containing moiety capable of donating electrons to a coordinate-covalent bond; and (4) optionally, one or two peroxo groups coordinate-covalently bound to the metal ion, each occupying two sites in the coordination sphere of the metal ion.

The coordinate-covalent complex has an affinity for the active site of a phosphotyrosine phosphatase sufficient to detectably inhibit the activity of one or more phosphotyrosine phosphatases. Preferably, the coordinate-covalent complex has an affinity for the active site of phosphotyrosine phosphatase at least about equal to the affinity of bis (maltolato) oxovanadium (IV) for the active site of phosphotyrosine phosphatase.

Preferably, a coordinate-covalent complex possessing both phosphotyrosine phosphatase inhibiting and tyrosine kinase stimulating activity comprises: (1) a metal ion selected from the group consisting of molybdenum (VI), tungsten (VI), and vanadium (V); (2) an oxo group coordinate-covalently bound to the metal ion; (3) at least one peroxo group coordinate-covalently bound to the metal ion; and (4) at least one organic moiety coordinate-covalently bound to the metal ion through at least one N-containing or O-containing functional group capable of donating electrons to a coordinate-covalent bond.

In one particularly preferred class of compounds that affect both tyrosine kinase and phosphotyrosine phosphatase activity, the metal ion is vanadium. When the metal ion is vanadium, the coordinate-covalent complex preferably has two peroxo groups bound to the metal ion, but can, alternatively, have one peroxo group bound to the metal ion. When the complex has two peroxo groups bound to the metal ion, particularly preferred coordinate-covalent complexes include, but are not limited to, (1,10-phenanthroline) oxodiperoxovanadium (V), oxalato-oxodiperoxovanadium (V), (2,2'-bipyridine) oxodiperoxovanadium (V), (4,7-dimethyl-1,10-phenanthroline) oxodiperoxovanadium (V), (3,4,7,8-tetramethyl-1,10-phenanthroline) oxodiperoxovanadium (V), (pyridine-2-carboxylic acid) oxodiperoxovanadium (V), (5-hydroxypyridine-2-carboxylic acid) oxodiperoxovanadium (V), (pyridine-2,6-dicarboxylic acid) oxodiperoxovanadium (V), and derivatives thereof possessing substantially equivalent affinity for the active site of phosphotyrosine phosphatase.

A particularly preferred vanadium-containing coordinate-covalent complex is (1,10-phenanthroline) oxodiperoxovanadium (V).

When the metal is vanadium and the coordinate-covalent complex has one peroxo group bound to the metal ion, a preferred coordinate-covalent complex is (pyridine-2,6-dicarboxylato) (hydrato) oxoperoxovanadium (V).

Alternatively, the metal ion in the coordinate-covalent complex can be molybdenum (VI). The coordinate-covalent complex can have one or two peroxo groups bound to the metal ion when molybdenum is the metal ion. When the coordinate-covalent complex has two peroxo groups bound to the metal ion, preferred coordinate-covalent complexes with molybdenum (VI) as the metal ion include, but are not necessarily limited to, bis(dimethylformamido) oxodiperoxomolybdenum (VI) and hydrogen (pyridine-2-carboxylato) oxodiperoxomolybdenum (VI) hydrate.

When the metal ion is molybdenum, and the coordinate-covalent complex has one peroxo group bound to the metal ion, preferred coordinate-covalent complexes include, but are not necessarily limited to, [(N-salicylidene)-2-hydroxybenzeneamine] [ethanol] oxoperoxomolybdenum (VI), (pyridine-2,6-dicarboxylato) (hydrato) oxodiperoxomolybdenum (VI), and bis(N-phenylbenzohydroxamato) oxodiperoxomolybdenum (VI).

Alternatively, a coordinate-covalent complex suitable for the processes of the present invention can comprise: (1) a metal ion selected from the group consisting of molybdenum (VI), tungsten (VI), and vanadium (V); (2) an oxo group coordinate-covalently bound to the metal ion; and (3) at least one organic moiety coordinate-covalently bound to the metal ion through at least one N-containing or O-containing moiety capable of donating electrons to a coordinate-covalent bond. The coordinate-covalent complex has an affinity for the active site of a phosphotyrosine phosphatase sufficient to detectably inhibit the activity of one or more phosphotyrosine phosphatases. Preferably, the coordinate-covalent complex has an affinity for the active site of phosphotyrosine phosphatase at least about equal to the affinity of bis(maltolato) oxovanadium (IV) for the active site of phosphotyrosine phosphatase.

When the metal ion is molybdenum, a particularly preferred coordinate-covalent complex is bis(benzene-1,2-di [dimethylarsino)] [chloro] oxomolybdenum (VI). When the metal ion is vanadium, preferred coordinate-covalent complexes include, but are not necessarily limited to, meso-tartrato oxovanadium (V).

In addition to the particular coordinate-covalent complexes disclosed above, other coordinate-covalent complexes can be used for the processes of the present invention. These include derivatives of these complexes substituted with hydroxy or lower alkyl ($C_1$–$C_5$) substituents that do not interfere with the formation of coordinate-covalent bonds.

Typically, the coordinate-covalent complexes are salts in which the coordinate-covalent complex is an anion; in these salts, the cation can be sodium, potassium, ammonium, a quaternary ammonium, or another cation with a +1 charge.

In particular, (1,10-phenanthroline) oxodiperoxovanadium (V), known as pV(phen), activates at least one type of tyrosine kinase, the Syk family kinases. Compounds described herein are believed to share this activation activity. Although Applicant is not bound by this theory, it is believed that pV(phen) causes relative lymphopenia or depletion of lymphocytes in the blood and also causes substantial neutrophilia, or increase in neutrophils. This is significant because most cytotoxic anti-cancer drugs cause neutropenia, a diminution of neutrophils which is a severe problem and a serious side effect of many cytotoxic drugs in patients administered such drugs.

In contrast to the compounds described above in Section A, the ability of pV(phen) to induce tyrosine phosphorylation in both T and B cells correlates with its biological effects on both cell types. This is in contrast to BMLOV (Example 4), which induces tyrosine phosphorylation in B cells much more than in T cells and which has much more potent biological effects on B cells than on T cells.

Accordingly, these compounds can inhibit proliferation of cell types including B cells, T cells, and cells derived from malignant transformation of B cells or T cells.

Methods of inhibiting proliferation of these cell types can be used to treat a subject suffering from a malignant proliferative disorder wherein the proliferating malignant cells are B cells, T cells, cells derived from malignant transformation of B cells or T cells, or myeloid cells. These methods can be combined with the use of ionizing radiation as described above. The degree of cell killing induced by the combination of the metal-containing coordinate-covalent complex and ionizing radiation is preferably substantially greater than that induced by either the coordinate-covalent complex or the ionizing radiation alone.

These coordinate-covalent compounds can also be used to prevent the class-switching of antibody-producing cells, as described above.

More generally, these metal-containing coordinate-covalent complexes can be used in a method of inducing tyrosine phosphorylation in a cell type selected from the group consisting of B cells, T cells, and cells derived from malignant transformation of B cells or T cells.

One particular application of these methods according to their present invention is in treating tumors, both tumors derived from B cells or T cells, such as leukemias or lymphomas, and solid tumors of other origins such as melanomas (Example 17, infra). Tumors susceptible to treatment by these methods include tumors comprised of tumor cells overexpressing one or more members of the EGF receptor family (HER1, HER2 or neu, HER3, and HER4), other receptor tyrosine kinases (RPTK) or other tyrosine kinases (PTK) such as, but not limited to, Src. These phosphotyrosine phosphatase inhibitors and/or tyrosine kinase activators, such as pV(phen), are likely to selectively kill tumor cells that express RPTK such as HER2. Tumors susceptible to treatment by these methods also include tumors comprised of tumor cells requiring phosphotyrosine phosphatase for their growth and/or survival. An example of this latter type of tumor cells is melanoma cells, which, although not known to overexpress tyrosine kinases, are nevertheless sensitive in vivo to pV(phen) (Example 17, infra).

Numerous published papers have reported the desirability of using tyrosine kinase inhibitors to block signals from RPTK such as HER2 in tumor cells. The use of PTP inhibitors is the opposite of this widely held concept because it would instead greatly increase the signal. This concept is highly relevant to cancer treatment because RPTK such as HER2 are overexpressed in a variety of cancers, notably breast and ovarian cancers, as well as other cancers. Furthermore, the overexpression of HER2 has been shown to be an indicator of poor prognosis in patients, in that tumors frequently resist all known therapies. Therefore, treatments with PTP inhibitors using processes according to the present invention would thus affect the tumors with the worst prognosis.

Overexpression of these kinases can be determined by assay of the kinases in culture and comparison to cells not of malignant origin.

III. PREPARATION AND USE OF CONJUGATES OF PHOSPHOTYROSINE PHOSPHATASE INHIBITORS OR TYROSINE KINASE ACTIVATORS WITH SPECIFIC BINDING PARTNERS

Another aspect of the present invention is a conjugate of a phosphotyrosine phosphatase inhibitor or a tyrosine kinase activator with a specific binding partner to target the phosphotyrosine phosphatase inhibitor or the tyrosine kinase activator to the appropriate cellular target. The term "modulator of phosphotyrosine metabolism" is used generically herein to refer to both inhibitors of phosphotyrosine phosphatase and activators of tyrosine kinase. The term "specific binding partner" is used generically herein to refer to a member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor. As used herein as examples of specific binding partners, the term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits. Both polyclonal and monoclonal antibodies are included unless otherwise specified. However, in most applications, it is generally preferred to use monoclonal antibodies.

Particularly useful specific binding partners are those that bind specifically to B cells, particularly abnormal B cells. An example of these specific binding partners is anti-CD19 monoclonal antibody.

The CD19 molecule is a B-lineage specific surface receptor that is expressed on the surface of leukemia cells from 85% of patients with acute lymphoblastic leukemia (ALL). It is absent from parenchymal cells of nonhematopoetic organs, circulating blood myeloid and erythroid cells, T cells, and bone marrow stem cells (F. M. Uckun et al., *J. Exp. Med.* 163:347 (1986); I. Stamenkovic & B. Seed, *J. Exp. Med.* 168:1205 (1988); F. M. Uckun et al., *Blood* 71:13 (1988); T. F. Tedder & C. M. Isaacs, *J. Immunol.* 143:712 (1989); F. M. Uckun & J. A. Ledbetter, *Proc. Natl. Acad. Sci.*

USA 85:8603 (1988); J. A. Ledbetter et al., *Proc. Natl. Acad. Sci. USA* 85:1897 (1988); F. M. Uckun et al., *Proc. Natl. Acad. Sci. USA* 88:3589 (1991)), thus providing an opportunity to target the conjugate to the appropriate cells and reducing the opportunity for non-specific toxicity. $CD19^+$ ALLs are believed to originate from putative developmental lesions in normal B cells precursor (BCP) clones during early phases of ontogeny and are therefore classified as BCP leukemias (M. F. Greaves, *Science* 234:697 (1986); M. F. Greaves, *Blood* 82:1043 (1993); F. M. Uckun et al., *New Engl. J. Med.* 329:1296 (1993); G. K. Rivera et al., *New Engl. J. Med.* 329:1289 (1993); L. M. Nadler et al., *J. Immunol.* 131:244 (1983); F. M. Uckun, *Blood* 76:1908 (1990); F. M. Uckun et al., *Blood* 79:3369 (1992)). CD19 is found on the surface of each BCP leukemia cell at a high density (>50,000 molecules per cell) and shows a high affinity for the monoclonal antibody (mAb) B43 (anti-CD19) ($K_a < 10^8$ $M^{-1}$) (F. M. Uckun et., *J. Exp. Med.* 163:347 (1986)); I. Stamenkovic & B. Seed (1988), supra, F. Uckun et al., *Blood* 71:13 (1988); T. F. Tedder & C. M. Isaacs (1989), supra).

Alternatively, monoclonal antibodies to other CD antigens or other B-cell-specific antigens can be used. Among the B-cell-specific antigens for which specific monoclonal antibodies can be used to target the conjugates to B cells are CD10, CD20, CD21, CD22, CD24, CD37, CD40, CDw75, CDw78, and B7. Other antigens are also known and are described, for example, in A. N. Barclay et al., "The Leucocyte Antigen Facts Book" (Academic Press, London, 1993).

Conjugation methods are also well known in the art for conjugating a phosphotyrosine phosphatase inhibitor or a tyrosine kinase activator to a specific binding partner. For the metal-organic compounds described above, the specific binding partner is conjugated to the organic moiety of the metal-organic compound. The organic moiety either has a functional group that can be conjugated, or can be substituted with such a group. Examples of such functional groups suitable for conjugation include hydroxyl groups, aldehyde or keto groups, and carboxylic acid groups. Techniques for conjugation of specific binding partners, typically proteins, to such groups are described, for example in P. Tijssen, "Practice and Theory of Enzyme Immunoassays" (Elsevier, Amsterdam, 1985, pp. 283–289, in S. S. Wong, "Chemistry of Protein Conjugation and Crosslinking" (CRC Press, Boca Raton, Florida, 1991), and in T. E. Creighton, ed., "Protein Function: A Practical Approach" (IRL Press, Oxford, 1989).

For example, organic moieties containing carboxyl groups or that can be carboxylated can be conjugated to proteins via the mixed anhydride method, the carbodiimide method, using dicyclohexylcarbodiimide, and the N-hydroxysuccinimide ester method.

If the organic moiety contains amino groups or reducible nitro groups or can be substituted with such groups, conjugation can be achieved by one of several techniques. Aromatic amines can be converted to diazonium salts by the slow addition of nitrous acid and then reacted with proteins at a pH of about 9. If the organic moiety contains aliphatic amines, such groups can be conjugated to proteins by various methods, including carbodiimide, tolylene-2,4-diisocyanate, or malemide compounds, particularly the N-hydroxysuccinimide esters of malemide derivatives. An example of such a compound is 4-(N-maleimidomethyl)-cyclohexane-1-carboxylic acid. Another example is m-maleimidobenzoyl-N-hydroxysuccinimide ester. Still another reagent that can be used is N-succinimidyl-3-(2-pyridyldithio) propionate. Also, bifunctional esters, such as dimethylpimelimidate, dimethyladipimidate, or dimethylsuberimidate, can be used to couple amino-group-containing moieties to proteins.

Additionally, aliphatic amines can also be converted to aromatic amines by reaction with p-nitrobenzoylchloride and subsequent reduction to a p-aminobenzoylamide, which can then be coupled to proteins after diazotization.

Organic moieties containing hydroxyl groups can be cross-linked by a number of indirect procedures. For example, the conversion of an alcohol moiety to the half ester of succinic acid (hemisuccinate) introduces a carboxyl group available for conjugation. The bifunctional reagent sebacoyldichloride converts alcohol to acid chloride which, at pH 8.5, reacts readily with proteins. Hydroxyl-containing organic moieties can also be conjugated through the highly reactive chlorocarbonates, prepared with an equal molar amount of phosgene.

For organic moieties containing ketones or aldehydes, such carbonyl-containing groups can be derivatized into carboxyl groups through the formation of O-(carboxymethyl) oximes. Ketone groups can also be derivatized with p-hydrazinobenzoic acid to produce carboxyl groups that can be conjugated to the specific binding partner as described above. Organic moieties containing aldehyde groups can be directly conjugated through the formation of Schiff bases which are then stabilized by a reduction with sodium borohydride.

One particularly useful cross-linking agent for hydroxyl-containing organic moieties is a photosensitive noncleavable heterobifunctional cross-linking reagent, sulfosuccinimidyl 6-[4'-azido-2'-nitrophenylamino] hexanoate. Other similar reagents are described in S. S. Wong, "Chemistry of Protein Conjugation and Cross-Linking," supra.

Other cross-linking reagents can be used that introduce spacers between the organic moiety and the specific binding partner.

The invention is illustrated by the following Examples. The Examples are for illustrative purposes only and are not intended to limit the invention.

EXAMPLES

EXAMPLE 1

Inhibition of Phosphotyrosine Phosphatases by Bis (Maltolato)Oxovanadium (IV) (BMLOV)

Bis(maltolato)oxovanadium (IV) (BMLOV) was synthesized as described in J. H. McNeill et al., "Bis(maltolato) oxovanadium (IV) is a Potent Insulin Mimic," *J. Med. Chem.* 35:1489–1491 (1992). Briefly, the compound was synthesized by combining maltol (3-hydroxy-2-methyl-4-pyrone) and vanadyl sulfate in a 2:1 ratio in water. The pH of the solution was raised to 8.5, and the solution was refluxed overnight. A deep purple-green birefringent compound precipitated on cooling and was collected. This compound is the BMLOV.

BMLOV was then assayed for its activity in inhibiting several phosphatases, including phosphotyrosine phosphatases PTP1B and CD45, as well as serine/threonine phosphatases PP1 and PP2A and calf intestinal alkaline phosphatase.

The tyrosine phosphatases PTP1B and CD45 were assayed with phosphorylated myelin basic protein as described in K. Guan et al., *Nature* 350:359–362 (1991) except that 2-minute assays were performed. The PTP1B used was a GST fusion protein (Upstate Biotechnology, Lake Placid, N.Y.). The CD45 was immunoprecipitated from Jurkat T cells with the monoclonal antibody 9.4 (ATCC No. HB 10270, deposited with the American Type Culture Collection, Rockville, Md., on Oct. 20, 1989). The phosphatases PP1 and PP2A (Upstate Biotechnology) and calf intestinal alkaline phosphatase (Sigma, St. Louis, Mo.) were assayed with p-nitrophenyl phosphate as a substrate.

The results are shown in Table 1.

TABLE 1

Phosphatase Inhibition by BMLOV

| Phosphatase | $IC_{50}$, NM | SEM | n |
|---|---|---|---|
| PTP1B | 26 | 7 | 3 |
| CD45 | 25 | 1 | 3 |
| PP1 | 6156 | 360 | 2 |
| PP2A | 3337 | 208 | 2 |
| Alkaline Phosphatase | $>5 \times 10^5$ | — | 2 |

BMLOV was found to be a potent inhibitor of PTP1B and CD45, both of which are phosphotyrosine phosphatases. The drug showed substantial selectivity for the phosphotyrosine phosphatases relative to other phosphatases. Much higher concentrations of the drug were required to inhibit the serine phosphatases PP1 and PP2A. Intestinal alkaline phosphatase was highly resistant to inhibition by BMLOV.

EXAMPLE 2

Induction of Tyrosine Phosphorylation in Transformed Lymphocytes

Ramos cells, a human B cell lymphoma cell line, were treated with varying doses of BMLOV. The cells were lysed and lysates were subjected to polyacrylamide gel electrophoresis in the presence of sodium dodecyl sulfate (SDS-PAGE). The resulting electropherograms were subjected to Western blotting with anti-phosphotyrosine antibody to detect the presence of phosphotyrosine in the cells.

The results are shown in FIGS. 1A–1C. FIG. 1A demonstrates that BMLOV induces tyrosine phosphorylation in a dose-dependent manner when the cells were treated with varying doses for a period of 1 hour. FIG. 1B shows the effects of treating cells with 100 $\mu$M BMLOV for varying times. The drug was found to begin to induce tyrosine phosphorylation in the cells by 8 minutes and the phosphorylation increased with further exposure.

FIG. 1C demonstrates that treatment of the cells for 16 hours with 50 $\mu$M BMLOV leads to high levels of tyrosine phosphorylation.

EXAMPLE 3

Induction of Apoptosis by BMLOV

Figure 2A:
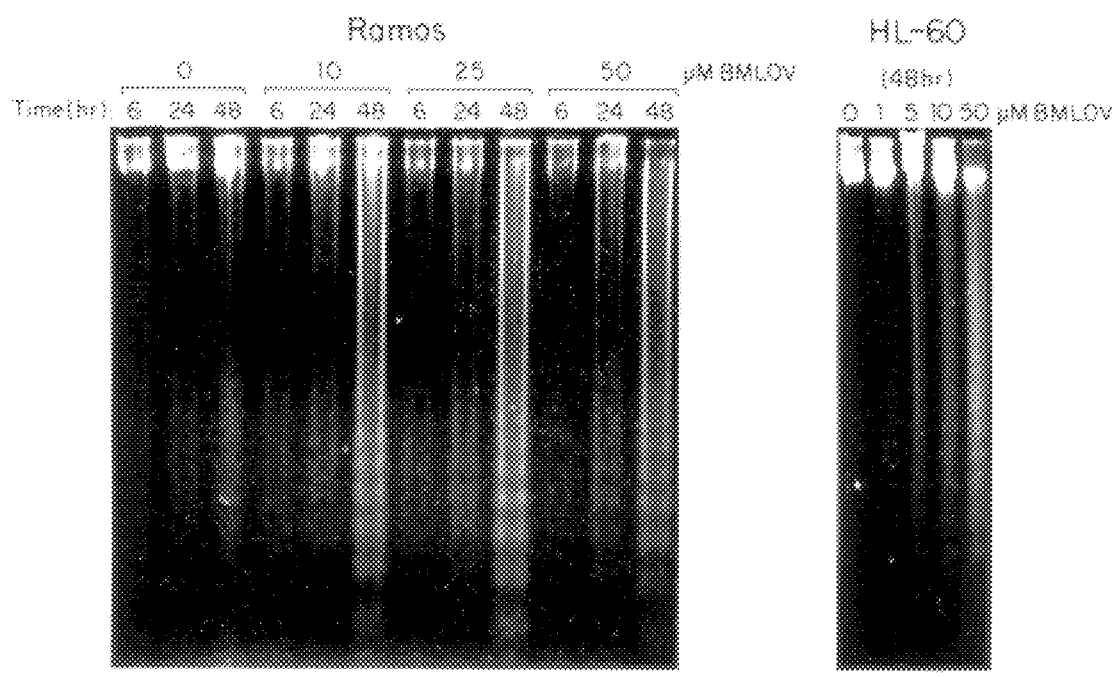
FIG. 2A is a photograph of a stained electropherogram of an agarose gel of DNA from Ramos cells and human promyelocytic leukemia HL-60 cells after treatment of the cells with BMLOV, showing the breakdown of the DNA into fragments characteristic of apoptosis.

BMLOV was demonstrated to kill malignant leukemia and lymphoma cells by inducing apoptosis. Apoptosis is the process of programmed cell death. The hallmark of apoptosis is the fragmentation of DNA into fragments whose size distribution is observed as a ladder of bands on agarose gels. FIG. 2A demonstrates that BMLOV induced apoptosis in Ramos B cell lymphoma cells by 48 hours at a dose of 10 $\mu$M, with apoptosis apparent at 24 hours with higher doses. Apoptosis was also observed to be induced in the human acute promyelocytic leukemia cell line HL60 in a dose dependent manner (FIG. 2A). The induction of apoptosis was specific in that apoptosis was not observed in the human T-cell leukemia cell lines CEM or Jurkat, nor was it observed in the human colon carcinoma cell line 3347 (FIG. 2B).

For these experiments, cell samples ($2 \times 10^6$ cells) were centrifuged at 200× g, the media removed by aspiration and the cell pellets stored at $-70°$ C. until processing. Cell pellets were resuspended in 300 $\mu$l digestion buffer (100 mM NaCl, 10 mM Tris-HCl, pH 8.0, 25 mM EDTA, 0.5% SDS, 0.1 mg/ml protease K) and incubated for 12 hours at 50° C. DNase-free ribonuclease (5 $\mu$g) in 200 $\mu$l TE buffer (10 mM Tris-HCl, pH 7.5, 1 mM EDTA) was added to each sample followed by incubation for 2 hours at 37° C. DNA was then extracted once with phenol:chloroform, once with chloroform and then precipitated with 0.5 volumes of ammonium acetate and 2 volumes of ethanol at $-70°$ C. for 12 hours. The precipitated DNA was resuspended in 200 $\mu$l TE buffer and quantitated by absorbance at 260 nanometers. The DNA (15 $\mu$g) was applied to a 1.3% agarose gel in TBE buffer (89 mM Tris base, 89 mM boric acid, 2 mM EDTA) resolved at 20 mA constant current and the DNA was visualized by staining with ethidium bromide. Fragmented DNA due to apoptosis appeared as a ladder of bands on the gel.

EXAMPLE 4

Selective Cytotoxicity of BMLOV as Examined in Clonogenic Assays

The selective cytotoxicity of BMLOV was examined in clonogenic assays. Cells were grown in methylcellulose media and the number of colonies formed after seven days of treatment with various doses of the drug were determined. The clonogenic assays were performed with six replicates for each treatment as described [F. M. Uckun et al., *J. Exp. Med.* 163:347–368 (1986); F. M. Uckun & J. A. Ledbetter, *Proc. Natl. Acad. Sci. USA* 85:8603–8607 (1988)). The data is given plus/minus the standard error of the mean.

The data is shown in Table 2. The three B-cell lines, Ramos, Raji, and REH, were all highly sensitive to doses of 5 to 10 $\mu$M BMLOV. The myeloid cell line THP-1 and the promyelocytic cell line HL-60 also were highly sensitive to BMLOV at a dose of only 1 $\mu$M. BMLOV gave 99.8% clonogenic cell death for the Raji transformed B cell line at a dose of 10 $\mu$M, and 99.4% clonogenic cell death for HL-60 promyelocytic leukemia cells at 1 $\mu$M.

TABLE 2

Inhibition of Leukemia and Lymphoma Cell Line Growth
by BMLOV as Measured in Clonogenic Assays

| Dose, µM | Cell Line | | | | |
|---|---|---|---|---|---|
| | Ramos | Raji | REH | THP-1 | HL-60 |
| 0 | 4065 ± 840 | 3252 ± 672 | 5122 ± 1296 | 6453 ± 1563 | 5122 ± 1241 |
| 1.0 | 179 ± 33 (95.6%) | 1291 ± 283 (60.3%) | 1810 ± 385 (64.7%) | 1613 ± 235 (75.0%) | 31 ± 8 (99.4%) |
| 5.0 | 7 ± 2 (99.8%) | 4 ± 0.6 (99.9%) | 71 ± 8 (98.6%) | 127 ± 35 (98.0%) | 31 ± 8 (99.4%) |
| 10.0 | 0 | 3 ± 0.8 (99.9%) | 8 ± 1 (99.8%) | 127 ± 35 (98.0%) | 15 ± 4 (99.7%) |

Data is given in colonies per $10^4$ cells; the percentage of inhibition is shown in parentheses.

By contrast, the T cell line CEM or MDAMB-453 breast carcinoma cells were inhibited only moderately by a dose as high as 100 µM of BMLOV.

EXAMPLE 5

The Effect of BMLOV on Incorporation of Nucleotides into DNA

In order to determine the effects of BMLOV on various cell types, including a number of cell types that did not grow well in the methylcellulose clonogenic assay, the cells were grown for seven days in the presence of BMLOV. For each cell type, the cells were passaged uniformly for all drug doses given during the seven-day period. The cells were then pulsed for six hours with [$^3$H]thymidine. The extent of DNA synthesis was then determined by counting the radioactivity incorporated into the cells. The data is shown in Table 3.

TABLE 3

Inhibition of Leukemia and Lymphoma Cell Line Growth
by BMLOV as Measured in Thymidine Incorporation Assays

| Dose, µM | [$^3$H] cpm Incorporation for Cell Line: | | | | | | |
|---|---|---|---|---|---|---|---|
| | Ramos | BCL$_1$ | A20 | THP-1 | HL-60 | Jurkat | CEM |
| 0 | 292342 | 271144 | 389480 | 202301 | 249183 | 143917 | 395157 |
| 1 | 289936 | 265036 | 419947 | 201670 | 191637 | 149950 | 368721 |
| 5 | 65545 | 226714 | 289932 | 178290 | 276505 | 118720 | 403576 |
| 10 | 167 | 55396 | 66157 | 199993 | 222178 | 98057 | 371256 |
| 25 | 149 | 195 | 281 | 112209 | 11398 | 26511 | 313714 |

Ramos cells were highly sensitive to doses of 10 and 25 µm BMLOV. The murine cell line BCL$_1$ is a highly tumororigenic and lethal leukemia considered to be a model of human chronic lymphocytic leukemia (CLL). These cells were highly sensitive to the drug at a dose of 25 µM. THP-1 cells showed only partial sensitivity to the drug at a dose of 25 µM. In general, cells were more sensitive to the drug in the clonogenic assays than in the thymidine incorporation assay. These results suggest a greater requirement for phosphatase activity for cells to grow as colonies in methylcellulose relative to growth in free suspension in liquid media. The murine B cell lymphoma line A20, which forms highly aggressive tumors in mice, was very sensitive to a dose of 25 µM of the drug. The human promyelocytic leukemia cell line HL60 and the human acute T cell leukemia cell line Jurkat were moderately sensitive to BMLOV at a dose of 25 µM, whereas the human T cell acute lymphocytic leukemia CEM was resistant. These results indicate that malignant cells of B cell origin, including lymphoma, acute lymphocytic leukemia, and chronic lymphocytic leukemia are sensitive to BMLOV. Some leukemias of myeloid and T cell origin also show sensitivity to BMLOV whereas others are resistant.

EXAMPLE 6

Effect of BMLOV on Normal B Cell Proliferation

Figure 3:
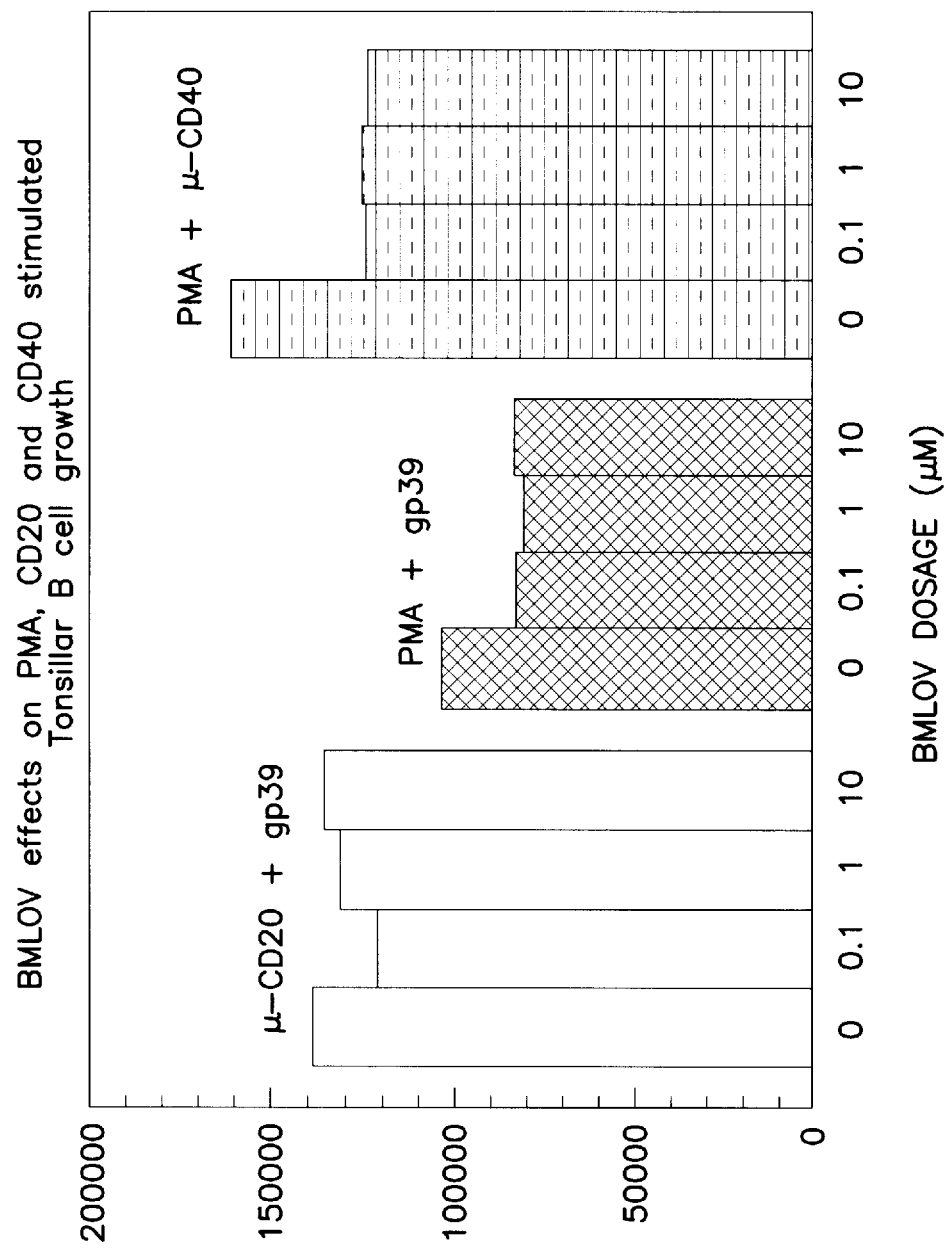
FIG. 3 is a graph showing the effects of varying doses of BMLOV on thymidine incorporation in normal tonsillar cells stimulated with varying combinations of ligands.
Figure 4:
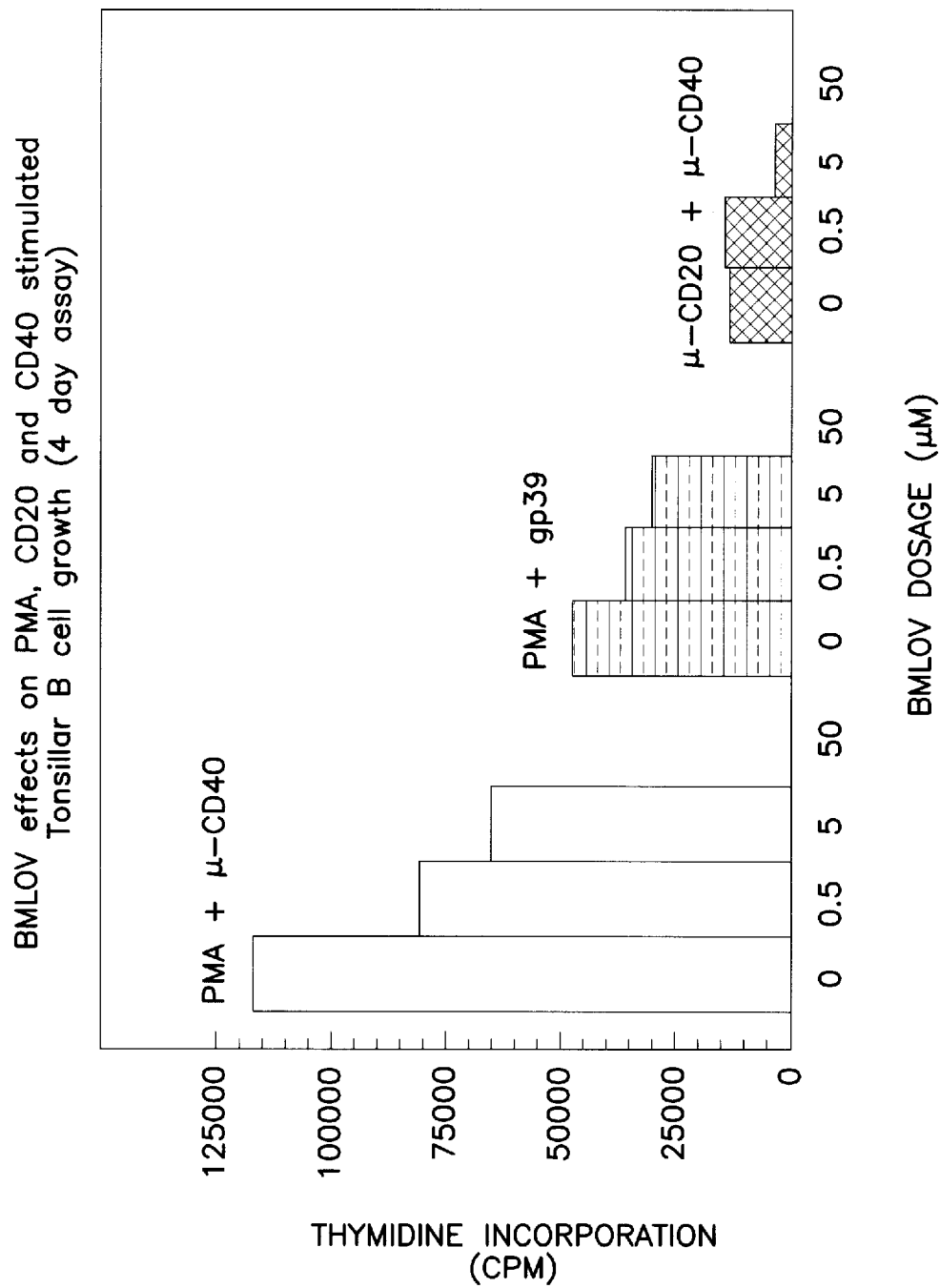
FIG. 4 is a similar graph showing the effects of varying doses of BMLOV on thymidine incorporation with tonsillar cells from a second donor.

BMLOV can inhibit normal tonsillar B cell proliferation driven by stimulation of CD40 via either anti-CD40 antibody or gp39 ligand plus either anti-CD20 antibody or phorbol 12-myristate 13-acetate (PMA). In one experiment, doses of 0.1 to 10 µM had little effect on proliferation (FIG. 3). In a second experiment, a dose of 5 µM gave substantial inhibition of proliferation and a dose of 50 µM completely blocked proliferation (FIG. 4). Variations between the individuals from which the tonsils were derived could account for the differences between these experiments.

Similarly, BMLOV can inhibit the proliferation of normal peripheral B cells. Normal B cell proliferation is mediated in part by the B cell surface molecule CD20, the B cell surface molecule CD40 in conjunction with its ligand gp39, and by the cytokine IL-4. The pharmacologic agent phorbol 12-myristate 13-acetate (PMA) can also be used in combination with these biological stimulation agents to further increase proliferation.

In the experiment reported in Table 4, monoclonal antibodies to CD20 and CD40 were used to stimulate proliferation. Peripheral B cells were isolated from two healthy human volunteers. The cells were stimulated as listed in Table 4 and the effects of various doses of BMLOV on proliferation, as measured by [$^3$H]-thymidine incorporation, were determined. BMLOV was able to inhibit proliferation induced by CD20, CD40, IL-4 and PMA in the various combinations tested. The cells from donor 2 were more sensitive, indicating some variation among individuals in their sensitivity to the drug.

It is important to note that the extent to which the proliferation of normal B cells was inhibited in this example (Table 4) was less than for the B cell leukemia and lymphoma cells examined in Examples 4 and 5. Phosphotyrosine phosphatase inhibitors such as BMLOV thus have the potential to act more selectively on malignant B cells than on normal B cells, offering an important advantage in the treatment of leukemia and lymphoma.

TABLE 4

INHIBITION OF NORMAL PERIPHERAL B CELL GROWTH BY BMLOV AS MEASURED IN [³H]-THYMIDINE INCORPORATION ASSAYS

| Dose, μm | [³H]cpm Incorporation For Stimuli: | | | |
|---|---|---|---|---|
| | PMA + CD40 | CD20 + CD40 | PMA + IL4 | CD40 + IL4 |
| Donor #1: | | | | |
| 0 | 65587 | 3574 | 61941 | 32499 |
| 1 | 62643 | 3619 | 61415 | 31966 |
| 5 | 58418 | 3644 | 48724 | 33845 |
| 10 | 45330 | 3422 | 45278 | 31637 |
| 25 | 25536 | 2432 | 14277 | 24933 |
| Donor #2: | | | | |
| 0 | 52672 | 5602 | 62228 | 19095 |
| 1 | 49102 | 4593 | 53642 | 16597 |
| 5 | 47624 | 5681 | 41892 | 18824 |
| 10 | 29024 | 5269 | 20313 | 12662 |
| 25 | 15671 | 856 | 2730 | 6013 |

Standard error did not exceed 8% for donor 1 and 15% for donor 2. Stimulation of CD20 was via monoclonal antibody 1F5 and stimulation of CD40 was via monoclonal antibody G28-5.

EXAMPLE 7

Sensitization of Ramos B Cells to Ionizing Radiation by BMLOV

Ionizing radiation in conjunction with bone marrow transplantation is a major therapy for leukemia. However, many leukemias are resistant to radiation, limiting the efficacy of this therapy.

It was previously demonstrated that ionizing radiation stimulates tyrosine kinases in human B lymphocyte precursors, triggering apoptosis and clonogenic cell death, an effect that was markedly enhanced by the phosphatase inhibitor orthovanadate.

Figure 5:
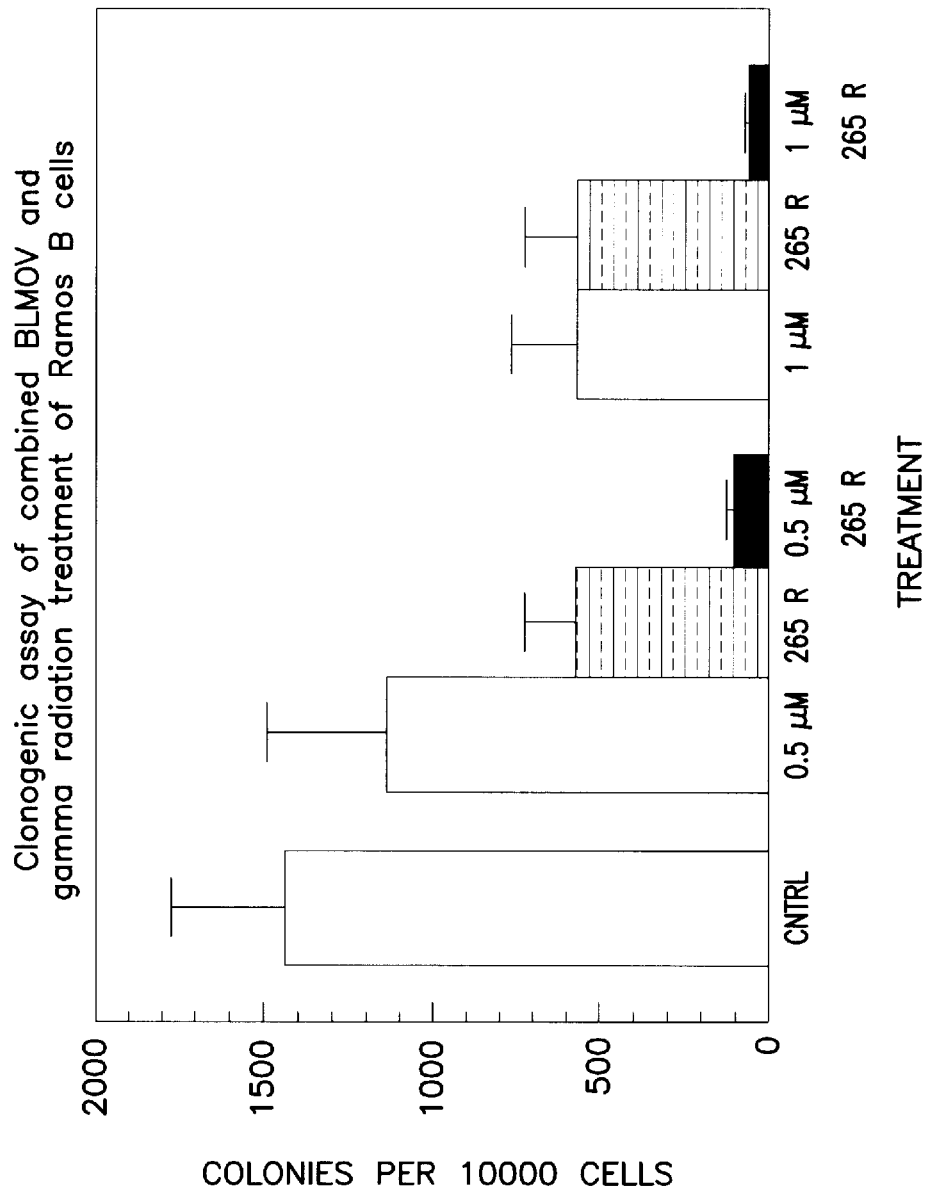
FIG. 5 is a graph showing the results of clonogenic assays after treatment of Ramos B cells with radiation alone, BMLOV alone, or radiation and BMLOV.

In clonogenic assays, as shown in FIG. 5, the combination of 1 μM BMLOV with 265 cGy radiation gave a 10-fold increase in cell death relative to radiation alone. The combination of 2 μM BMLOV with 265 cGy radiation gave a 50-fold increase in clonogenic cell death relative to radiation alone. These effects were synergistic rather than additive in that an approximately 5-fold enhancement in sensitization for the combination treatment was observed relative to expected additive effects based on the use of either treatment alone. These results suggest that phosphatase inhibitors such as BMLOV can be of value for use in combination with radiation therapy for the treatment of B cell malignancies.

EXAMPLE 8

Inhibition by BMLOV of CD28-Mediated $Ca^{2+}$ Signals and Cell Proliferation

BMLOV reproducibly caused marked inhibition of CD28 $Ca^{2+}$ signals in PHA T cell blasts. The inhibition was specific in that such inhibition was not observed for signals generated by CD3 alone or in combination with CD2 or CD4.

Figure 6:
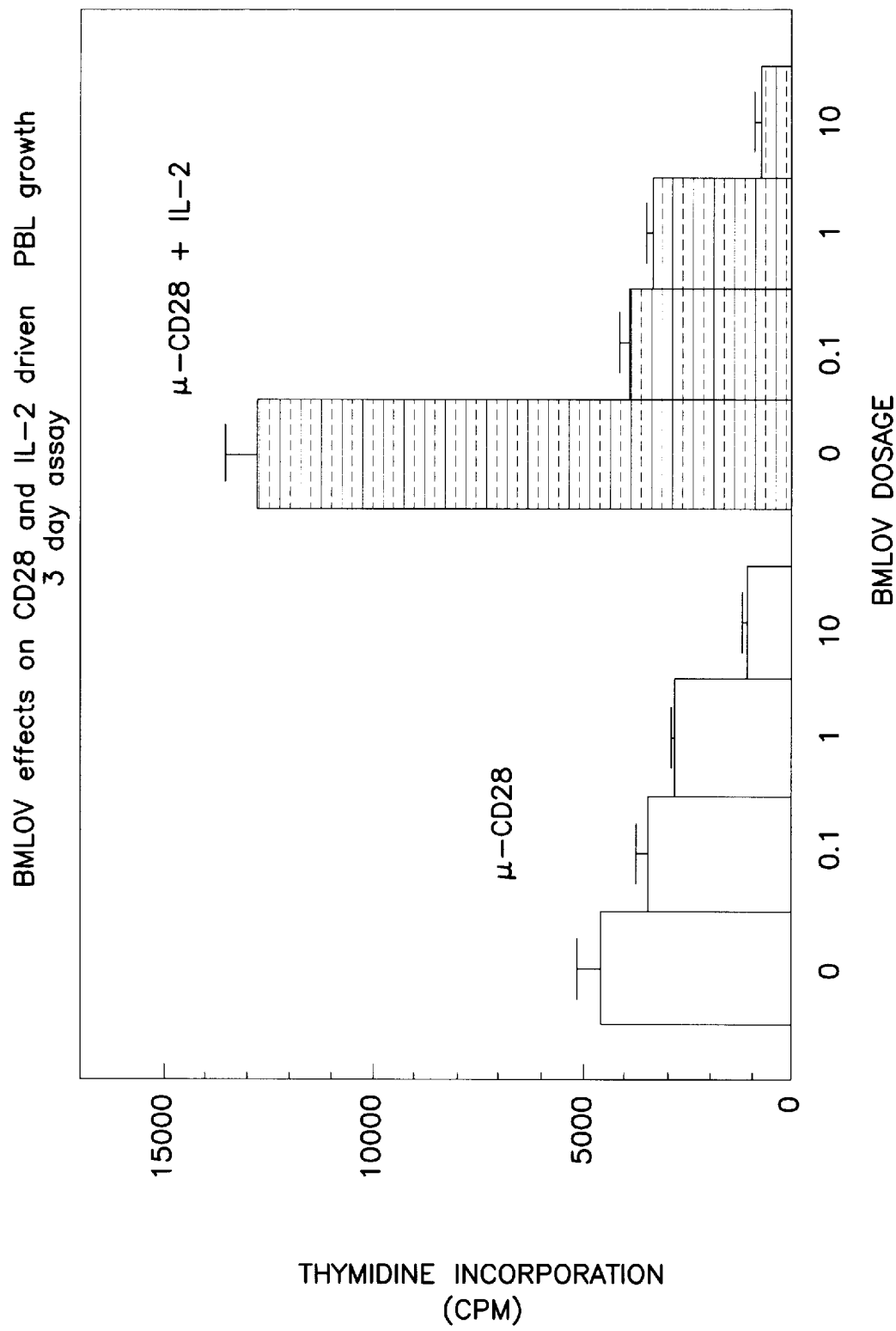
FIG. 6 is a graph showing the inhibition by BMLOV of growth of peripheral blood lymphocytes (PBL) driven by anti-CD28 antibody plus interleukin-2.
Figure 7:
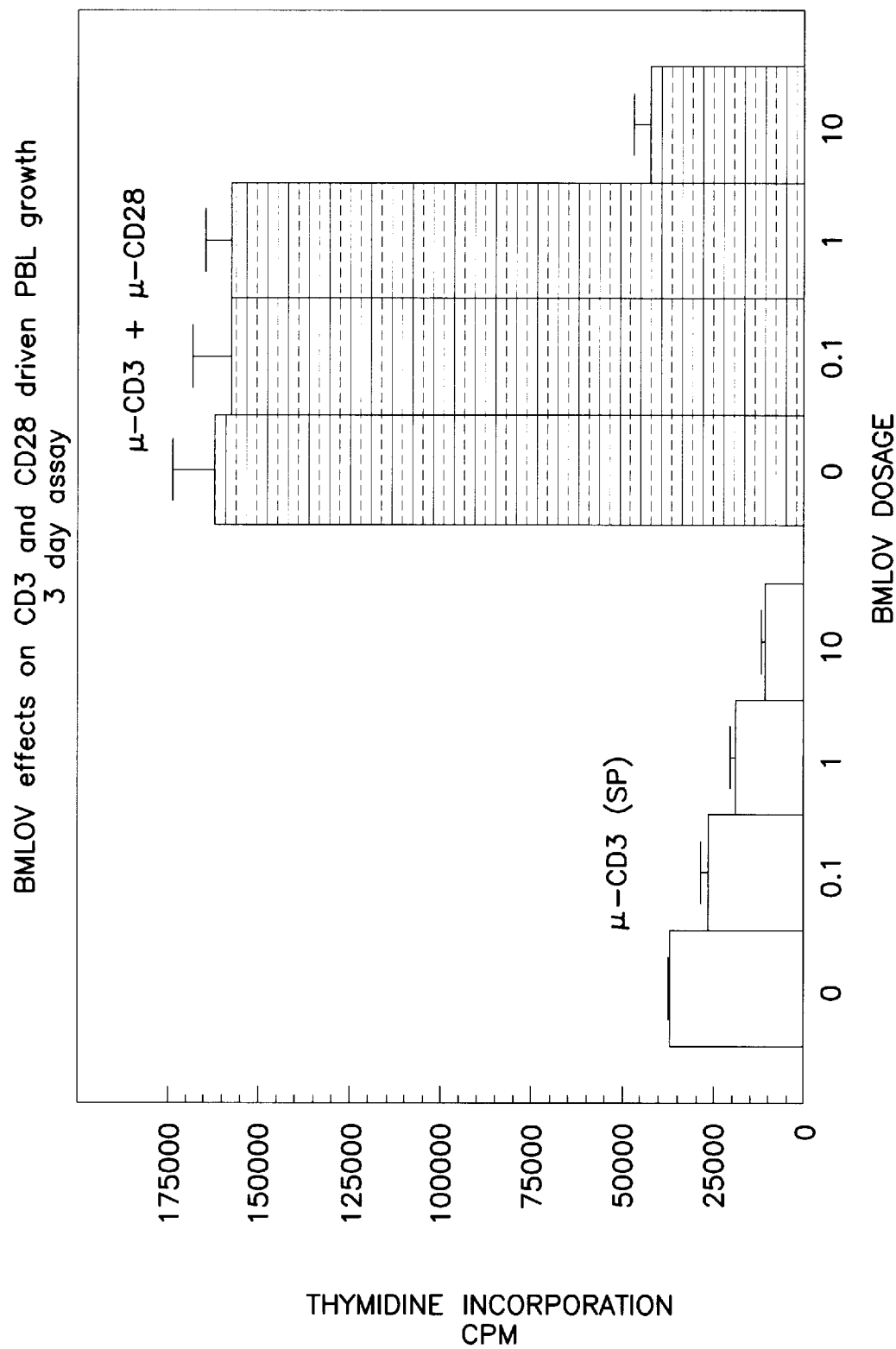
FIG. 7 is a graph showing the inhibition by BMLOV of growth of peripheral blood lymphocytes (PBL) driven by anti-CD28 antibody plus anti-CD3 antibody.

PBL growth driven by anti-CD28 antibody plus interleukin-2 (IL-2) was markedly inhibited by 1 μM BMLOV (FIG. 6) and growth driven by anti-CD3 antibody plus anti-CD28 antibody was strongly inhibited by 10 μM BMLOV (FIG. 7).

In contrast, substantially less inhibition was observed for IL-2 alone, PMA in combination with anti-CD28, or the factor-independent growth of the T cell line CEM, indicating the specificity of these effects.

Figure 8:
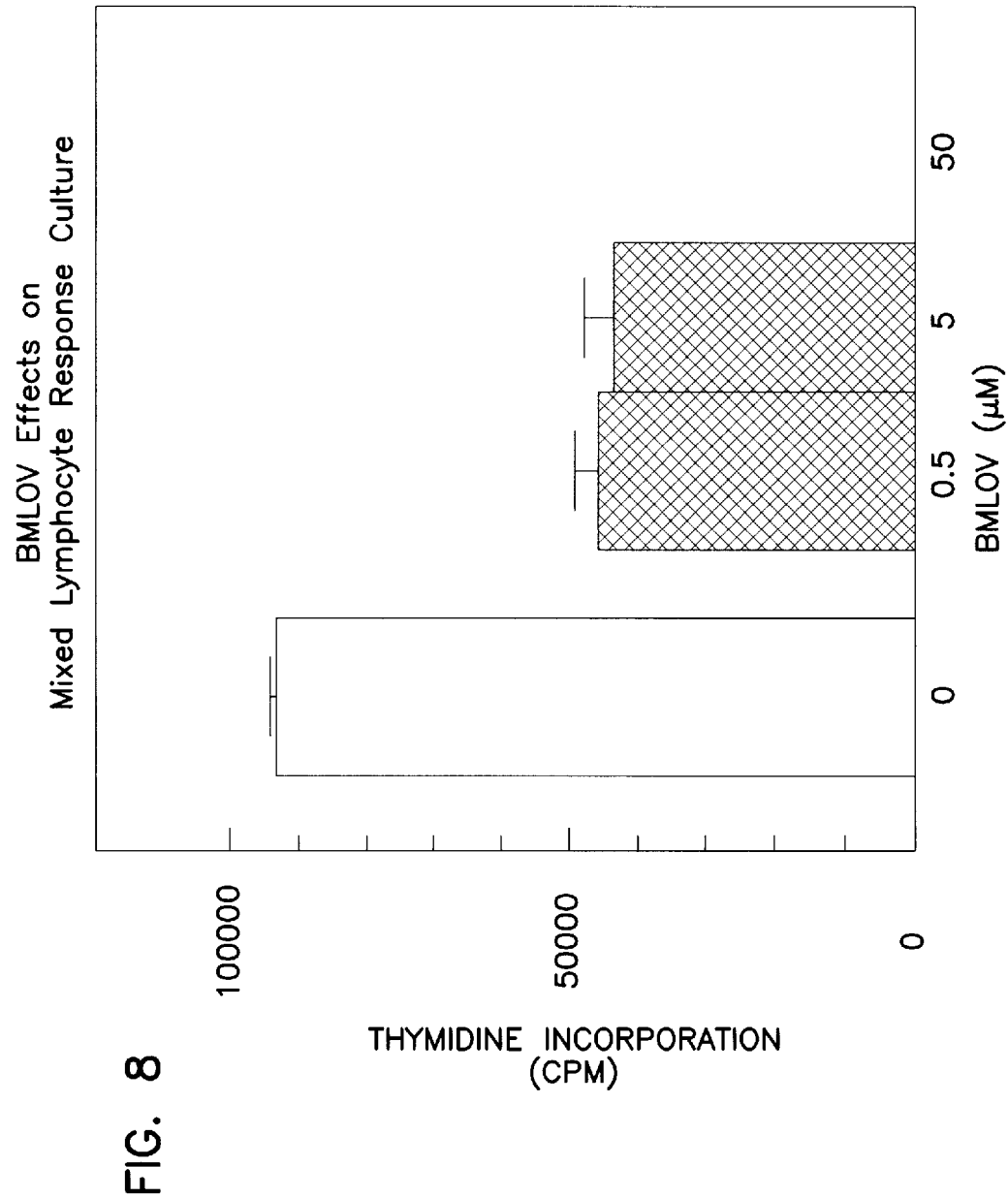
FIG. 8 is a graph showing the inhibition by BMLOV of growth in mixed lymphocyte response cultures dependent on CD28 costimulation.

Mixed lymphocyte response cultures that are dependent on CD28 costimulation were inhibited by over 50% by 0.5 to 5 μM BMLOV (FIG. 8). These results suggest the phosphatase inhibitor may selectively block CD28 effects and therefore can be used to block the generation of antibodies to antigens in animals.

An important question has been how does the costimulatory CD28 signal differ from the primary CD3 dependent signal in T cells, since both signals induce tyrosine phosphorylation and $Ca^{2+}$ flux. These results raise the possibility that the CD28 costimulatory or second signal requires a BMLOV-sensitive phosphatase activity that the primary signals do not.

EXAMPLE 9

Augmentation of Signals in T and B Cells by BMLOV

BMLOV was found to markedly enhance basal calcium levels in PHA blasts when the cells were treated with doses of 50 to 100 μM for fifteen hours. These results indicate that phosphatase activity is required to maintain normal calcium levels in the cell. Treatment of the cells with 25–50 μM BMLOV was found to prolong $Ca^{2+}$ signals generated by crosslinking CD3 alone or in combination with CD2 and CD4. BMLOV greatly increased and prolonged UV-induced $Ca^{2+}$ signals in Ramos B cells, indicating that phosphatase activity may limit UV-induced signals. BMLOV enhanced the tyrosine phosphorylation response of Ramos B cells to sIg crosslinking, particularly at early time points. These results suggest a potential for BMLOV to augment some cell responses.

EXAMPLE 10

BMLOV Inhibits Src-Family Kinase Activity in Lymphocytes and Colon Carcinoma Cells The Src-family kinases are known to require cellular phosphotyrosine phosphatase activity in order for them to respond in biologically stimulated cells. This is because Src-family kinases require a C-terminal tyrosine phosphorylation site to be dephosphorylated for activation to occur. Phosphotyrosine phosphatase inhibitors may therefore be expected to inhibit Src kinases indirectly by preventing their activation.

Treatment of Ramos cells with BMLOV for 15 hours inhibited the activity of the Src kinases Lyn and Fyn from the cells by approximately 50%.

Figure 9:
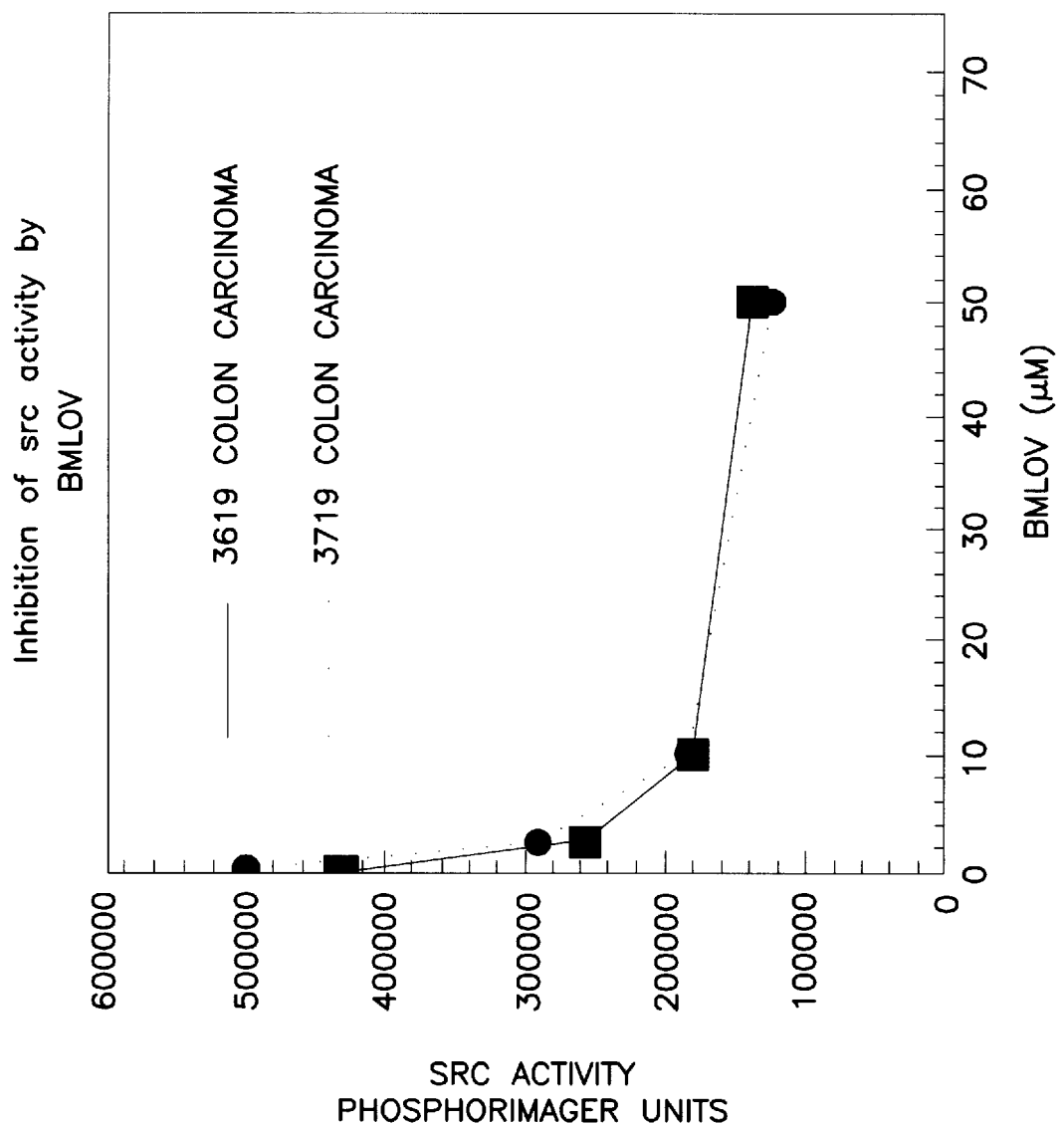
FIG. 9 is a graph showing the inhibition of $pp60^{c-Src}$ kinase activity in two colon carcinoma cell lines expressing Src by BMLOV.

Many colon carcinomas are known to express the Src oncogene product at high levels. In two colon carcinoma cell lines expressing Src, $pp60^{c-src}$ activity was strongly inhibited by BMLOV in a dose-dependent fashion (FIG. 9), while $pp60^{c-src}$ protein level remained constant. The treated cells showed morphological changes, including decreased adherence.

EXAMPLE 11

BMLOV Alters the Cell Cycle Progression of Treated Cells

A variety of anti-cancer therapies are known to alter the cell cycle progression of tumor cells. For example, both cisplatin and radiation therapy result in accumulation of cells in G2/M phase.

Ramos B cells treated with various concentrations of BMLOV for 16 hours were examined for their DNA content by propidium iodide staining followed by FACScan flow cytometric analysis using the SFIT program.

Figure 10:
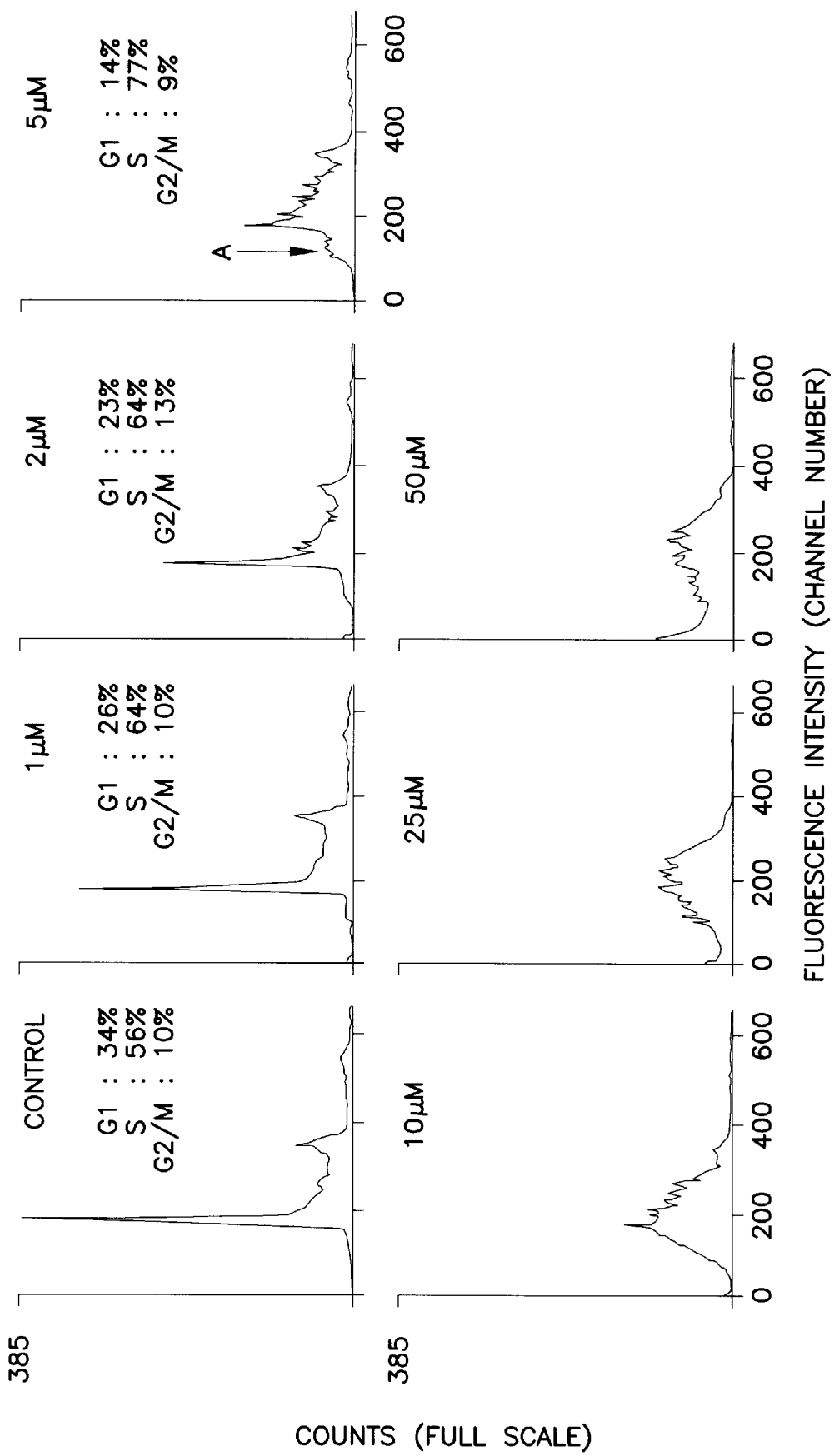
FIG. 10 is a graph showing the results of fluorescence-activated cell sorting (FACS) analysis of the cell cycle stage of Ramos B cells after treatment with BMLOV.

The results are shown in FIG. 10. The percentages of cells in G1, S, and G2/M are listed for doses of 0 to 5 μM of BMLOV. Percentages could not be calculated for higher doses due to the strong effects of the drug in causing apoptosis. Apoptotic cells lacking normal amounts of DNA are marked "A" in the 5 μM dose panel. BMLOV was found to preferentially deplete the proportion of cells in G1 while increasing the proportion in S phase. Loss of DNA due to apoptotic cell death was readily apparent in a dose of 5 μM and was greatly increased at high doses.

EXAMPLE 12

Effects of Analogs of BMLOV

Two analogs of BMLOV were prepared, vanadyl 1-benzoyl acetonate and vanadyl 2-acetyl 1-tetralonate.

The synthesis of vanadyl 2-acetyl 1-tetralonate was as follows. A quantity of 2-acetyl 1-tetralone (1.13 g; 0.006 moles) was dissolved in 74 ml of water with the pH adjusted to 13 with NaOH. A small amount of insoluble material was removed. Vanadyl sulfate (0.003 moles) was then added. The solution was then heated and allowed to reflux for 1 hour. The solution was then cooled on ice and 0.884 g product (a green solid) was collected and dried over $P_2O_5$. The yield was 33%. A similar procedure was used to synthesize vanadyl 1-benzoyl acetonate, starting with 1-benzoyl acetone. Vanadyl acetylacetonate, available commercially, was also studied.

Figure 11:
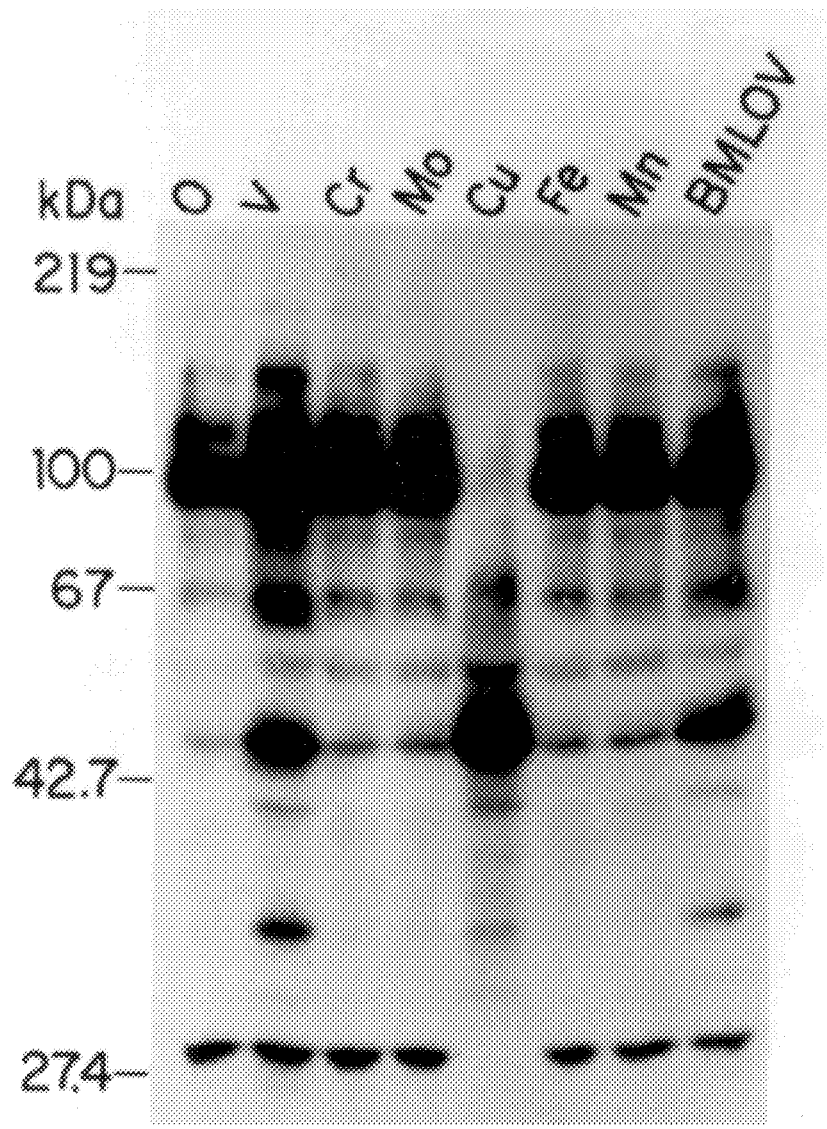
FIG. 11 is a photograph of an anti-phosphotyrosine western blot similar to those in FIGS. 1A–1C showing the effects of treating the cells with vanadyl acetylacetonate and analogs of vanadyl acetylacetonate in which the vanadium is replaced by molybdenum, chromium, iron, manganese, or copper, showing the induction of phosphorylation by vanadyl acetylacetonate in a pattern similar to that of BMLOV.

Of these analogs, only vanadyl acetylacetonate and vanadyl 1-benzoyl acetonate strongly induced cellular tyrosine phosphorylation. As shown in FIG. 11, anti-phosphotyrosine western blot analysis of whole cell lysates following SDS-PAGE revealed that vanadyl acetylacetonate strongly induced tyrosine phosphorylation in a pattern very similar to that of BMLOV.

Analogs of vanadyl acetylacetonate were prepared in which the vanadium was replaced with other metals, namely molybdenum, chromium, iron, manganese, or copper. Of these analogs with differing metal ions, only cupric acetylacetonate induced tyrosine phosphorylation, but in a different pattern than for the vanadyl compounds (FIG. 11). Thus, only certain metals are active in this type of compound.

Clonogenic assays of Ramos Burkitt lymphoma cells treated with cupric acetylacetonate showed that the cells were sensitive to the compound at doses of 10 and 25 μM (Table 5).

TABLE 5

Effect of Cupric Acetylacetonate on Ramos B Cells as Measured in Clonogenic Assays

| Dose, μM | Colonies | SE |
|---|---|---|
| 0 | 9126 | 1944 |
| 1 | 5749 | 1070 |
| 5 | 226 | 26 |

TABLE 5-continued

Effect of Cupric Acetylacetonate on Ramos B Cells as Measured in Clonogenic Assays

| Dose, μM | Colonies | SE |
|---|---|---|
| 10 | 127 | 35 |
| 25 | 31 | 8 |

EXAMPLE 13

BMLOV Was Tolerated by Animals

BMLOV is tolerated by animals when it was administered by oral or intraperitoneal routes. Mice were treated with 1.6 mM of BMLOV in their drinking water continuously for 10 days, and the level of the drug in their blood serum was determined by atomic absorption spectroscopy after 1 and 10 days of treatment, as shown in Table 6. The mice displayed no overt ill effects from the drug treatment. Subsequently, mice have received intraperitoneal doses of BMLOV of up to 1 mg and oral doses of up to 1.6 mg without ill effects except for some temporary lethargy.

TABLE 6

BMLOV Levels in Mouse Sera

| Mouse | Day | BMLOV in Serum, μM |
|---|---|---|
| 647 | 1 | 9.5 |
| 648 | 1 | 5.3 |
| 649 | 1 | 7.5 |
| 650 | 1 | 8.7 |
| 647 | 10 | 11.4 |
| 648 | 10 | 11.0 |
| 649 | 10 | 7.5 |
| 650 | 10 | 7.7 |

EXAMPLE 14

Prevention of Class-Switching in Antibody-Producing B Cells by BMLOV

The effects of BMLOV were assayed on class-switching in antibody-producing B cells. Human B cells producing antibody were treated with anti-CD40 antibody plus IL-4, which increased production of IgE over 10-fold (Table 7). However, in the presence of 5.6 or 17 μM BMLOV, the increased production of IgE was markedly inhibited. In contrast, the production of IgG1 and IgG4 was much less affected, particularly at a dose of 5.6 μM BMLOV. This selective effect is important because the IgG antibody production is an important response to infectious disease. It would be of value to suppress IgE production for the treatment of allergies while maintaining IgG production, particularly in conditions in which an allergy coexists with an infectious disease. A common example is the exacerbation of allergic rhinitis (hay fever) as the result of a respiratory infection.

TABLE 7

EFFECT OF BMLOV ON CLASS-SWITCHING IN ANTIBODY-PRODUCING B CELLS

| Treatment of Cells | [Ig], ng/ml: | | | |
|---|---|---|---|---|
| | IgG1 | IgG4 | IgM | IgE |
| Untreated | 225 | 0.7 | 6.6 | 0.5 |
| Anti-CD40 + IL-4 | 510 | 1.7 | 16.8 | 5.7 |
| Anti-CD40 + IL-4 + 0.002 μM BMLOV | 450 | 1.7 | 20.4 | 3.9 |
| Anti-CD40 + IL-4 + 0.008 μM BMLOV | 450 | 1.1 | 20.4 | 2.6 |
| Anti-CD40 + IL-4 + 0.02 μM BMLOV | 390 | 1.3 | 19.2 | 4.5 |
| Anti-CD40 + IL-4 + 0.07 μM BMLOV | 450 | 2.7 | 12.0 | 5.1 |
| Anti-CD40 + IL-4 + 0.2 μM BMLOV | 495 | 1.2 | 13.8 | 7.5 |
| Anti-CD40 + IL-4 + 0.6 μM BMLOV | 480 | 1.3 | 17.4 | 5.7 |
| Anti-CD40 + IL-4 + 1.9 μM BMLOV | 450 | 2.7 | 15.6 | 3.0 |
| Anti-CD40 + IL-4 + 5.6 μM BMLOV | 480 | 1.8 | 18.6 | 1.2 |
| Anti-CD40 + IL-4 + 17 μM BMLOV | 450 | 0.8 | 18.0 | 0.8 |
| Anti-CD40 + IL-4 + 50 μM BMLOV | 60 | 0.5 | 5.1 | 0.2 |

EXAMPLE 15

Growth Inhibition and Selective Induction of Apoptosis in B Cell and Myeloid Leukemia Cells by Phosphotyrosine Phosphatase Inhibition This example synthesizes and correlates the results previously shown in Example 2, Example 3, Example 4, and Example 6, as well as other examples, using flow cytometry for cell cycle analysis.

Materials and Methods

Cells and reagents.

The human Burkitt's lymphoma lines Ramos and Raji, the human T cell leukemia lines CEM and Jurkat, the human acute promyelocytic leukemia line HL-60 and the human acute monocytic leukemia line THP-1 were obtained from the American Type Culture Collection and were grown in RPMI 1640 medium (GIBCO, Gaithersburg, Md.) with 10% fetal calf serum. The murine B cell lymphoma line A20 and the murine B cell leukemia line BCL1 were obtained from the American Type Culture Collection and were grown in RPMI 1640 media, 10% fetal bovine serum plus 50 μM β-mercaptoethanol. The human colon carcinoma cell line H3347 (J. S. Marken et al., "Cloning and Expression of the Tumor-Associated Antigen L6," *Proc. Natl. Acad. Sci. USA* 89:3503–3507 (1992)) was grown in IMDM medium (GIBCO) with 10% fetal bovine serum. Anti-human CD3 ε chain monoclonal antibody G19-4, anti-human CD45 monoclonal antibody 9.4, and anti-human CD40 monoclonal antibody G28-5 have been previously described (J. A. Hansen et al., "Human T Lymphocyte Cell Surface Molecules Defined by the Workshop Monoclonal Antibodies," in *Leukocyte Typing I* (A. Bernard et al., eds., Springer-Verlag, N.Y. 1984), pp. 195–212; B. F. Haynes, "Summary of T Cell Studies Performed During the Second International Workshop and Conference on Human Leukocyte Differentiation Antigens," in *Leukocyte Typing II* (E. L. Reinherz, ed., Springer-Verlag, N.Y., 1986), pp. 3–30; E. A. Clark & J. A. Ledbetter, "Activation of Human B Cells Mediated Through Two Distinct Cell Surface Antigens, Bp35 and Bp50," *Proc. Natl. Acad. Sci. USA* 83:4494–4498 (1986); J. A. Ledbetter et al., "CD45 Regulates Signal Transduction and Lymphocyte Activation by Specific Association with Receptor Molecules on T or B Cells," *Proc. Natl. Acad. Sci. USA* 85:8628–8632 (1988)). Rabbit anti-human IgM (Fab')$_2$ was from Jackson Immunoresearch Labs (West Grove, Pa.). Protein tyrosine phosphatase PTP1B and serine phosphatases PP1 and PP2A were from Upstate Biotechnology (Lake Placid, N.Y.). Calf intestinal alkaline phosphatase was from Sigma (St. Louis, Mo.). Bis(maltolato) oxovanadium (IV) was synthesized as previously described (J. H. McNeill et al., (1992), supra; C. P. Stewart & A. L. Porte, "Electron Paramagnetic Resonance Spectra of Some Oxovanadium (IV) Chelates," *J. Chem. Soc. Dalton Trans.* 1661–1666 (1972)). The product was characterized by infrared and mass spectroscopy.

Analysis of Tyrosine Phosphorylation and Phosphatase Activity

Anti-phosphotyrosine immunoblotting was performed as previously described (D. Dailey et al., "Novel Yeast Protein Kinase (YPK1 Gene Product) is a 40-Kilodalton Phosphotyrosyl Protein Associated with Protein Tyrosine Kinase Activity," *Mol. Cell Biol.* 10:6244–6256 (1990)). Antibody binding was detected using [$^{125}$I] protein A followed by autoradiography. CD45 and PTP1B were assayed using the substrate phosphorylated myelin basic protein as described (K. Guan et al., "A Tyr/Ser Protein Phosphatase Encoded by Vaccinia Virus," *Nature* 350:359–362 (1991)), except that two-minute assays were performed. The bovine brain myelin basic protein was [$^{32}$P] labeled on tyrosine by phosphorylation with recombinant Lck tyrosine kinase expressed in a baculovirus-Sf9 insect cell system. Lck specifically phosphorylates bovine myelin basic protein on the tyrosine 67 residue (Q. Wang et al., "Identification of Tyrosine 67 in Bovine Brain Myelin Basic Protein as a Specific Phosphorylation Site for Thymus p56$^{lck}$," *Biochem. Biophys. Res. Comm.* 178:1393–1399 (1991)). Baculovirus encoding the lck gene were provided by Dr. Joseph Bolen (Bristol-Myers Squibb Pharmaceutical Research Institute, Princeton, N.J.). CD45 was immunoprecipitated from Jurkat T cells with mAb 9.4 and assayed as the immune complex. PP1, PP2A, and calf intestinal alkaline phosphatase were assayed with p-nitrophenyl phosphate as a substrate.

Cellular Proliferation and Clonogenic Assays.

For assays of cellular proliferation, cells were grown five days in the presence of the indicated concentrations of BMLOV, pulsed 6 hr with [$^3$H]-thymidine (New England Nuclear, Boston, Mass.), and counted in a liquid scintillation counter. Human peripheral blood lymphocytes (PBL) from normal volunteers were isolated from lymphocyte separation medium (Litton Bionetics, Kensington, Md.) by density gradient centrifugation. Monocytes were depleted from PBL by two rounds of plastic absorption for 30 minutes at 37° C. B cells were enriched for by negative selection using complement plus monoclonal antibodies to CD2, CD3, CD4, and CD8 for complement depletion. Clonogenic assays of colony formation in methylcellulose medium were performed as previously described (F. M. Uckun et al. (1992), supra).

DNA Fragmentation and Cell Death.

Cellular DNA was extracted and then the state of DNA fragmentation was analyzed by agarose gel electrophoresis as previously described (K. L. Donaldson et al., "Cytotoxicity of the Anti-Cancer Agents Cisplatin and Taxol During Cell Proliferation and the Cell Cycle," *Int. J. Cancer*

57:847–855 (1994)). Cell death was measured by staining cells with propidium iodine followed by flow cytometry (EPICS C, Coulter) as previously described (N. K. Damle et al. (1993), supra; Y. Liu & C. A. J. Janeway, "Interferon Gamma Plays a Critical Role in Induced Cell Death of Effector T Cells: A Possible Third Mechanism of Self-Tolerance," *J. Exp. Med.* 172:1735–1739 (1990)). Flow cytometric data on forward scatter and red fluorescence arising from propidium iodine binding to cellular DNA was collected for 5,000 cells and analyzed by the Quadstat Program (N. K. Damle, (1993), supra). The membranes of dead cells are permeable to propidium iodine (Y. Liu & C. A. Janeway, (1990), supra), but cells undergoing the process of apoptosis can shrink in size while temporarily maintaining plasma membrane integrity (J. J. Cohen et al., "Apoptosis and Programmed Cell Death and Immunity," *Annu. Rev. Immunol.* 10:267–293 (1992)). Dead cells exhibiting both reduced size (lower forward scatter) and staining by propidium iodide (elevated red fluorescence) are found in the upper left quadrant, cells with damaged membranes but of normal size are found in the upper right quadrant and compromised cells of reduced size but which are impermeable to propidium iodide are found in the lower left quadrant. Only cells displaying normal size and resistance to staining by propidium iodide are considered viable cells and are found in the lower left quadrant (M. K. Damle et al. (1993), supra). The percentage of cells in each quadrant was calculated by the Quadstat program.

Cell Cycle Analysis.

Cells were fixed, permeabilized and stained for their DNA content with propidium iodide as previously described (D. H. Pluznik et al., "Colony Stimulating Factor (CSF) Controls Proliferation of CSF-Dependent Cells by Acting During the G1 Phase of the Cell Cycle," *Proc. Natl. Acad. Sci. USA* 81:7451–7455 (1984)). The stained cells were analyzed by flow cytometry on a FACScan (Becton-Dickinson) instrument. The percentage of cells in various stages of the cell cycle was calculated using the CellFIT program.

Results of experiments in which the ability of BMLOV to inhibit various types of phosphatases was studied are shown in Table 8. BMLOV was a highly potent and selective inhibitor of phosphotyrosine phosphatases such as CD45 and PTP1B, displaying IC50 values of approximately 25 nM for these phosphotyrosine phosphatases while requiring over 100-fold greater concentration to give similar inhibition of the serine/threonine phosphatases PP1 and PP2A. The selective inhibition of phosphotyrosine phosphatases relative to serine/threonine phosphatases by BMLOV is similar to results in previous studies on sodium orthovanadate (J. A. Gordon, "Use of Vanadate as a Protein-Phosphotyrosine Phosphatase Inhibitor," *Meth. Enzymol.* 201B:477–482 (1991)). Calf intestinal alkaline phosphatase was inhibited less than 10% by 500 $\mu$M BMLOV, whereas sodium orthovanadate has been reported to strongly inhibit calf intestinal alkaline phosphatase at concentrations of less than 20 $\mu$M (A. M. Cortizo et al., "Vanadium Compounds: Their Action on Alkaline Phosphatase Activity," *Biol. Trace Elem. Res.* 41:331–339 (1994)), indicating a greater degree of selectivity by BMLOV relative to orthovanadate.

TABLE 8

SELECTIVE INHIBITION OF PHOSPHOTYROSINE PHOSPHATASES BY BMLOV

| Phosphatase | IC50($\mu$m) | SEM | n |
|---|---|---|---|
| PTP1B | 26 | 7 | 5 |
| CD45 | 25 | 1 | 3 |
| PP1 | 6156 | 360 | 2 |
| PP2A | 3337 | 208 | 2 |
| Alkaline Phosphatase | >5 × 10$^5$ | — | 2 |

SEM = standard error of the mean
n = number of experiments

The potent PTP inhibitor phenylarsine oxide has been reported to strongly induce tyrosine phosphorylation in T cells, but the high reactivity of this compound with protein sulfhydryl groups limits its utility for biological studies and for in vivo use (P. G. Garcia-Morales et al., "Tyrosine Phosphorylation in T Cells Is Regulated by Phosphatase Activity: Studies with Phenylarsine Oxide," *Proc. Natl. Acad. Sci. USA* 87:9255–9259 (1990); M. C. Fletcher et al., "Complex Effects of Phenylarsine Oxide in T Cells," *J. Biol. Chem.* 268:23697–23703 (1993)). Accordingly, the effect of BMLOV on the induction of cellular tyrosine phosphorylation was examined. BMLOV displayed a dose-dependent induction of tyrosine phosphorylation in Ramos B cells (FIG. 12A).

Figure 12A:
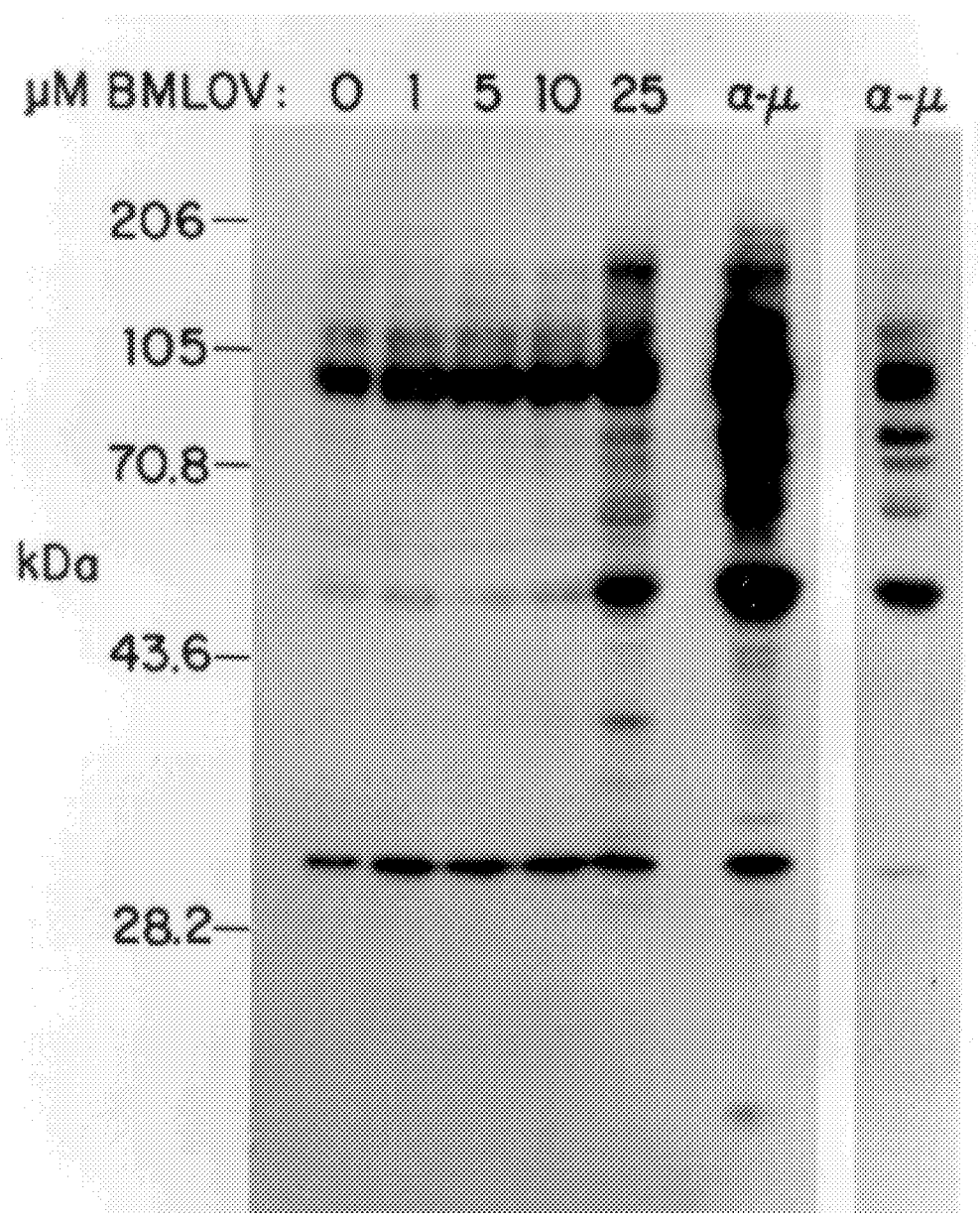
FIG. 12A is a photograph of anti-phosphotyrosine immunoblots showing the induction of cellular tyrosine phosphorylation in Ramos B cells by BMLOV.
Figure 12B:
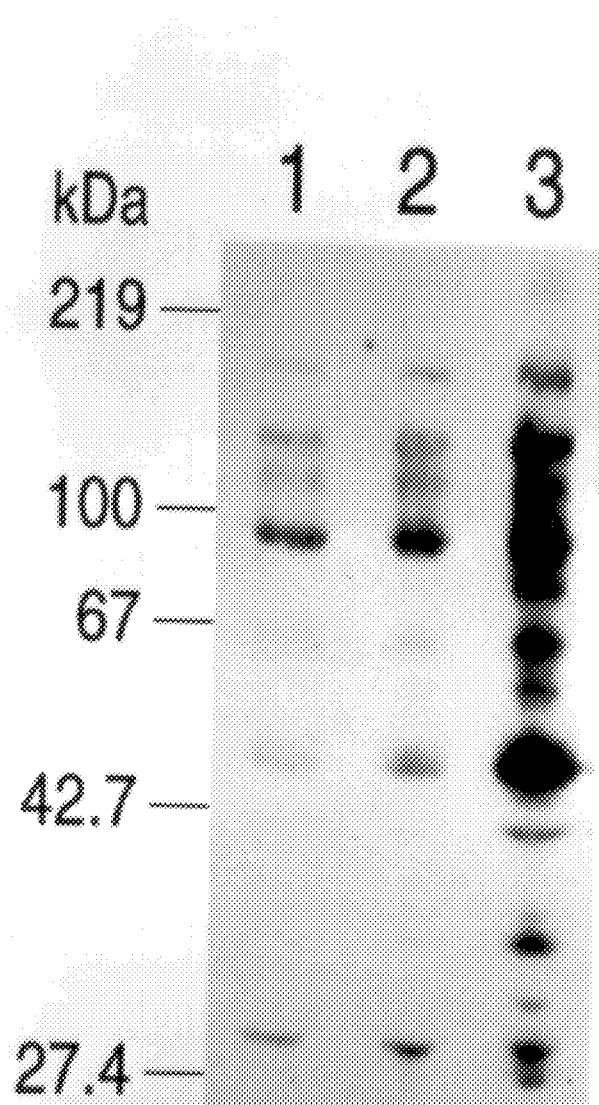
FIG. 12B is a similar photograph of anti-phosphotyrosine immunoblots comparing the induction of cellular tyrosine phosphorylation in Ramos B cells by BMLOV and orthovanadate.
Figure 12C:
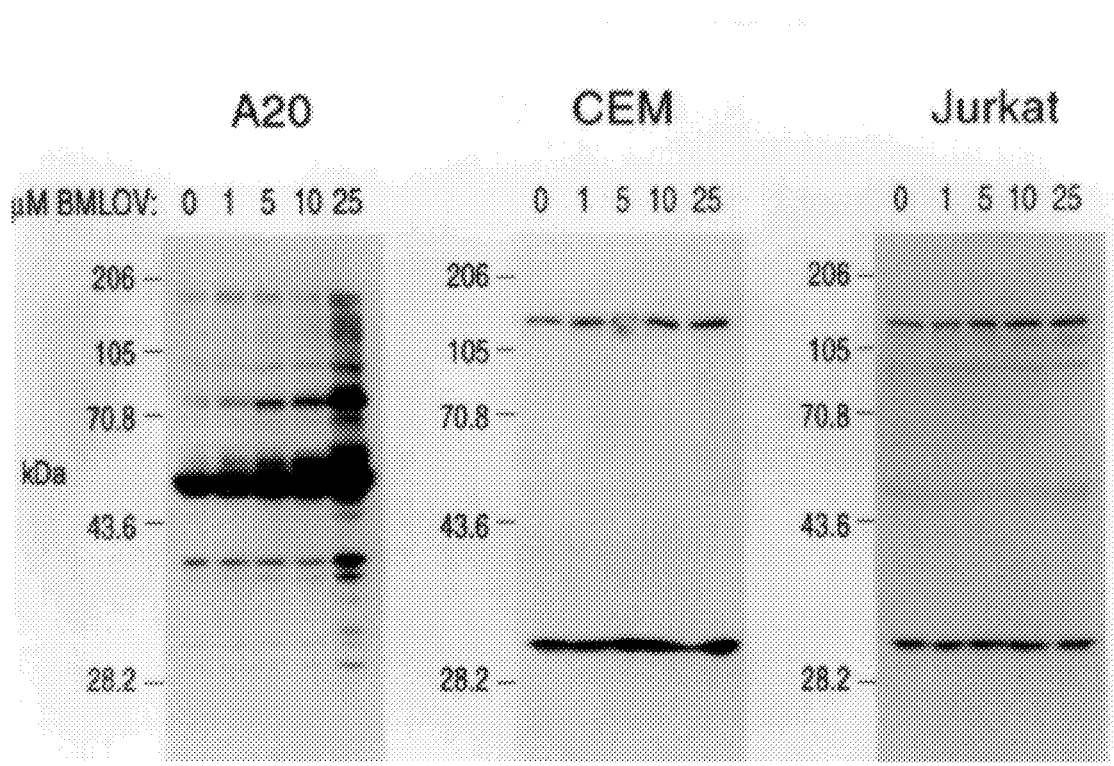
FIG. 12C is a similar photograph of anti-phosphotyrosine immunoblots comparing the induction of cellular tyrosine phosphorylation in murine B cell lymphoma A20 cells and the human T cell leukemia lines CEM and Jurkat after 16-hr treatments with the indicated concentrations of BMLOV.

In the experiments shown in FIGS. 12A–12C, anti-phosphotyrosine immunoblotting of cellular proteins was performed using [$^{125}$I]-protein A followed by autoradiography to detect antibody binding. In FIG. 12A, Ramos B cells were treated with the indicated concentrations of BMLOV for 16 h, or were stimulated with goat anti-human IgM F(ab')$_2$ ($\alpha$-$\mu$) for 1 min. The $\alpha$-$\mu$ lane at right is a 6-fold shorter autoradiographic exposure than the left $\alpha$-$\mu$ lane to show greater detail.

In FIG. 12B, Ramos B cells were untreated (lane 1) or treated 30 min with either 100 $\mu$M sodium orthovanadate (lane 2) or 100 $\mu$M BMLOV (lane 3).

In FIG. 12C, murine B cell lymphoma A20 cells and the human T cell leukemia CEM and Jurkat were treated 16 hr with the indicated concentrations of BMLOV.

At a dose of 25 $\mu$M, the pattern of tyrosine phosphorylation was very similar to that induced by crosslinking surface IgM, but the level of phosphorylation was substantially less than that obtained following a maximal stimulation of the antigen receptor (anti-$\mu$). The phosphorylation was prolonged, however, as evidenced by the results of continuous exposure to the drug shown in FIG. 12A. These results indicate that BMLOV is active in cells, in addition to its activity against PTPs in direct enzyme assays.

The induction of cellular tyrosine phosphorylation by BMLOV was compared to that induced by the widely used PTP inhibitor sodium orthovanadate. As shown in FIG. 12B, BMLOV was more potent than orthovanadate in the induction of tyrosine phosphorylation in Ramos B cells. The strong induction of cellular tyrosine phosphorylation at 30 min (FIG. 12B) indicates that BMLOV acts rapidly to induce cellular tyrosine phosphorylation. However, the ability of BMLOV to induce tyrosine phosphorylation was cell type specific. BMLOV induced only low levels of tyrosine phosphorylation in the human T cell leukemia lines CEM and Jurkat, whereas the murine B cell lymphoma line A20 was highly responsive (FIG. 12C). These results indicate that BMLOV shows selectivity for B cells relative to T cells in the induction of tyrosine phosphorylation.

Figure 13:
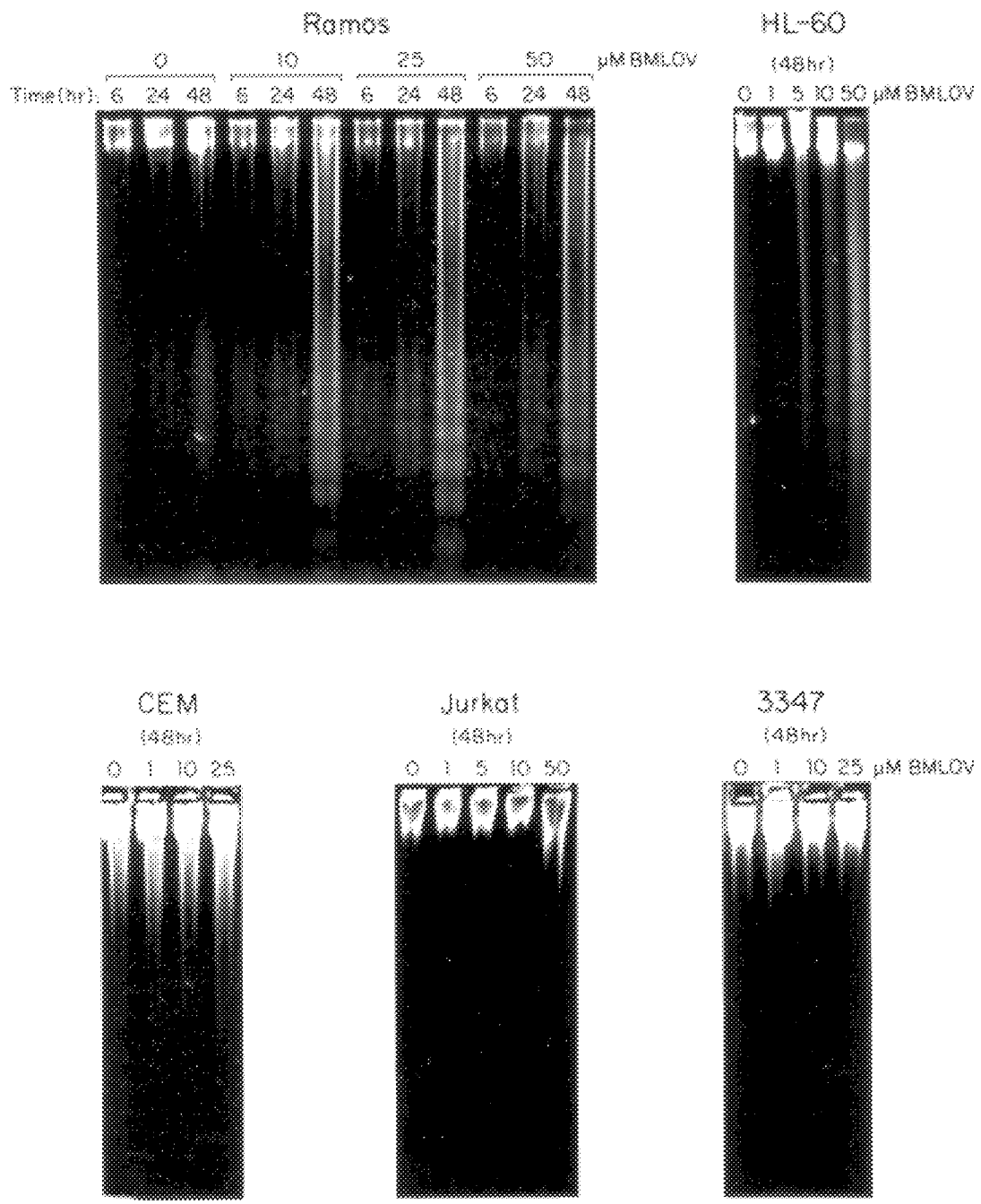
FIG. 13 is a photograph of a stained electropherogram on an agarose gel of DNA from Ramos, HL-60, CEM, Jurkat, and 3347 cells treated with the indicated concentrations of BMLOV for the indicated times, showing the apoptosis induced.

In addition, the induction of apoptosis and altered cell progression by BMLOV was examined. BMLOV induced apoptosis in Ramos B cell lymphoma lines within 48 hours at a dose of 10 $\mu$M, as demonstrated by the induction of extensive DNA fragmentation (FIG. 13). In FIG. 13, cells were treated with BMLOV for the times and at the concentrations indicated. DNA was extracted and the state of DNA fragmentation was examined by agarose gel electrophoresis. This pattern of DNA fragmentation is a hallmark of apoptosis in many cell types, including lymphocytes, as a result of cleavage of DNA between nucleosomes (J. J. Cohen (1992), supra). Higher doses induced DNA fragmentation within 24 hours of treatment. DNA fragmentation was also induced in the human acute promyelocytic leukemia cell line HL60 in a dose dependent manner (FIG. 13). Induction of apoptosis was specific for myeloid and B cell lineages in that DNA fragmentation was not observed in the human T cell leukemia cell lines CEM or Jurkat, nor was it observed in the human colon carcinoma cell line 3347 (FIG. 13).

Since crosslinking sIg can induce growth arrest at the G1 stage of the cell cycle in B-lineage lymphoma cells in a process requiring the Lyn tyrosine kinase (R. H. Scheuermann et al. (1994), supra), the effect of PTP inhibition on cell cycle progression was investigated. The DNA content of Ramos B cells was examined by staining with propidium iodide followed by flow cytometry (FIG. 14).

Figure 14:
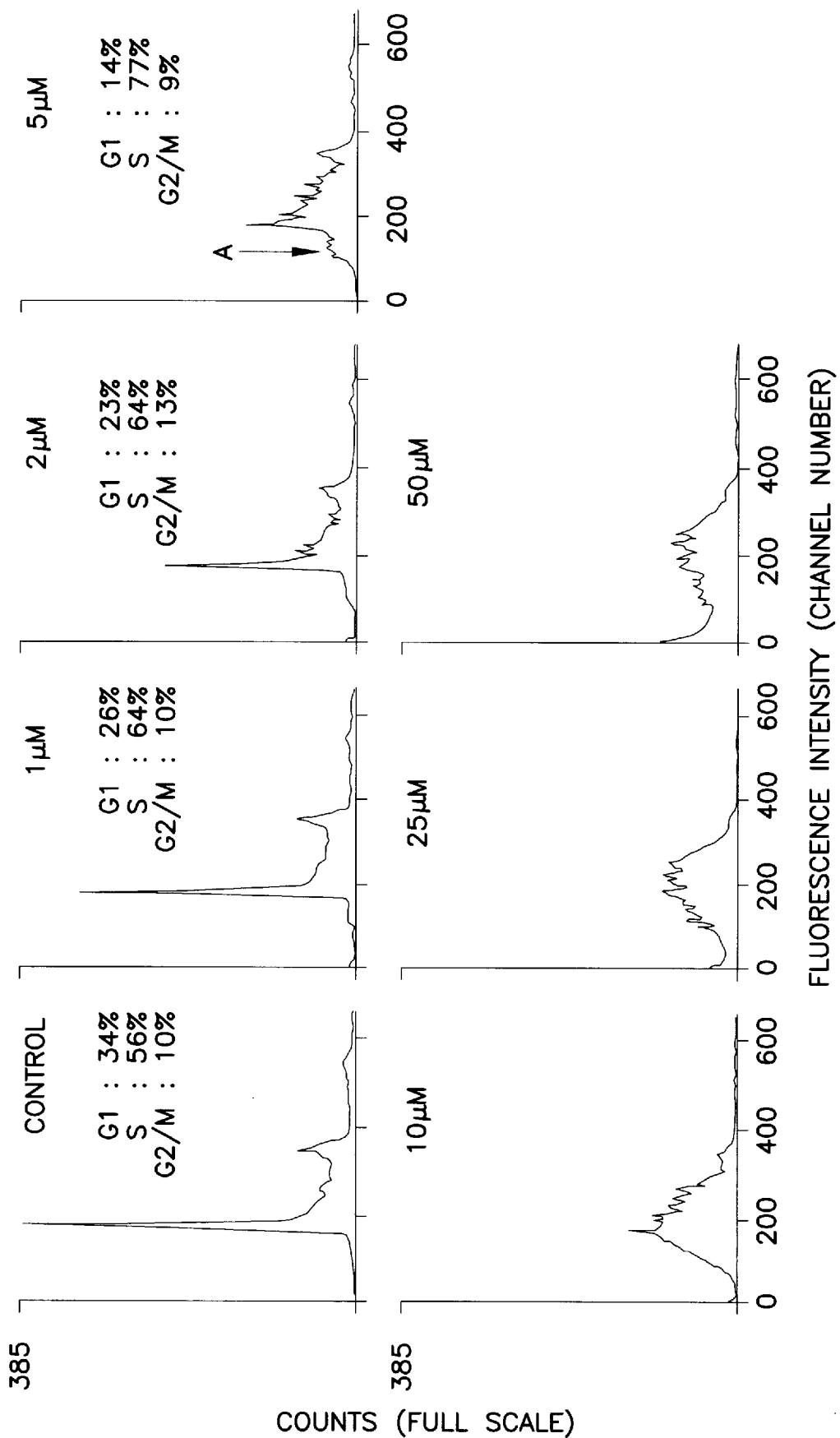
FIG. 14 is a series of graphs showing the effect of BMLOV on cell cycle progression for Ramos cells growing in log phase for various concentrations of BMLOV; DNA in the cells was stained with propidium iodine and quantitated by flow cytometry; the calculated percentage of cells at the stages of the cell cycle is shown ("A" marks apoptotic cells lacking normal amounts of DNA in the 5 μM dose panel)

In FIG. 14, Ramos cells growing in log phase were treated with BMLOV for 48 hr at the indicated concentrations. DNA in the cells was stained with propidium iodide and quantitated by flow cytometry as described previously. The calculated percentage of cells at the stages of the cell cycle is shown. "A" marks apoptotic cells lacking normal amounts of DNA in the 5 $\mu$M dose panel.

BMLOV preferentially depleted the proportion of cells in G1 in a dose dependent manner. The proportion of cells dropped from 34% of the control cells to only 14% in cells treated with 5 $\mu$M of the inhibitor. Simultaneously, the proportion of cells in S phase increased from 56% for control cells to 77% for cells treated with 5 $\mu$M BMLOV. The proportion of cells in G2/M did not change substantially. At a dose of 5 $\mu$M, apoptotic cells lacking normal amounts of DNA were readily apparent, and the proportion of cells undergoing apoptosis showed a clear increase with increasing doses of the inhibitor (FIG. 14). At higher doses the percentages of cells at various stages of the cell cycle could not be calculated due to the strong induction of apoptosis. These findings confirm that BMLOV induces apoptosis in a dose dependent manner and indicate that the inhibitor also perturbs normal cell cycle progression in the cells, resulting in a decrease in the fraction in cells in G1 phase and an increase in the fraction of cells in S phase.

Therefore, the ability of the inhibitor to induce apoptosis and alter cell cycle progression sufficiently to block clonogenic cell growth was also examined. In vitro methylcellulose colony assays of clonogenic cell growth revealed that the B cell Burkitt lymphoma lines Ramos and Raji were both highly sensitive to BMLOV treatment, displaying greater than 99.9% inhibition when treated with 10 $\mu$M of the inhibitor (Table 9). These results are consistent with the induction of apoptosis previously observed for the Ramos cells (Example 11). These results for BMLOV contrast strongly with previous studies of vanadate, which only gave slight effects on Ramos cells in clonogenic assays (F. M. Uckun et al. (1992), supra). BMLOV is much more effective than orthovanadate in the induction of Ramos cellular tyrosine phosphorylation (FIG. 12B), and this may account for the difference in clonogenic assay results. The acute monocytic leukemia line THP-1 was also strongly inhibited by BMLOV, displaying 98% inhibition of clonogenic cell growth.

TABLE 9

INHIBITION OF CLONOGENIC CELL GROWTH BY BMLOV

| Dose ($\mu$M) | Ramos | Raji | THP-1 |
|---|---|---|---|
| 0 | 4065 ± 840 | 3252 ± 672 | 6453 ± 1563 |
| 1 | 179 ± 33 | 1291 ± 283 | 1613 ± 235 |
| 5 | 7 ± 2 | 4 ± 0.6 | 127 ± 35 |
| 10 | 0 | 3 ± 0.8 | 127 ± 35 |

Figure 15A:
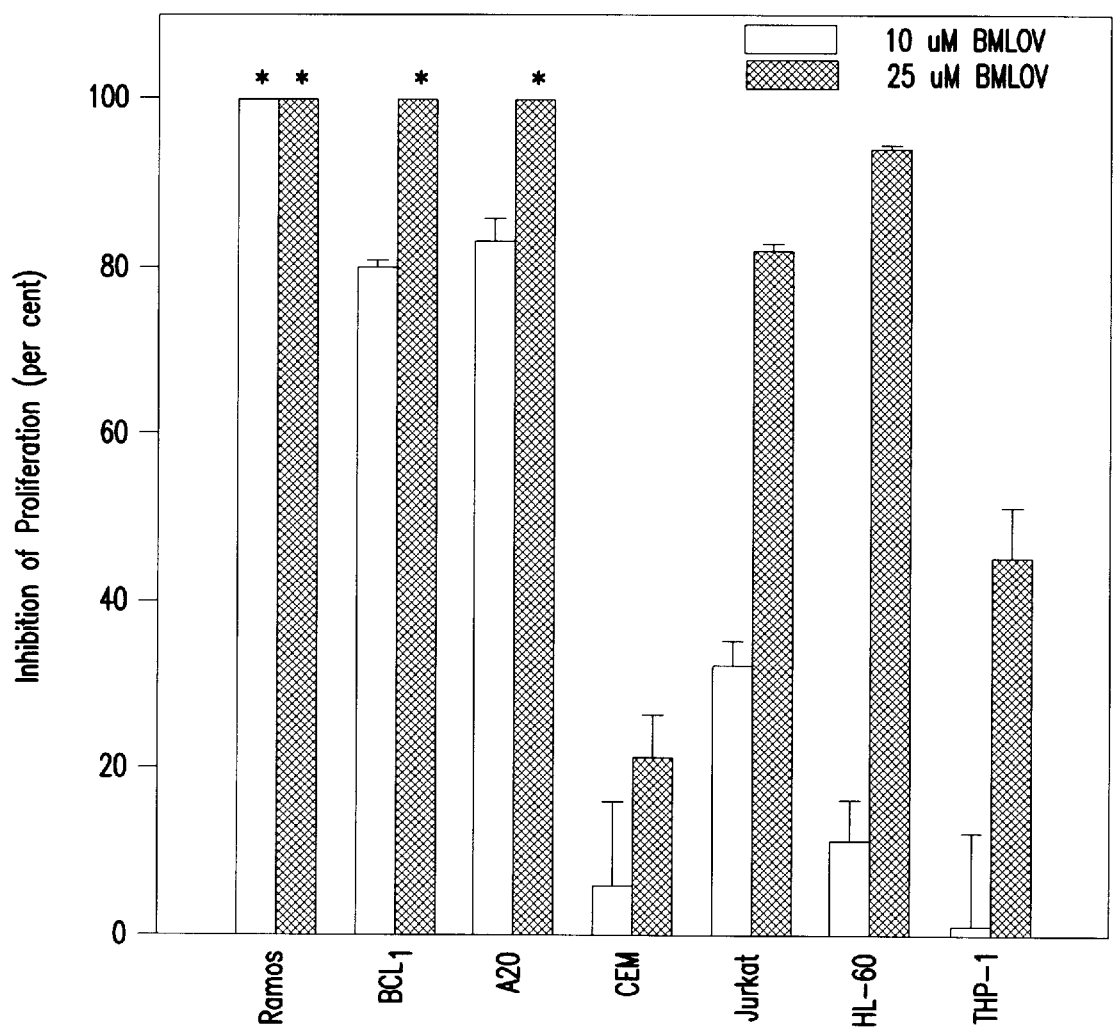
FIG. 15A is a graph showing the inhibition of cell proliferation by BMLOV; cells were grown for 5 days in the presence of 10 μM, 25 μM, or no BMLOV and proliferation was measured by [$^3$H]-thymidine incorporation; the percentage inhibition of proliferation by BMLOV is shown; assays were performed with 4 replicates and error bars show the standard error of the mean; asterisks mark conditions giving 99.9% or greater inhibition of proliferation.

Data is given in terms of colonies formed per 10,000 cells± the standard error of the mean Since other cell types of interest did not grow well in the clonogenic assay, their proliferation was examined utilizing [$^3$H]-thymidine incorporation assays (FIG. 15A). In the experiments for which data is shown in FIG. 15A, cells were grown for 5 days in the presence of 10 $\mu$M, 25 $\mu$M, or no BMLOV and proliferation was measured by [$^3$H]-thymidine incorporation. The percentage inhibition of proliferation by the BMLOV treatment is shown. Assays were performed with 4 replicates and error bars show the standard error of the mean. Asterisks (*) mark conditions giving 99.9% or greater inhibition of proliferation.

Ramos cells were highly sensitive in this assay, consistent with the results in the previous assays. Murine B cell leukemia BCL$_1$ cells and murine B cell lymphoma A20 cells were also highly sensitive to the inhibitor. Whereas all the B cell lines examined were highly sensitive to BMLOV, the myeloid and T cell lines examined were much more variable. At the lower dose of 10 $\mu$M, all the B cell lines were much more sensitive to BMLOV than were the other cell types. However, the myeloid lines HL-60 and THP-1 showed an inhibition of growth at the higher dose of 25 $\mu$M. Although only small effects were observed for CEM T cells, Jurkat T cell proliferation was substantially inhibited at 25 $\mu$M, even though apoptosis was not observed for these cells.

The extent to which the T cells were being killed by BMLOV treatment relative to the Ramos B cells was therefore examined. In FIG. 15B, cells were grown for 4 days either in the absence (control) or continuous presence of 25 $\mu$M BMLOV. Viability was measured by staining with propidium iodide followed by flow cytometric analysis as described above. The percentage of cells in each quadrant is indicated. The lower right quadrant contains the viable cells. As shown in FIG. 15B, both the CEM and Jurkat T cell leukemia lines were resistant to killing by BMLOV, with the CEM cells showing the greatest resistance. These results indicate that the inhibition of Jurkat cell proliferation was not primarily due to cell death. By contrast, the Ramos B cells were substantially more sensitive to killing by BMLOV, indicating that the induction of cell death plays an important role in the virtually complete inhibition of proliferation observed for the Ramos cells.

Figure 16A:
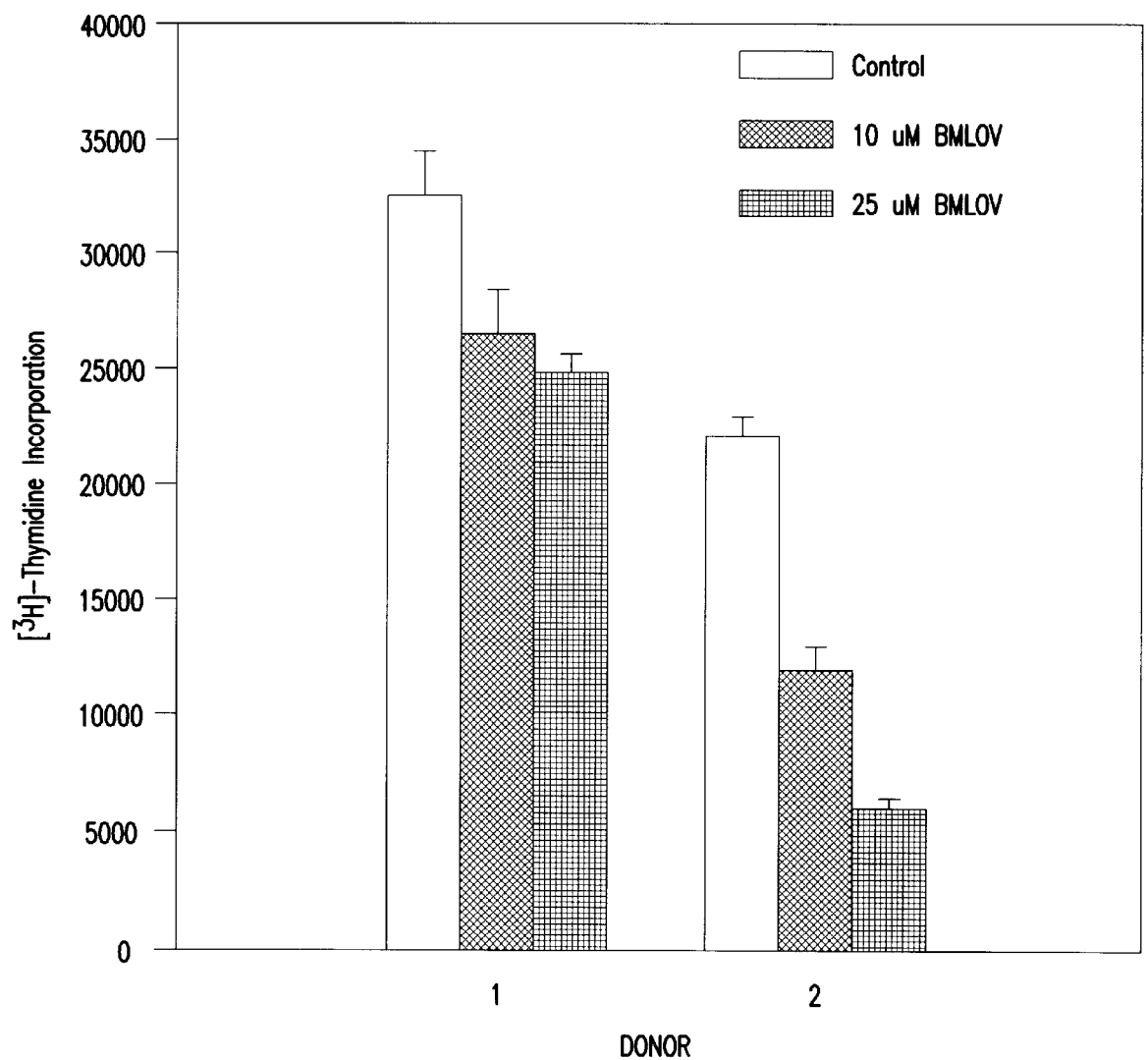
FIG. 16A is a graph showing the effects of BMLOV on thymidine incorporation in normal B cells; normal peripheral B cells were cultured in RPMI media containing 10% fetal bovine serum and with the addition of 1 μg/ml G28-5 plus 10 ng/ml IL-4 as indicated; cells were grown for 5 days in the indicated concentrations of BMLOV and proliferation was measured by [$^3$H]thymidine incorporation.

The strong effects of BMLOV on B cell leukemia and lymphoma cells suggested that the effect of BMLOV on the growth of normal peripheral B cells be studied (FIG. 16A). Normal peripheral B cells require a mitogenic stimulus to grow, so the combination of anti-CD40 monoclonal antibody plus IL-4 was employed to induce proliferation, a combination that is known to result in prolonged proliferation (J. Banchereau et al., "Long-Term Human B Cell Lines Dependent on Interleukin-4 and Antibody to CD40," Science 251:70–72 (1991)). In FIG. 16A, normal peripheral B cells were cultured in RPMI media containing 10% fetal bovine serum and with the addition of 1 μg/ml G28-5 plus 10 ng/ml IL-4 as indicated. Cells were grown for 5 days in the indicated concentrations of BMLOV and proliferation was measured by [$^3$H]-thymidine incorporation. BMLOV treatment inhibited proliferation in a dose-dependent manner, but there was considerable variation in sensitivity between cells from two different donors (FIG. 16A). Nonetheless, at a dose of 10 μM, the inhibition of proliferation of the normal B cells was markedly less than the strong inhibition observed for the transformed B cell lines (FIG. 15A).

Figure 16B:
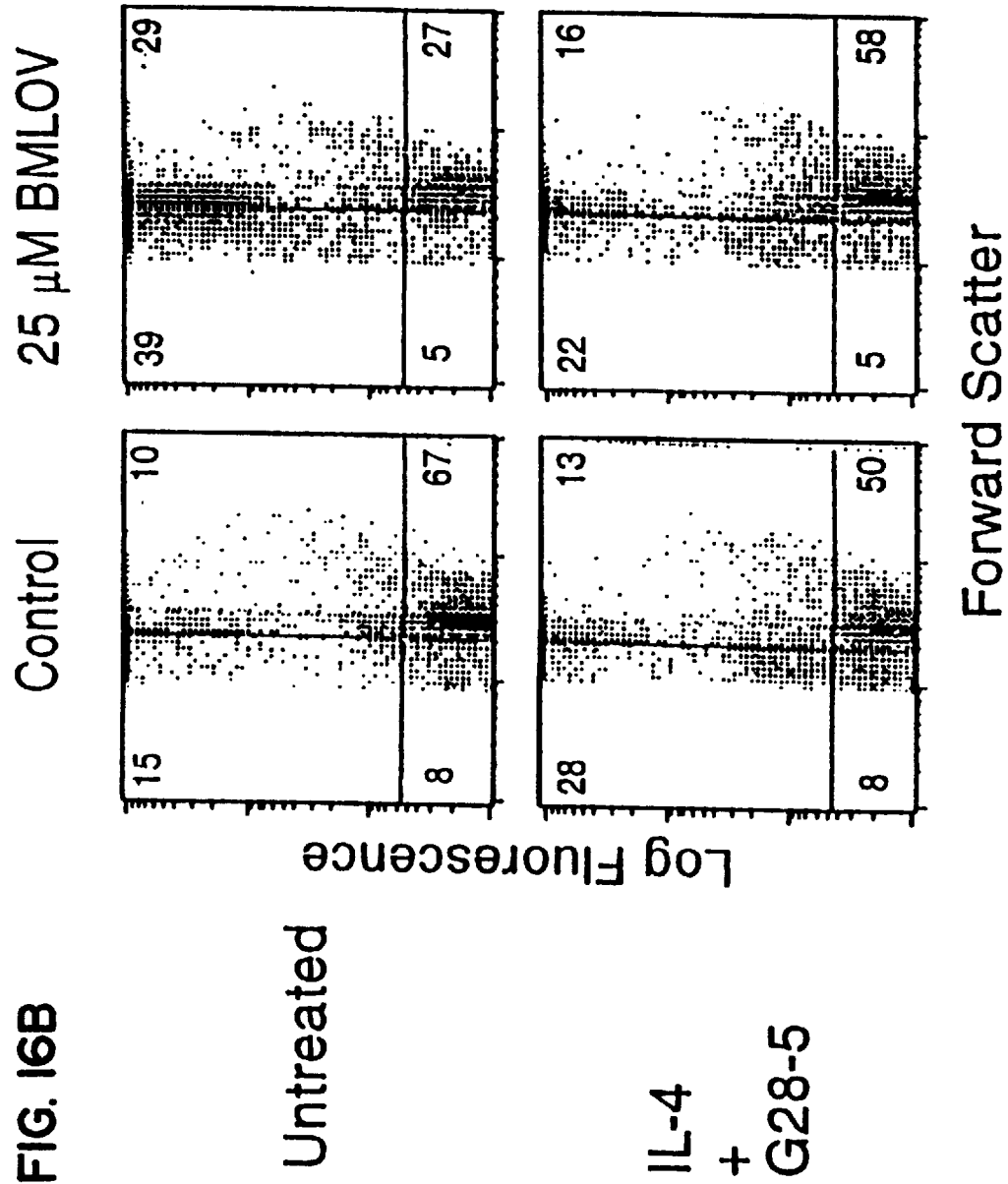
FIG. 16B shows graphs of flow cytometric results to determine the viability of normal B cells after growth in the presence of BMLOV; normal peripheral B cells were grown for 4 days with the indicated concentrations of BMLOV; viability was measured by staining with propidium iodine followed by cytometric analysis as in FIG. 15B.

In addition to promoting B cell proliferation, anti-CD40 antibodies are known to protect B cells in germinal centers from undergoing apoptosis (Y. Liu et al., "Mechanism of Antigen-Driven Selection in Germinal Centres," *Nature* 342:929–931 (1989)). The combination of IL-4 plus anti-CD40 has been reported to be more effective than either treatment alone in protecting B cells from apoptosis induced by hypercross-linking of surface IgM or IgD receptors (S. L. Parry et al., "Hypercross-linking Surface of IgM or IgD Receptors on Mature B Cells Induces Apoptosis that Is Reversed by Costimulation with IL-4 and Anti-CD40," *J. Immunol.* 152:2821–2829 (1994)). Accordingly, it was examined whether BMLOV induced cell deaths in the normal B cells (FIG. 16B). In FIG. 16B, normal peripheral B cells were grown for 4 days with the indicated concentrations of BMLOV and then stained with propidium iodine and analyzed for viability by flow cytometry. The percentage of cells in each quadrant is indicated. The lower right quadrant contains the viable cells. In the absence of any treatment, 67% of the normal B cells remained viable after 4 days in culture, whereas only 27% of the cells were viable following treatment with BMLOV (FIG. 16B). Treatment with G28-5, an anti-human CD40 monoclonal antibody, plus IL-4 protected the cells from the BMLOV induced death, with 58% of the cells remaining viable as opposed to 50% viability observed without BMLOV. In contrast to these results, treatment with combinations of anti-CD20 plus anti-CD40, phorbol ester plus IL-4, or phorbol ester plus anti-CD40 did not protect the cells from BMLOV induced death, even though these combinations are mitogenic for B cells (E. A. Clark & J. A. Ledbetter (1986), supra). Taken together, these results indicate that BMLOV can inhibit B cell growth in the absence of inducing cell death and suggest that BMLOV induced death can be blocked by appropriate biological stimulation that is known to protect against activation-induced cell death in vivo.

These results can be interpreted in view of the role of activation induced cell death in lymphocyte development. Activation induced cell death is extremely important to lymphocyte development, acting to remove self-reactive immature lymphocytes. Immature lymphocytes whose antigen receptors bind self antigen strongly and give a strong activation signal are eliminated by apoptosis (D. R. Green et al. (1992), supra). When lymphocytes mature, productive activation requires not only the primary stimulation of the cells' antigen receptor, but also costimulatory signals. In T cells, the binding of CD28 by its ligands of the B7 family serves this costimulatory role, whereas in B cells, costimulation occurs via binding of CD40 to its ligand gp39 (E. A. Clark & J. A. Ledbetter, "How B and T Cells Talk to Each Other," *Nature* 367:425–428 (1994)). In B cells, CD40 plays several important roles, promoting proliferation, preventing apoptosis of germinal center B cells, and promoting immunoglobulin class-switching. In the absence of costimulation, lymphocytes that receive only antigen receptor stimulation become non-responsive or anergic and their growth is inhibited (E. A. Clark & J. A. Ledbetter (1994), supra).

Antigen receptor signal transduction in T cells by the T cell receptor or in B cells via the B cell receptor involves tyrosine kinase activation and phosphorylation of substrates as early and essential steps (A. Weiss & D. R. Littman, "Signal Transduction by Lymphocyte Antigen Receptors," *Cell* 76:263–274 (1994)). In this study a PTP inhibitor was employed that induced tyrosine phosphorylation in B cell lines in the absence of receptor ligation. It was observed that BMLOV selectively induces apoptosis in B cell lines and in cells of myeloid linkage but not in T cell lines or in a colon carcinoma cell line. In addition, cellular proliferation was strongly inhibited in the B cell lines, but was less strongly inhibited in cells of T cell or myeloid linkage. Both the growth inhibition and selective induction of apoptosis may arise from the effects of PTP inhibition on the tyrosine phosphorylation signal pathways that regulate lymphocyte responses.

These results suggest that the accumulation of tyrosine phosphorylated proteins in B cells treated with a phosphatase inhibitor such as BMLOV leads to apoptosis via a mechanism similar to activation-induced cell death. The pattern of cellular tyrosine phosphorylation induced by BMLOV treatment of the B cells was quite similar to that induced by anti-μ stimulation of the B cell receptor (FIG. 12A). Thus, BMLOV treatment appears to result in the accumulation of many of the same tyrosine phosphorylated species as are found after antigen receptor stimulation.

The tyrosine phosphorylation response of the cell lines examined was well correlated with the apoptotic response of the cells. All the B cell lines examined displayed both a strong tyrosine phosphorylation response and induction of apoptosis, whereas the T cell line showed little tyrosine phosphorylation response or apoptosis. HL-60 cells, which underwent apoptosis in response to BMLOV, also showed a tyrosine phosphorylation response to that compound. The ability of anti-CD40 plus IL-4 stimulation to protect B cells from BMLOV induced cell death also supports the hypothesis of activation induced cell death, since that combination has been previously shown to be highly effective in blocking B cell receptor induced cell death even when it is triggered by a maximal stimulation such as hypercross-linking of surface Ig (S. L. Parry et al. (1994), supra).

The reason for the selectivity of BMLOV effects on B cell versus T cells or other cell types remain to be identified. B cells might have higher levels of basal tyrosine kinase activity and therefore require higher levels of PTP activity to maintain most substrates in a non-phosphorylated state, making the cells more susceptible to PTP inhibition. Alternatively, the PTPs regulating B cell tyrosine phosphorylation may be more sensitive to BMLOV. It is likely that CD45 plays an important role since immature B cells negative for CD45 are much more sensitive to apoptosis induced by anti-IgM stimulation (M. Ogimoto et al., "Negative Regulation of Apoptotic Death in Immature B Cells by CD45," *Inter. Immunol.* 6:647–654 (1994)). The induction of apoptosis in cells by accumulation of tyrosine phosphorylation requires that the cells have such a signal pathway in place capable of inducing apoptosis. Although such signal pathways are known in lymphocytes, they have not been reported for most other cell types, such as colon cells. For example, BMLOV can weakly induce tyrosine phosphorylation in H3347 carcinoma cells, but the cells do not undergo apoptosis, and there is no reported example of tyrosine phosphorylation dependent signals inducing apoptosis in colon cells. The expression of oncogenes and tumor suppressor genes might also be expected to influence the activity of cells to PTP inhibitor induced apoptosis. HL-60 cells lack an intact p53 gene, while Raji cells have a mutated p53 allele (M. B. Kastan et al., "Participation of p53 Protein in the Cellular Response to DNA Damage," *Cancer Res.* 51:6304–6311 (1991), so wild type p53 does not appear to be essential for BMLOV induced apoptosis or inhibition of clonogenic cell growth.

Recent studies have shown that radiation and a wide variety of chemotherapy agents act to induce apoptosis in tumor cells with the sensitivity of the tumors to induction of apoptosis being well correlated with the prognosis for successful therapy (D. E. Fisher, "Apoptosis in Cancer Therapy: Crossing the Threshold," *Cell* 78:539–542 (1994)). The tumor suppressor p53 plays a major role in this sensitivity, particularly in cases where DNA damage due to radiation or chemotherapeutic drugs appears to trigger apoptosis, even when the level of such damage would not be lethal in itself (D. E. Fisher (1994), supra). The selective induction of apoptosis in tumors by means other than DNA damage would thus of potential value in cancer therapy. One approach would be to target those malignant cell types that retain the signal pathways that induce apoptosis in their normal precursor cells. These results suggest that phosphotyrosine phosphatases play an important role in the regulation of cellular proliferation and apoptosis in lymphocytes. Phosphotyrosine phosphatase inhibitors such as BMLOV may potentially provide a new approach in the treatment of leukemia or lymphoma by selectively inducing apoptosis and preventing clonogenic cell growth.

Most investigations of pharmacologic agents to control cellular tyrosine phosphorylation are focused on inhibitors of tyrosine kinases rather than phosphotyrosine phosphatases. These findings on BMLOV indicate that inhibition of PTP activity can be of value in a variety of biological systems. In addition, the properties of agents such as BMLOV would be expected to make them useful research tools for the study of receptor mediated tyrosine kinase signal transduction, kinase activation, and tyrosine phosphorylation dependent signal events such as calcium mobilization. These agents could also therefore be used to screen for therapeutic agents and have diagnostic potential, because the response of B cells is important to monitor in a variety of clinical conditions.

EXAMPLE 16

Biological Activity of Sodium (1,10-Phenanthroline) Oxodiperoxovanadium (V) ("pV (phen)"

The biological activity of sodium (1,10-phenanthroline) oxodiperoxovanadium (V) ("pV(phen))" was examined. This compound has been reported to be a PTP inhibitor and to normalize glucose levels in diabetic animals. This compound is substantially more potent than BMLOV in biological assays and has activity towards additional cell types, particularly T cells, although it retains a high level of activity with respect to B cells.

The inhibition of murine leukemia and lymphoma cells is shown in Table 10. The cell lines A20, 70Z-3, L1210, and P388D were used. A20 is a B cell lymphoma cell line; 70Z/3 is a B cell leukemia cell line; L1210 is a T cell leukemia cell line; and P388D is a myeloid leukemia cell line. The cells were grown for 5 days in the presence of pV(phen) and pulsed with [$^3$H]-thymidine on day 5. The extent of DNA synthesis was then determined by counting the radioactivity incorporated into the cells, as in Example 5, supra. The data shown in Table 10 show that thymidine incorporation into these cells was almost completely inhibited by even the lowest dose of pV(phen), 3 μM. The effects on L1210 cells and P388D cells are particularly noteworthy because these cell lines have been extensively used by the National Cancer Institute to identify anti-cancer drugs.

TABLE 10

| Dose, | INHIBITION OF MURINE LEUKEMIA AND LYMPHOMA CELL PROLIFERATION BY pV(phen) | | | |
|---|---|---|---|---|
| | Cell Lines: | | | |
| μM | A20 | 70Z/3 | L1210 | P388D |
| 0 | 153610 ± 30573 | 80453 ± 4885 | 641698 ± 86702 | 317314 ± 34298 |
| 3 | 63 ± 40 | 108 ± 67 | ND | ND |
| 5 | 73 ± 23 | 53 ± 27 | 244 ± 155 | 2513 ± 1424 |
| 10 | 76 ± 48 | 49 ± 34 | 464 ± 116 | 362 ± 60 |

ND = not done

Figure 17:
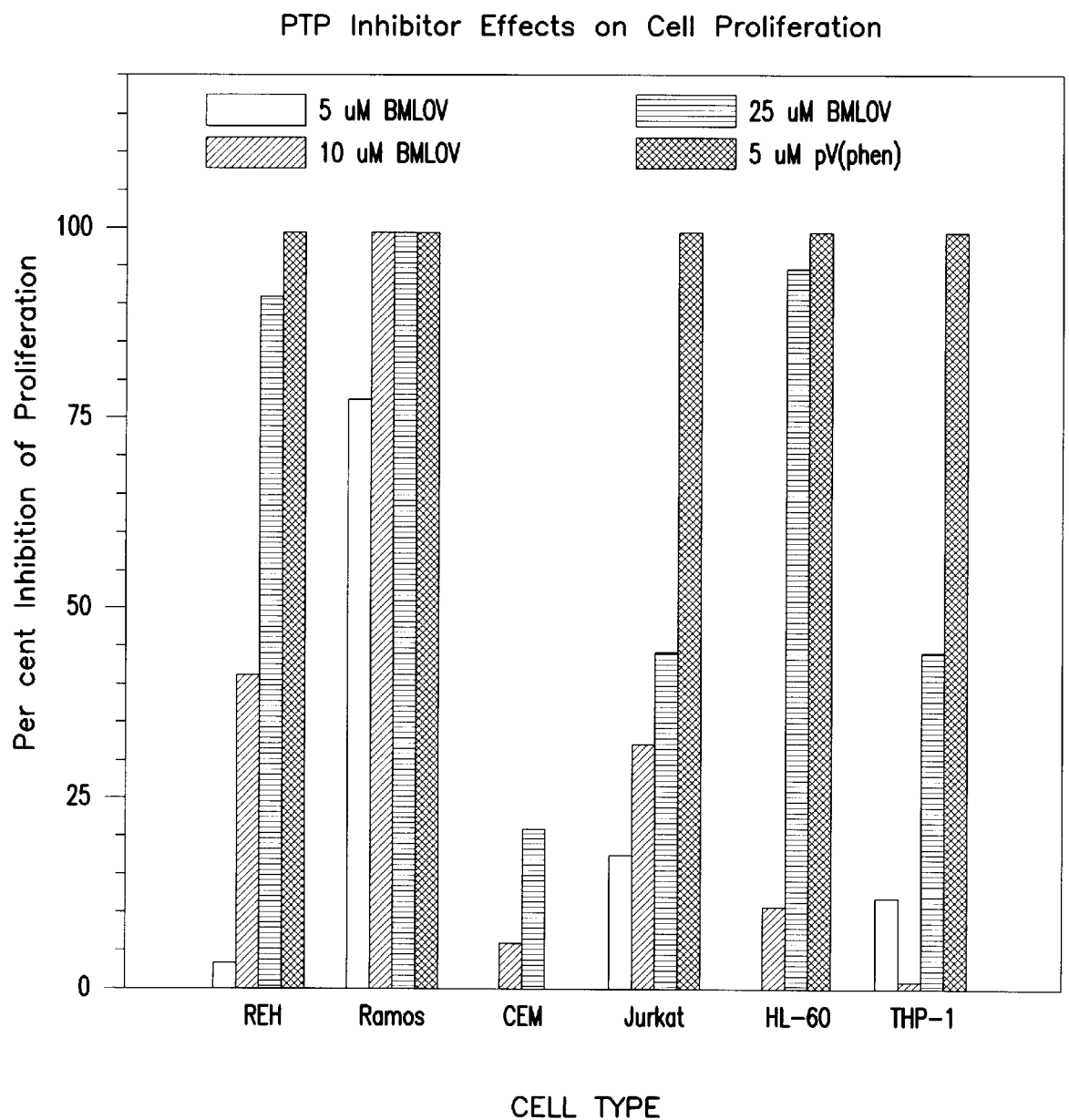
FIG. 17 is a graph of the effect of the phosphotyrosine phosphatase inhibitors BMLOV and (1,10-phenanthroline) oxodiperoxovanadium (V) (pV(phen)) on cell proliferation for REH, Ramos, CEM, Jurkat, HL-60, and THP-1 cells; cells were treated for 5 days with the concentration of inhibitor indicated and [$^3$H]thymidine incorporation was measured to determine proliferation.

Similar results are shown in FIG. 17 for the cell lines REH, Ramos, CEM, Jurkat, HL-60, and THP-1. Cells were treated 5 days with the amount of inhibitor indicated and [$^3$H]-thymidine incorporation was then measured to determine proliferation. The percent inhibition was calculated relative to untreated controls. Results are shown for three concentrations of BMLOV (5 μM, 10 μM, and 25 μM and 5 μM of pV(phen)). These results indicate that pV(phen) inhibits all cell types studied including cells of both B and T lineage.

The effect of the variation of treatment time with pV(phen) on the inhibition of proliferation in Ramos cells is shown in Table 11. These cells were grown in pV(phen) for the indicated times, washed, and then grown in fresh media for the balance of the 5-day assay. These cells were pulsed with [$^3$H]-thymidine on day 5.

TABLE 11

TREATMENT TIME DEPENDENCE OF INHIBITION OF
PROLIFERATION OF RAMOS CELLS BY pV(phen)

[³H] Thymidine Incorporation, cpm

| Dose, $\mu$M | 4 hr | 8 hr | 24 hr | 5 d |
|---|---|---|---|---|
| 0  | 622500 ± 57340 | 492342 ± 49255 | 517355 ± 25668 | 516868 ± 20323 |
| 1  | 540438 ± 86014 | 444806 ± 20361 | 396533 ± 16116 | 1969 ± 1295 |
| 5  | 502956 ± 20963 | 351849 ± 7357  | 312 ± 83       | 615 ± 268 |
| 10 | 554511 ± 10077 | 185021 ± 11112 | 1862 ± 1461    | 982 ± 519 |
| 25 | 433034 ± 74272 | 877 ± 93       | 399 ± 231      | 651 ± 295 |

These results indicate that the response in Ramos cells depends on both the treatment time and the dosage. After 8 hours of treatment with pV(phen), substantially complete inhibition was seen only at the highest dosage level, 25 $\mu$M; after 24 hours of treatment, substantially complete inhibition of proliferation was seen even at a 5 $\mu$M dose. If the dosage is maintained for the full 5-day treatment, even 1 $\mu$M of pV(phen) was sufficient to induce at least a 99% inhibition of proliferation measured by thymidine incorporation.

Figure 18:
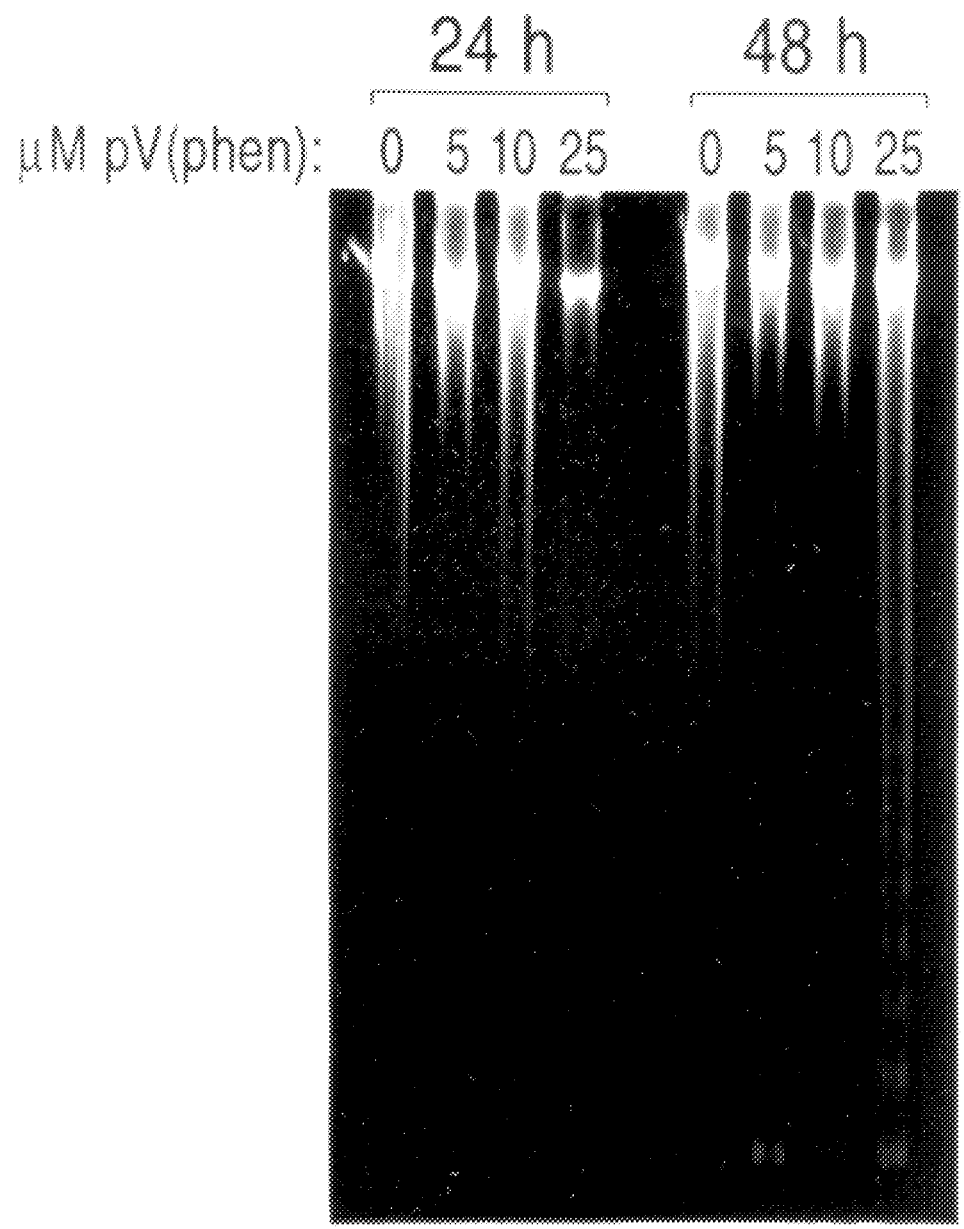
FIG. 18 is a photograph of a stained electropherograms on agarose gels of DNA from L1210 murine T cell leukemia cells treated with the indicated concentrations of p(V)phen for the indicated times, showing the apoptosis induced as fragmentation of the DNA.

The induction of apoptosis in L1210 cells by pV(phen) is shown in FIG. 18. L1210 murine T cell leukemia cells were treated with the indicated concentrations of pV(phen) for the indicated times and the DNA was examined by gel electrophoresis as in Example 3. The fragmentation of DNA demonstrates apoptosis.

Figure 19:
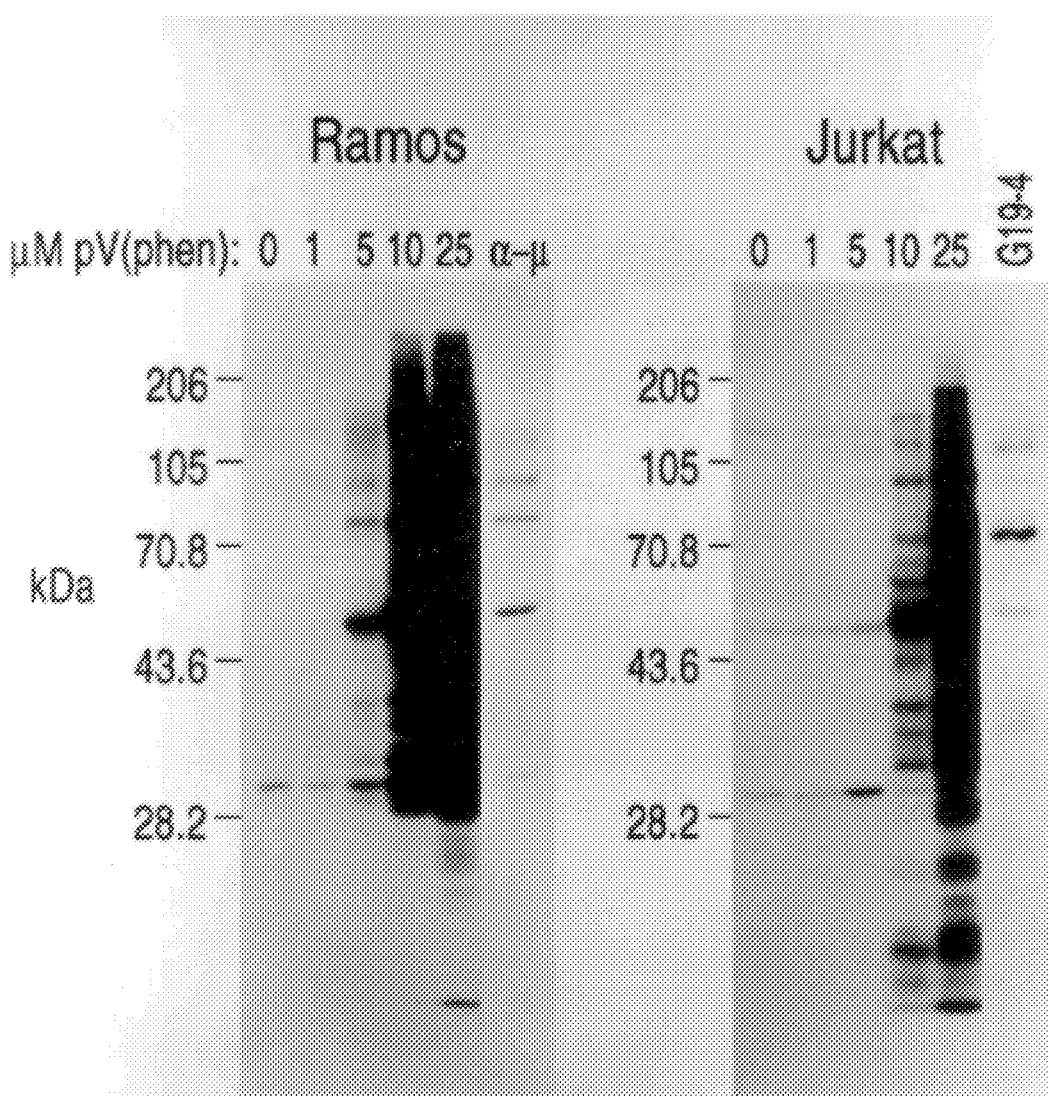
FIG. 19 is a photograph of an anti-phosphotyrosine Western blot similar to those in FIGS. 1A–1C showing the induction of tyrosine phosphorylation by pV(phen); Ramos B cells and Jurkat T cells were treated with the indicated concentrations of pV(phen) for 16 hours or with anti-μ (to cross-link surface immunoglobulins) for 1 minute or with monoclonal antibody G19-4 (anti-CD3) for 1 minute; the cells were then lysed and cellular tyrosine phosphorylation was examined by an anti-phosphotyrosine Western blot of the cellular proteins.

In FIG. 19, the induction of phosphotyrosine by pV(phen) is shown in Ramos and Jurkat cells. Ramos B cells and Jurkat T cells were treated with the indicated concentrations of pV(phen) for 16 hours or with anti-$\mu$ (to crosslink surface immunoglobulin) for 1 minute or with mAb G19-4 (anti-CD3) for 1 minute. The cells were then lysed and cellular tyrosine phosphorylation was examined by anti-phosphotyrosine Western blotting of the cellular proteins following SDS-polyacrylamide gel electrophoresis. These results indicate a high level of tyrosine phosphorylation induced by pV(phen).

Figure 20:
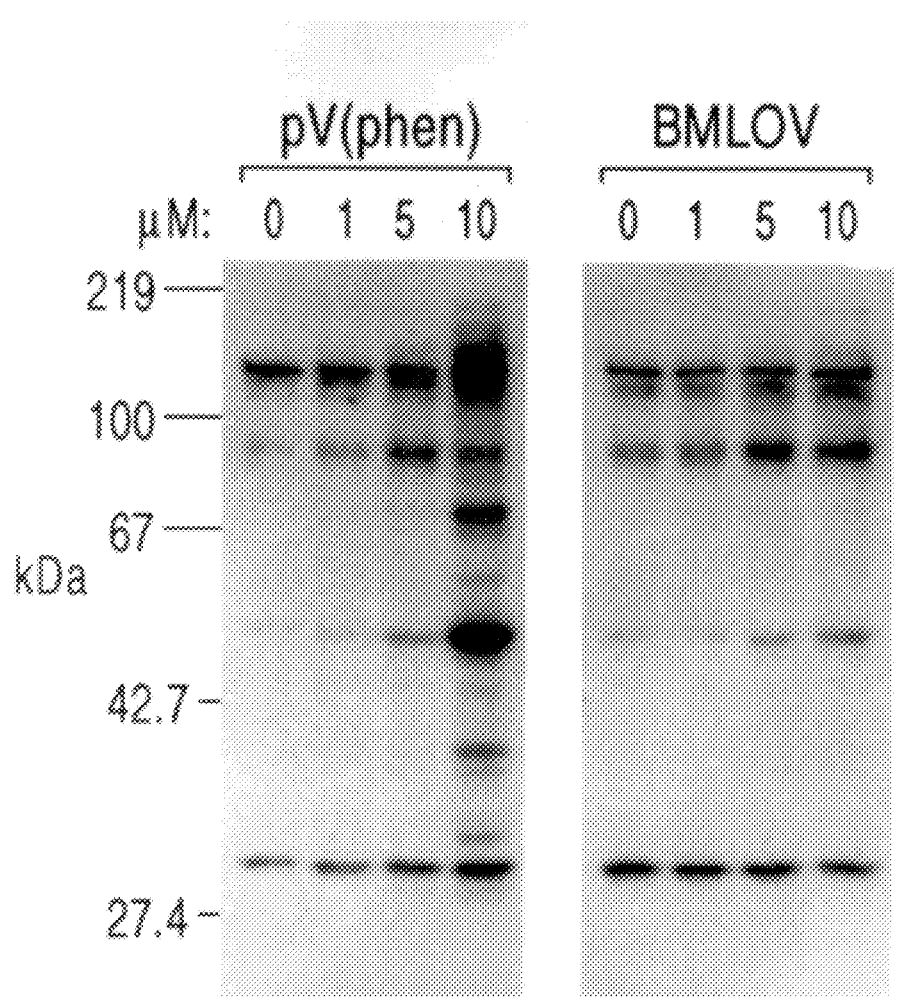
FIG. 20 is a comparison of the tyrosine phosphorylation induced by pV(phen) and BMLOV; Ramos B cells were treated with the indicated concentrations of BMLOV or pV(phen) for 16 hours; the cells were then lysed and Western blotting performed as in FIG. 19.

Similarly, a comparison of the tyrosine phosphorylation induced by pV(phen) and BMLOV is shown in FIG. 20. Ramos B cells were treated with the indicated concentrations of BMLOV or pV(phen) for 16 hours. The cells were then lysed and cellular tyrosine phosphorylation was examined by an anti-phosphotyrosine Western blot of the cellular proteins following SDS-polyacrylamide gel electrophoresis. These results indicate that pV(phen) causes the tyrosine phosphorylation of a significantly larger group of proteins than does BMLOV, particularly at 10 $\mu$M.

Figure 21:
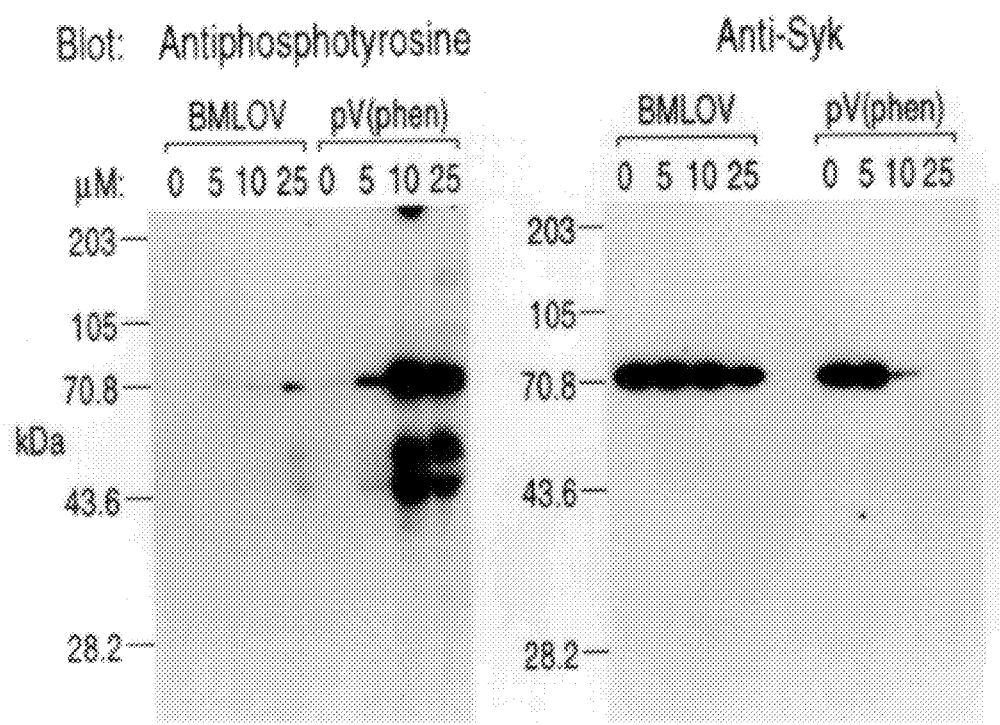
FIG. 21 shows Western blotting results indicating the response of Syk to pV(phen); Ramos B cells were treated with the indicated concentrations of BMLOV or pV(phen) for 16 hours; the cells were then lysed and the Syk tyrosine kinase was immunoprecipitated with anti-Syk antibodies; the tyrosine phosphorylation of Syk was examined by an anti-phosphotyrosine Western blot of the immunoprecipitated Syk protein following electrophoresis (shown at left); the amount of Syk protein recovered was determined by anti-Syk Western blot of identical samples (shown at right)

BMLOV is known to inhibit Src-family tyrosine kinases. In contrast, pV(phen) not only inhibits PTP but also activates at least one type of tyrosine kinase, the Syk-family kinases. The response of Syk kinase to pV(phen) is shown in FIG. 21. Ramos B cells were treated with the indicated concentrations of BMLOV or pV(phen) for 16 hours. The cells were then lysed and the Syk tyrosine kinase was immunoprecipitated with anti-Syk antibodies. The tyrosine phosphorylation of Syk was examined by an anti-phosphotyrosine Western blot of the immunoprecipitated Syk protein following SDS-polyacrylamide gel electrophoresis (shown at left). The amount of Syk protein recovered was determined by anti-Syk Western blotting of identical samples (shown at right). FIG. 21 demonstrates that pV(phen) strongly induces tyrosine phosphorylation of the Syk tyrosine kinase, whereas only very slight tyrosine phosphorylation of Syk is observed following BMLOV treatment. The anti-Syk Western blot of identical samples at the right shows that the recovery of Syk as a protein is markedly reduced following the pV(phen) treatment, so the specific activity of Syk tyrosine phosphorylation is even greater than is apparent from the strong tyrosine phosphorylation shown at the left.

Analysis of the human T cell leukemia cell lines CEM and Jurkat by propidium iodide staining followed by flow cytometry demonstrates that 10 $\mu$M pV(phen) kills 98% of these leukemia cells in two days and all the cells by three days.

Animal studies with BALB/C mice have shown that the maximum tolerated dose is 1 ml of a 1 mM solution in saline by intraperitoneal (i.p.) injection, as tested in 18–20 g mice. This dose is well tolerated when administered every 2 days for 2 weeks. In contrast, a dose of 2 mM resulted in some deaths. However, this dose is substantially greater than that required to induce inhibition of proliferation of susceptible lymphoid and myeloid cells.

The animal studies have shown that pV(phen) specifically acts against lymphocytes in vivo. BALB/C mice received one dose of pV(phen) i.p. and their blood was examined 24 hr later. As shown in Table 12, the number of peripheral blood lymphocytes in the treated animals was markedly reduced. This effect on lymphocytes was specific in that the number of neutrophils was substantially increased, whereas no consistent effect was observed for monocytes. The increase in neutrophils provides a significant advantage for the PTP inhibitors relative to many cytotoxic drugs that deplete neutrophils, a serious side effect of cytotoxic drugs in patients. The depletion of lymphocytes also suggest that compounds such as pV(phen) can be of use in the treatment of autoimmune diseases such as arthritis or inflammatory bowel disease.

TABLE 12

EFFECT OF pV(phen) ON LEUKOCYTE COUNTS IN MICE

| Animal No. | Dose | Absolute Counts: | | | |
|---|---|---|---|---|---|
| | | Lymphocyte | Neutrophil | Monocyte | Eosinophil |
| 1 | 0       | 8099 | 356  | 178 | 267 |
| 2 | 0       | 6003 | 690  | 69  | 138 |
| 3 | 1 $\mu$M | 3848 | 1525 | 488 | 244 |
| 4 | 1 $\mu$M | 1612 | 858  | 104 | 26  |
| 5 | 2 $\mu$M | 1560 | 1872 | 390 | 78  |
| 6 | 2 $\mu$M | 2511 | 5508 | 0   | 81  |

EXAMPLE 17

In Vivo Antitumor Activity of pV(phen)

The compound pV(phen) was tested for its antitumor activity in vivo. A summary of the antitumor test results is shown below in Table 13. In the i.p. M109 murine lung carcinoma model (Experiment No. 330; Table 13), consecutive daily i.p. injections each day from day 1 to 5 were effective in achieving an active result. A dose level of 12 kg per injection resulted in a maximum T/C value of 144%. Values of T/C greater than or equal to 125% are considered to be indicative of activity in this test format. In an attempt to confirm this result, the pV(phen) was retested on the same treatment schedule but with slightly escalated doses (Experiment No. 333; Table 13). A maximum T/C of 143%, consistent with the first result, was obtained.

Against i.p. B16 murine melanoma (Experiment No. 799; Table 13) consecutive daily i.p. injections administered for each day from day 1 to day 9 resulted in a maximum T/C of 152% at a maximum tolerated dose (MTD) of 6 mg/kg per injection. The cumulative dose MTD of 54 mg/kg was similar to the 60 mg/kg cumulative MTD observed in the last M109 experiment.

Against the i.p. implanted P388 murine leukemia (Experiment No. 8457; Table 13), single i.p. doses of greater than or equal to 32 mg/kg of pV(phen) were excessively toxic, i.e. lethal, and the next lower dose tested, 8 mg/kg was inactive in this assay format (T/C<125%). In another P388 trial (Experiment No. 8459; Table 13) consecutive daily i.p. injections each day from days 1 to 5 likewise proved ineffective at doses as great as 12 mg/kg per injection and considered to be a MTD.

Intermittent injections of pV(phen), e.g., 8 mg/kg failed to achieve an active result in this test format against the i.p. implanted ras transformed rat-1 tumor model (Experiment No. 6; Table 13).

Finally, pV(phen) was tested against subcutaneously implanted human ovarian carcinoma, A2780, in Experiment No. 54, using a treatment schedule of once daily for 9 days. Treatments (i.p.) were begun on day 10 post implant when the tumors were small but definite, e.g. 50–60 mg, at the MTD of 5 mg/kg per injection (cumulative dose of 45 mg/kg). A delay in primary tumor growth of 4.0 days was achieved, reflective of 0.4 log cell kill (LCK), a basically inactive result in this assay format.

These results are of major importance because activity considered significant by generally-applied standards was seen in two types of tumors in vivo. This indicates a significant potential for antitumor activity of p(V)phen.

TABLE 13

In Vivo Antitumor Test Results on pV(phen) Treatment

| Tumor, site | Expt. No. | OD[a] (mg/kg/inj) | Schedule, route | Max. % T/C [T-C, days: LCK] |
|---|---|---|---|---|
| A2780 | 54 | 12 | qdx9;10, ip | [4.0:0.4] |
| B16, ip | 799 | 6[b] | qd 1→9, ip | 152 |
| M109, ip | 330 | 12 | qd 1→5, ip | 144 |
|  | 333 | 12[b] | qd 1→5, ip | 143 |
| Rat-1, ip | 6 | 8 | d.1, 4&7, ip | 110 |
| P388, ip | 8457 | 8[b] | d.1, ip | 105 |
|  | 8459 | 12[ab] | qd 1→5, ip | 118 |

[a]Or highest dose tested, or maximum tolerated dose, if inactive
[b]MTD reached.

The inactive results seen in some tests may have been due to peculiarities of administration or metabolism in vivo. Such results do not necessarily mean that the drug was ineffective under these conditions, particularly because some activity was yet seen. It is possible that the treatment regimen or route of administration could be optimized to yield significant activity in the trials that yielded inactive results in this format.

EXAMPLE 18

In Vitro Cytotoxicity of pV(phen) in a Panel of Human Tumor Cell Lines

The vanadate compound pV(phen) was tested for in vitro cytotoxicity in a panel of human tumor cell lines. The results are given in Table 14. The cell lines used were a human colon carcinoma cell line, HCT116, and two drug-resistant sublines. The HCT116(VM46) subline was selected for resistance to VM-26 and expresses the multidrug resistant (MDR) phenotype including resistance to lipophilic anticancer drugs such as paclitaxel, VP-16, VM-26, doxorubicin, and vinblastine. This cell line overexpresses P-glycoprotein, a cell surface drug efflux pump, which limits accumulation of anticancer drugs such as the ones mentioned above. The other cell line, HCT116(VP35) was selected for resistance to VP-16 and is resistant to topoisomerase II active drugs such as VP-16 and VM-26 due to reduced levels of the topoisomerase II enzyme. The compound pV(phen) was also evaluated in the ovarian carcinoma cell line A2780 and a paclitaxel resistant subline A2780-Tax22. The latter cell line, which is 18-fold resistant to paclitaxel, does not overexpress P-glycoprotein, but appears to have altered tubulin.

In the cytotoxicity assays, cells were plated and 24 hr later drugs were added and serially diluted. After 72 hr of continuous drug exposure, the tetrazolium dye XTT was added. A dehydrogenase enzyme in live cells reduces the XTT to a form that absorbs light at 450 nm which can be quantitated spectrophotometrically. The greater absorbance, the greater is the number of live cells. The results are expressed as a $IC_{50}$ which is a drug concentration required to inhibit cell proliferation (i.e., absorbance at 450 nm) to 50% of that of untreated control cells.

The compound pV(phen) had a IC value of approximately 8 $\mu$M in both the HCT116 and A2780 cell lines. Likewise, the HCT116 (VP)35 and the A2780-Tax22 resistant cell lines did not appear to be cross-resistant to the test compound. Interestingly, however, the MDR cell line HCT116 (VM46) was collaterally sensitive to the vanadate compound, showing greater sensitivity than the parent. This result is contrasted with the effect of paclitaxel on these cell lines; the MDR subline was 75-fold more resistant than paclitaxel than was the parent line HCT116 (Table 14).

In other results, it was shown that the MDR cell line MCF-7-AdrR had a similar level of increased sensitivity to pV(phen) relative to the parental cell line. In previous studies it was shown that cisplatin was also collaterally sensitive in MDR cells, although not to the degree shown for pV(phen). The degree of collateral sensitivity for cisplatin MDR cells was lower than for pV(phen). What if any connection these two drugs have is unclear. P-glycoprotein is known to be phosphorylated by protein kinase C, and modulation of protein kinase C activity can affect the level of MDR. However, it is unclear how the level of phosphorylation P-glycoprotein would affect the sensitivity to pV(phen) alone.

This showing of collateral sensitivity is an unexpected result which holds out considerable promise, particularly for treatment of malignancies that are resistant to other drugs. In any case, these results are highly significant in showing killing of tumor cells in tests using cell lines recognized in the art as models for human tumors. This data on cell lines is recognized in the art as predictive of utility for the treatment of tumors.

TABLE 14

Results of Testing pV(phen) on Tumor Cell Lines

| Compound | HCT116 | HCT116(VM)46 | HCT116(VP)35 | A2780 | A2780/Tax22 |
|---|---|---|---|---|---|
| pV (phen) | 8.4 | 2.0 (0.2)[2] | 7.2 (0.9) | 8.2 | 7.5 (0.9) |
| Paclitaxel | 0.003 | 0.226 (75) | 0.002 (0.7) | 0.004 | 0.075 (18) |

[1]Cytotoxicity determined after 72 hr drug exposure by XTT assay.
[2]Value in parenthesis is fold resistance relative to parental cell line.

EXAMPLE 19

Lineage-Specific Alteration of Antigen Receptor Signal Transduction by BMLOV

Materials and Methods

Materials and methods were generally as in Example 15, supra, with the following additions:

Cells and reagents.

Human peripheral blood T lymphocytes and PHA-induced human T cell blasts were prepared from peripheral blood mononuclear cells from normal volunteers as previously described (G. L. Schieven et al., *J. Biol. Chem.* 269:20718–20726 (1994)). Anti-human Syk and ZAP-70 were from Upstate Biotechnology (Lake Placid, N.Y.) and anti-CD25 was from Becton-Dickinson. Anti-PLCγ2 has been previously described (X. R. Yao & D. W. Scott, *Immunol. Rev.* 132:163–186 (1993)).

Rabbit anti-human IgM F(ab')$_2$ was from Jackson Immuno Research Labs (Westgrove, Pa.). IL-2 and IL-4 were from R&D Systems (Minneapolis, Minn.).

Measurement of Cytoplasmic Calcium Concentration

Ca$^{2+}$ responses were measured using indo-1 (Molecular Probes, Eugene, Oreg.) and a model 50 HH/2150 flow cytometer (Ortho, Westwood, Mass.) as previously described (P. S. Rabinovitch et al., *J. Immunol.* 137:952–961 (1986)). The histograms were analyzed by programs (Cicero, Cytomation Inc., Ft. Collins, Colo.) that calculate the mean indo-1 violet/blue fluorescence ratio versus time. There are 100 data points on the X (time) axis for all flow cytometric data.

TUNEL Analysis of Fragmented DNA.

TUNEL (TdT-mediated dUTP-biotin nick end labeling) staining for the in situ detection of fragmented DNA was as previously described (Y. Gavrieli et al., *J. Cell Biol.* 119:493–501 (1992)) with modification to permit detection by flow cytometry. Cells ($2 \times 10^6$) were washed with PBS and resuspended in 4% formaldehyde in PBS at 4° C. for 4 h for fixation. Cells were rinsed in PBS and permeabilized by resuspension in 70% ethanol in PBS for 1 h at 4° C. Cells were rinsed with PBS, rinsed with TdT buffer (30 mM Tris-HCl, pH 7.2, 140 mM cacodylate, 1 mM cobalt chloride) and resuspended in 150 μl TdT buffer. Biotin-dUTP (SIGMA, St. Louis, Mo.) was added to 15 μM and terminal deoxynucleotidyl transferase (TdT, Boehringer Mannheim) was added to 0.6 U/μl. DNA synthesis was for 1 h at 37° C. and was stopped by the addition of 1 ml cold PBS. Cells were rinsed twice with PBS and resuspended in 500 μl of PBS containing 5 μg of fluorescein-avidin at 4° C. for 16 h. Cells were washed twice in PBS and resuspended in 400 μl of PBS for flow cytometry. Cells were analyzed using a Becton-Dickinson FACScan flow cytometer and LYSIS analysis software.

Confocal Laser Scanning Microscopy.

Cells were fixed with 3.7% formaldehyde in PBS and permeabilized by treatment with 0.1% saponin. The fixed and permeabilized cells were then incubated in staining buffer (5% goat serum in PBS) for 1 h followed by 45 min in 1 μg/ml affinity purified rabbit polyclonal anti-phosphotyrosine antibodies (D. Dailey et al., *Mol. Cell. Biol.* 10:6244–6256 (1990)) in staining buffer. The cells were then washed three times in staining buffer, and stained with fluorescein-labeled goat anti-rabbit antibody (Molecular Probes). After washing three times in staining buffer, cells were stained for DNA with 2 μg/ml propidium iodide. A Leica GmbH confocal laser scanning microscope (CLSM) (Leica Laser Technic, Heidelberg, Germany) equipped with a krypton/argon laser (Omnichrome, Chino, Calif.), 2 double dichroic beam splitters with $\lambda_{s1}/\lambda_{s2}$ of 488/647 and 488/568 nm, 1 neutral density beam splitter (Lys Optics, Denmark), the Leica CLSM software accessories, and the Leica true color display graphics package was used to produce the confocal images.

Figure 22:
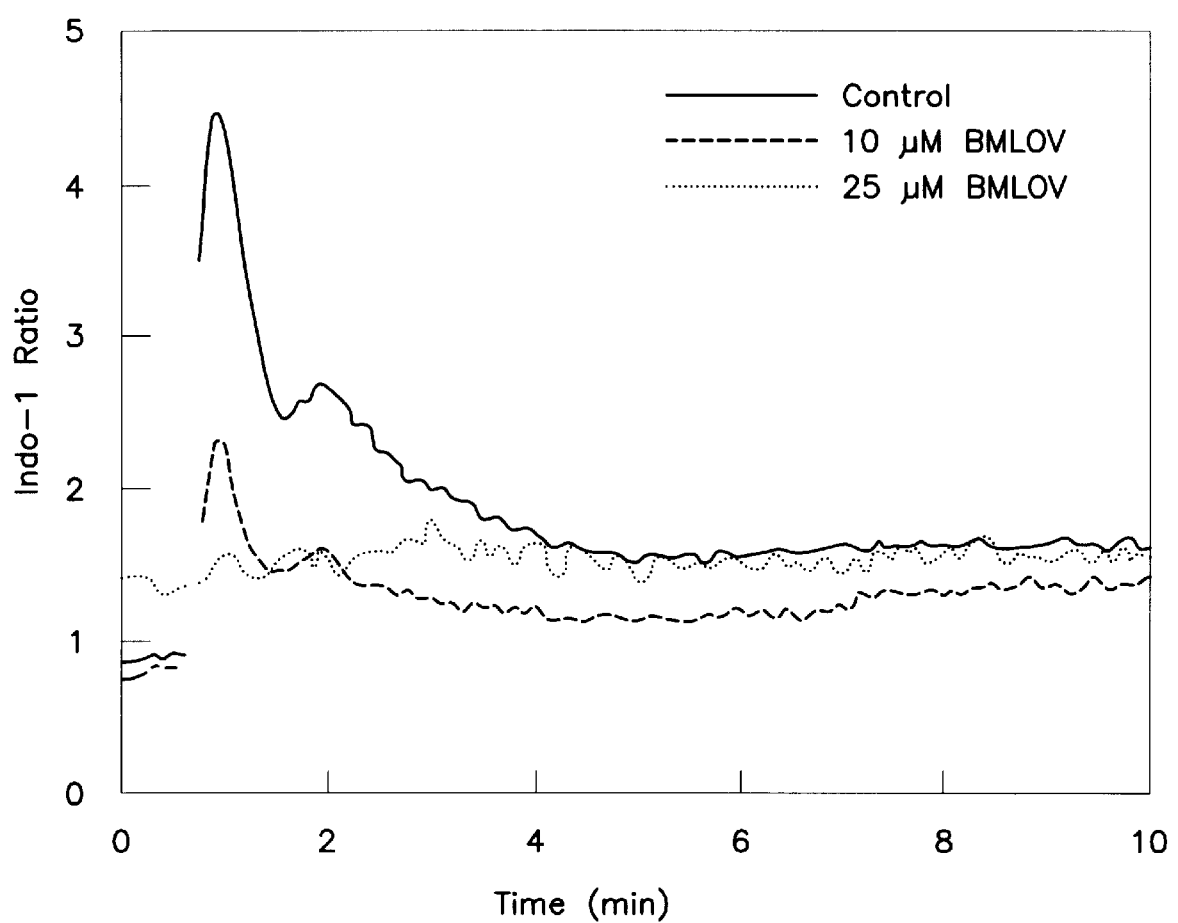
FIG. 22 shows the effect of BMLOV on the intracellular level of calcium in B cells; Ramos B cells were treated overnight with the indicated concentrations of BMLOV; the baseline level of intracellular free $Ca^{2+}$ ([$Ca^{2+}$]$_i$) was established for 1 min, and then the cells were treated with anti-human IgM F(ab')$_2$ (α-μ); the gap in the trace reflects the addition of α-μ.

The results in previous examples suggested that since BMLOV displayed significantly greater biological activity than orthovanadate, particularly in B cells, BMLOV would be a useful probe to investigate the effects of PTP inhibition on antigen receptor signal transduction in B cells. BMLOV treatment of Ramos B cell for 16 h resulted in elevation of basal Ca$^{2+}$ levels (FIG. 22). In the experiments shown in FIG. 22, Ramos B cells were treated overnight with the indicated concentrations of BMLOV. The baseline level of intracellular free Ca$^{2+}$ ([Ca$^{2+}$]$_i$) was established for 1 min, and then the cells were treated with anti-human IgM F(ab')$_2$ (α-μ). The gap in the trace reflects the addition of α-μ. An acute Ca$^{2+}$ response to the addition of BMLOV to the Ramos cells was not observed, in contrast to the rapid elevation of Ca$^{2+}$ observed following treatment with pervanadate or H$_2$O$_2$ (G. L. Schieven et al., *Blood* 82:1212–1220 (1993)); G. L. Schieven et al., *J. Biol. Chem.* 268:16688–16692 (1993)). However, Ca$^{2+}$ signals induced by cross-linking sIgM were strongly inhibited in a dose-dependent manner by the BMLOV treatment. Complete inhibition was observed in cells treated with 25 μM BMLOV.

Analysis of cellular tyrosine phosphorylation revealed that the BMLOV treatment affected both the amplitude and the timing of the cells' response to sIgM cross-linking (FIG. 22). The basal level of tyrosine phosphorylation increased in a dose-dependent manner. In cells treated with 10 μM BMLOV, the α-μ induced signal was stronger than in the control cells, and the signal was maintained at a high level at both the 5 and 30 min time points. By contrast, the control cells showed a substantial decline at 30 minutes. Cells treated with 25 μM BMLOV showed only small increases following α-μ treatment, and these occurred at late time points.

The activation state of the Syk tyrosine kinase was next examined, because Syk is a key B cell signalling kinase that shows prolonged activation following α-μ stimulation (S. J. Saouaf et al., *Proc. Natl. Acad. Sci. USA* 91:9524–9528

(1994); D. L. Burg et al., *J. Biol. Chem.* 268:2304–2306 (1994)). BMLOV treatment induced tyrosine phosphorylation of Syk in a dose-dependent manner (FIG. 23) in the absence of antigen receptor stimulation, while the amount of Syk protein remained constant (FIG. 23).

Figure 23A:
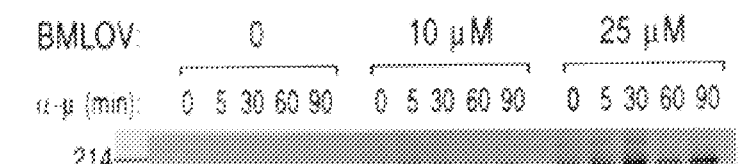
FIG. 23 shows the effect of BMLOV on the phosphorylation of Syk protein in B cells; cells were treated 16 h with BMLOV and then stimulated with α-μ for 5 min; cells were then washed and resuspended in fresh media at equal concentrations of BMLOV at 37° C.; cells were harvested and lysed at times following the initiation of α-μ stimulation as indicated; antibody binding in immunoblots was detected by ECL; Panel A shows anti-phosphotyrosine immunoblots of whole cell lysates; Panel B shows anti-phosphotyrosine immunoblots of anti-Syk immunoprecipitates prepared from the same samples; and Panel C shows recovery of Syk protein, with the blot in Panel B being stripped and reprobed with anti-Syk antibody to show recovery of Syk protein.
Figure 23B:
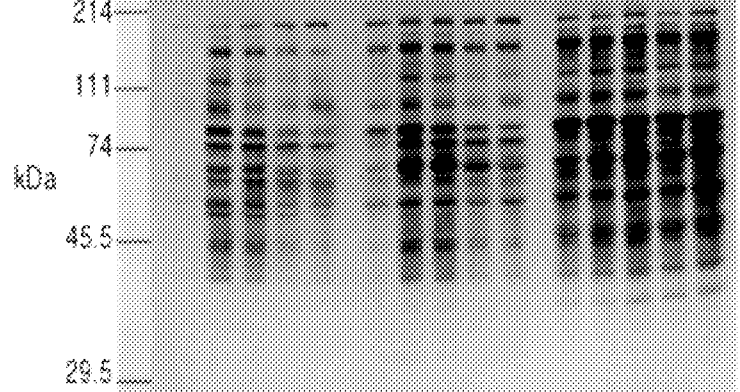
Figure 23C:

In the experiments shown in FIG. 23, cells were treated 16 h with BMLOV and then stimulated with α-μ for 5 min. Cells were then washed and resuspended in fresh media at equal concentrations of BMLOV at 37° C. Cells were harvested and lysted at times following the initiation of α-μ stimulation as indicated. Antibody binding in immunoblots was detected by ECL. Panel A shows anti-phosphotyrosine immunoblots of whole cell lysates; Panel B shows anti-phosphotyrosine immunoblots of anti-Syk immunoprecipitates prepared from the same samples; and Panel C shows recovery of Syk protein, with the blot in Panel B being stripped and reprobed with anti-Syk antibody to show recovery of Syk protein.

These results indicate that BMLOV treatment activates the Syk tyrosine kinase, since the tyrosine phosphorylation of Syk has been found to reflect the activation of its enzymatic activity (S. J. Saouaf et al. (1994), supra; D. L. Burg (1994), supra; T. Kurosaki et al., *J. Exp. Med.* 179:12725–1729 (1994)). The activation of Syk correlated well with cellular tyrosine phosphorylation. Syk was more strongly activated at the 5 and 10 min time points in the 10 μM BMLOV samples and was strongly activated at later time points in the 25 μM BMLOV samples.

Syk is essential for the tyrosine phosphorylation of PLCγ2 that leads to $Ca^{2+}$ signaling in B cells following antigen receptor stimulation (M. Takata et al., *EMBO J.* 13:1341–1349 (1994)). BMLOV treatment strongly induced the tyrosine phosphorylation of PLCγ2 and associated proteins in a dose-dependent manner (FIG. 24, Panel A) in the absence of antigen receptor stimulation, while the amount of PLCγ2 protein remained constant (FIG. 24, Panel B). In the experiments shown in FIG. 24, Ramos B cells were treated 16 h with the indicated concentrations of BMLOV and then stimulated for 2 min with α-μ. Antibody binding in immunoblots was detected by ECL. Panel A shows the anti-phosphotyrosine immunoblot of anti-PLCγ2 immunoprecipitates; in Panel B, the blot was stripped and reprobed with anti-PLCγ2 antibody to show recovery of the PLCγ2 protein. The extent of tyrosine phosphorylation of PLCγ2 induced by BMLOV was substantially more than that observed following a maximal sIgM stimulation, and no additional tyrosine phosphorylation of PLCγ2 could be induced by sIgM stimulation of BMLOV treated cells.

Taken together, these results indicate the treatment of the B cells with the PTP inhibitor BMLOV leads to activation of signal pathways normally under antigen receptor regulation, including the activation of Syk and the tyrosine phosphorylation of PLCγ2 and other cellular proteins. These results suggest that inhibition of $Ca^{2+}$ signalling by BMLOV appears to be due to activation induced desensitization, since PLCγ2 is strongly phosphorylated and basal $Ca^{2+}$ levels are elevated in the absence of receptor stimulation.

Figure 25:
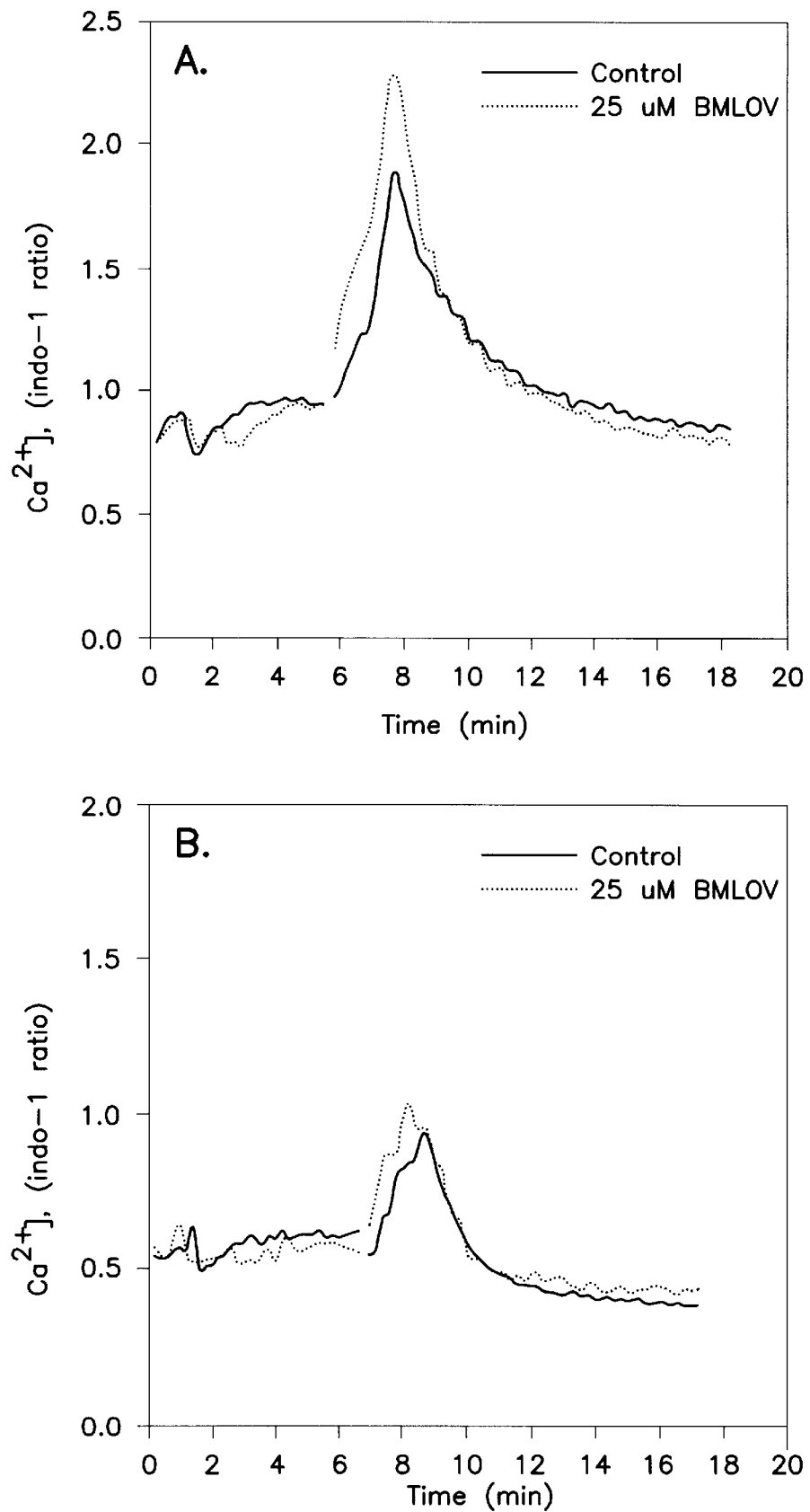
FIG. 25 shows the effects of BMLOV on $Ca^{2+}$ signaling in T cells; human PHA-induced T cell blasts were treated overnight with the indicated concentrations of BMLOV; in Panel A, the baseline level of intracellular free $Ca^{2+}$ ([$Ca^{2+}$]$_i$) was established for 1 min, and then the cells were treated with biotinylated anti-CD3 mAb (G19-4); after 5 min avidin was added (gap in the trace) to cross-link the antibody; in Panel B, assays were performed as in Panel A, but in the presence of 5 mM EGTA.

In contrast to the results observed in the B cells, $Ca^{2+}$ signaling in T cells was increased and prolonged by treatment with BMLOV (FIG. 25). In the experiments shown in FIG. 25, human PHA-induced T cell blasts were treated overnight with the indicated concentrations of BMLOV. In Panel A, the baseline level of intracellular free $Ca^{2+}$ ($[Ca^{2+}]_i$) was established for 1 min, and then the cells were treated with biotinylated anti-CD3 mAb (G19-4). After 5 min avidin was added (gap in the trace) to cross-link the antibody. In Panel B, assays were performed as in Panel A, but in the presence of 5 mM EGTA. Similar increases were observed for $Ca^{2+}$ signaling resulting from the cross-linking of CD3 with the accessory molecules CD2 or CD4. An increase also occurred in the presence of EGTA (FIG. 25, Panel B), indicating that BMLOV increased the release of $Ca^{2+}$ from intracellular stores. BMLOV had little effect on basal or T cell receptor induced cellular tyrosine phosphorylation, even when cells were treated with 50 μM BMLOV (FIG. 26). In the experiments shown in FIG. 26, cells were treated 16 h with BMLOV and then stimulated with anti-CD3 mAb G19-4 for 5 min. Cells were then washed and resuspended in fresh media at equal concentrations of BMLOV at 37° C. Cells were then harvested and lysed at times following the initiation of CD3 stimulation as indicated. Antibody binding in immunoblots was detected by ECL. Panel A shows anti-phosphotyrosine immunoblots of whole cell lysates; Panel B shows anti-phosphotyrosine immunoblots of anti-ZAP-70 immunoprecipitates prepared from the same samples; and Panel C shows anti-ZAP-70 immunoblots of anti-ZAP-70 immunoprecipitates prepared from the same samples.

Similarly, little effect was observed on the tyrosine phosphorylation of the key T cell signaling kinase ZAP-70 or the associated ζ chain, except for a small enhancement of tyrosine phosphorylation of ZAP-70 at 20 min (FIG. 26). Taken together, these results indicate that BMLOV affects lymphocyte signaling in a lineage-specific manner, displaying disregulation of B cell antigen receptor signal pathways while T cell antigen receptor signals can be modestly enhanced.

Lineage-Specific Induction of Apoptosis by BMLOV.

Figure 27:
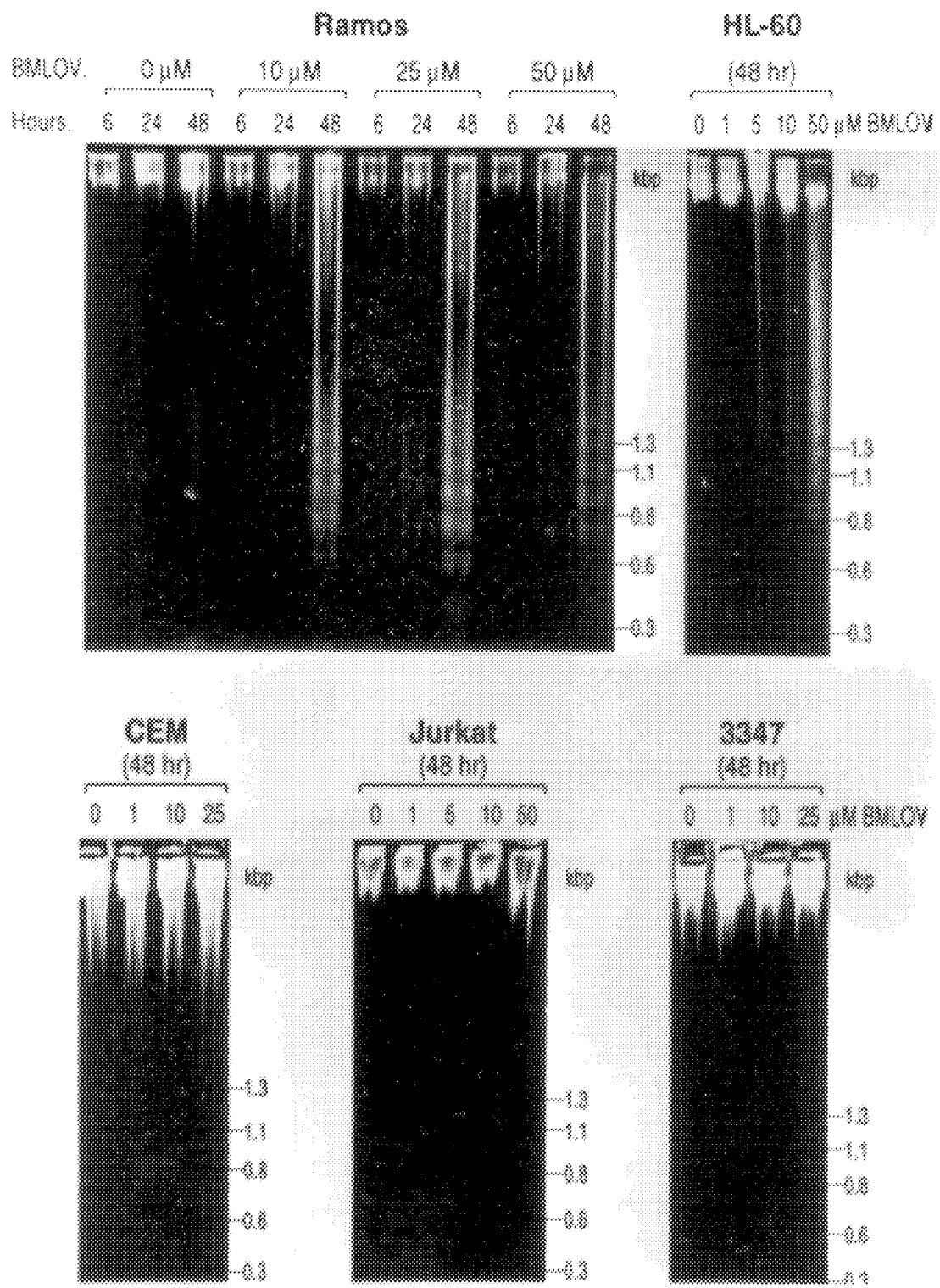
FIG. 27 shows the induction of apoptosis in B cells by BMLOV; cells were treated with BMLOV for the times and concentrations indicated; DNA was extracted and the state of DNA fragmentation was examined by agarose gel electrophoresis.

The contrasting effects of the PTP inhibitor BMLOV on T and B signaling suggested that BMLOV might have lineage specific biological effects as well. Since many immature B cells and B cell lines, including Ramos (M. A. Valentine & K. A. Licciardi, *Eur. J. Immunol.* 22:3141–3148 (1992)), respond to sIgM induced signals by undergoing activation induced programmed cell death, it was investigated whether treatment with the PTP inhibitor BMLOV that induced activation signals could also induce apoptosis. BMLOV induced extensive DNA fragmentation in Ramos B cell lymphoma cells within 48 hours at a dose of 10 μM (FIG. 27). In the experiments shown in FIG. 27, cells were treated with BMLOV for the times and concentrations indicated. DNA was extracted and the state of DNA fragmentation was examined by agarose gel electrophoresis. This pattern of DNA fragmentation is a hallmark of apoptosis in many cell types, including lymphocytes, as a result of cleavage of DNA between nucleosomes (J. J. Cohen et al., *Annu. Rev. Immunol.* 10:267–293 (1992)). Higher doses induced DNA fragmentation within 24 h of treatment. DNA fragmentation was also induced in the human acute promyelocytic leukemia cell line HL-60 in a dose dependent manner (FIG. 27). The induction of apoptosis was specific for myeloid and B cell lineages in the DNA fragmentation was not observed in the human T cell leukemia cell lines CEM or Jurkat, nor was it observed in the human colon carcinoma cell line H3347 (FIG. 27).

The extent of DNA fragmentation and the cell type selective activity was quantitated by TUNEL analysis (Y. Gavrieli et al., (1992), supra; FIG. 28). In the experiments shown in FIG. 28, cells were treated with BMLOV for 48 h and TUNEL analysis was performed by flow cytometry. TUNEL analysis was performed without TDT as a control ( . . . ), and with TdT on cells treated with 0 (-), 25 μm (- - -), or 50 μM BMLOV (- . . -). Panel A shows Ramos B cells;

Panel B shows Jurkat T cells. DNA fragmentation was extensively induced in a dose dependent manner in the majority of the Ramos B cells treated with BMLOV (FIG. 28, Panel A), confirming the observation of DNA laddering shown in FIG. 27. However, little labeling was observed in Jurkat cells treated with BMLOV (FIG. 28, Panel B), confirming that these cells are resistant to BMLOV induced DNA fragmentation. Taken together, the DNA laddering observed on agarose gel electrophoresis and the TUNEL analysis indicate that BMLOV strongly induces DNA fragmentation in B cell lines such as Ramos but not in T cells such as Jurkat.

Figure 29:
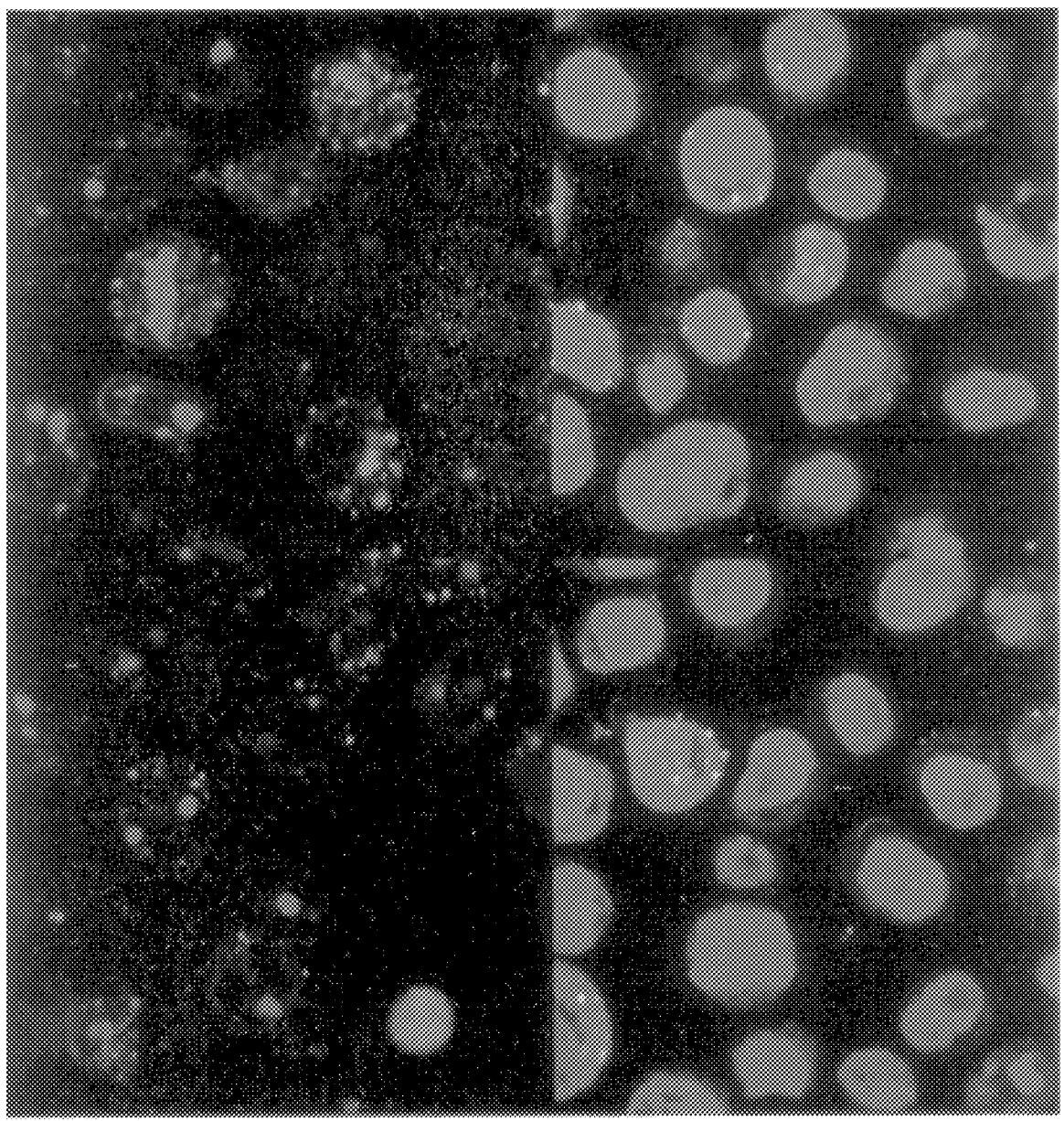
FIG. 29 shows the results of confocal laser scanning microscopy (CLSM); Ramos B cells were fixed, permeabilized and stained with propidium iodide for DNA (red) and with anti-phosphotyrosine antibodies (green); the top panels show two fields of control cells; the bottom panels show 2 fields of cells treated 48 h with 25 μm BMLOV.

In addition to DNA fragmentation, apoptotic lymphocytes display condensation of chromatin, loss of DNA and fragmentation of nuclei that can be detected by confocal laser scanning microscopy (CLSM) of propidium iodide stained cells (R. Sgonc & G. Wick, *Int. Arch. Allergy Immunol.* 105:327–332 (1994)). Therefore, CLSM was used to examine Ramos cells stained for DNA with propidium iodide and stained for phosphotyrosine (FIG. 29). In the experiments shown in FIG. 29, Ramos B cells were fixed, permeabilized and stained with propidium iodide for DNA (red) and with anti-phosphotyrosine antibodies (green) as described above. The top panels show two fields of control cells; the bottom panels show 2 fields of cells treated 48 h with 25 µm BMLOV. Control cells displayed strong staining of DNA but only low levels of phosphotyrosine. In contrast, the BMLOV treated cells showed extensive loss of DNA, condensation of chromatin, and, particularly in the lower right panel, altered nuclear morphology indicating initiation of nuclear fragmentation. These changes are all consistent with the process of programmed cell death. The cells displaying these changes simultaneously showed strong staining with anti-phosphotyrosine antibody, confirming that the PTP inhibitor BMLOV induces tyrosine phosphorylation in the cells undergoing programmed cell death. The tyrosine phosphorylation occurred in a punctate pattern at or near the cell surface as well as inside the cells.

Figure 30B:
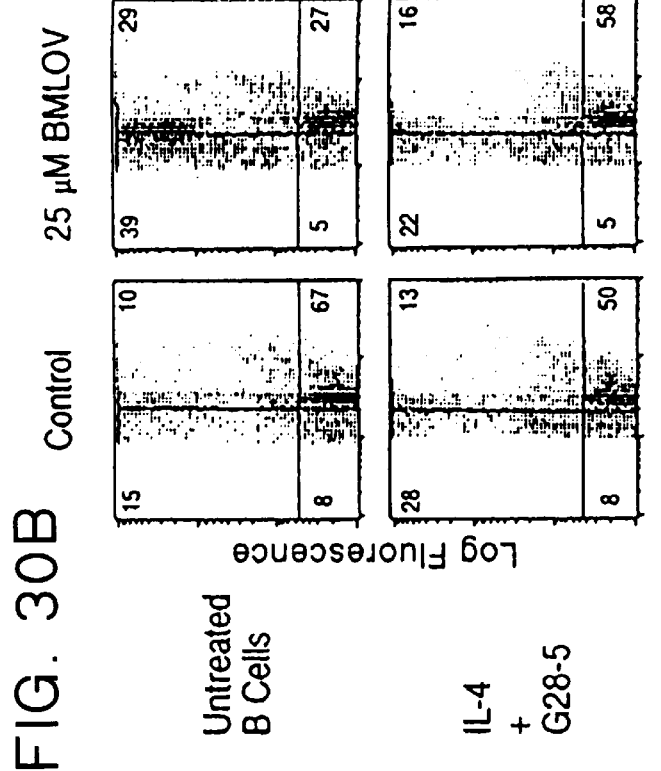
FIG. 30 shows the results of propidium iodide staining to compare the killing of Ramos B cells to normal human peripheral B cells and Jurkat T cells; cells were grown for 5 days either in the absence (control) or continuous presence of 25 μM BMLOV; viability was measured by staining with propidium iodide followed by flow cytometric analysis; the percentage of cells in each quadrant is indicated; the lower right quadrant contains the viable cells; Panel A shows a comparison of Ramos and Jurkat cells; in Panel B, normal human peripheral B cells were either untreated or treated with 1 μg/ml anti-CD40 (G28-5) plus 10 ng/ml IL-4 as indicated.
Figure 30A:
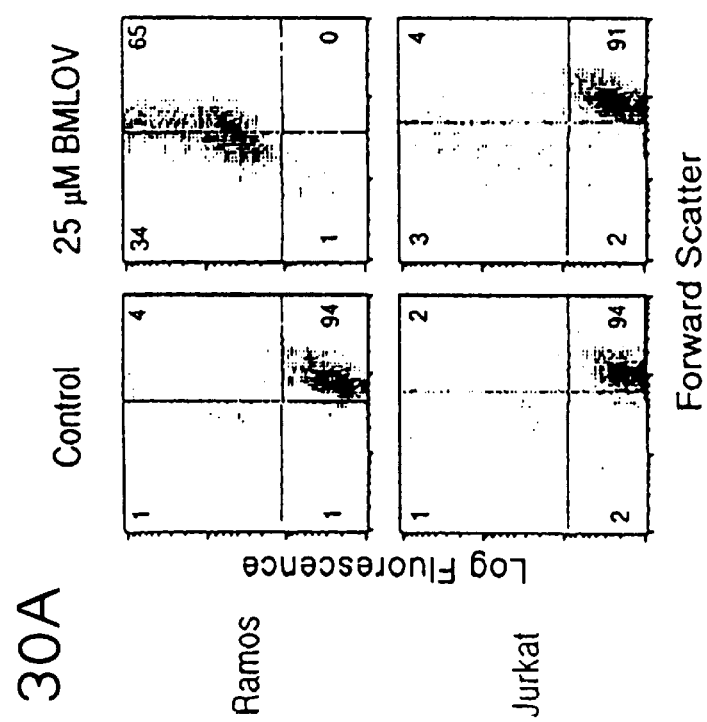

To provide a final measure of cell death, propidium iodide staining of cells was used. Normal healthy unpermeabilized cells exclude the dye, whereas cells that have completed the process of programmed cell death are stained (Y. Liu & C. A. Janeway, *J. Exp. Med.* 172:1735–1739 (1990); N. K. Damle et al., *Eur. J. Immunol.* 23:1513–1522 (1993)). This method was employed to compare the killing of Ramos B cells to normal human peripheral B cells and Jurkat T cells. In the results shown in FIG. 30, cells were grown for 5 days either in the absence (control) or continuous presence of 25 µM BMLOV. Viability was measured by staining with propidium iodide followed by flow cytometric analysis as described above. The percentage of cells in each quadrant is indicated; the lower right quadrant contains the viable cells. Panel A shows a comparison of Ramos and Jurkat cells; in Panel B, normal human peripheral B cells were either untreated or treated with 1 µg/ml anti-CD40 (G28-5) plus 10 ng/ml IL-4 as indicated. As shown in FIG. 30, Panel A, the Ramos B cells were completely killed by treatment with 25 µM BMLOV for 5 d whereas the Jurkat cells were highly resistant even to this prolonged treatment. Although data for 5 d treatment is shown here for comparison to the other cell types, Ramos cells were extensively killed by shorter times of BMLOV treatment as well. Untreated control normal human peripheral B cells showed 67% viability during 5 d of culture, but only 27% of the cells remained viable when exposed to 25 µM BMLOV. These results indicate that BMLOV can kill normal mature B cells, but these cells are somewhat less sensitive than transformed immature B cell lines. By contrast, T cells such as Jurkat, as well as normal human peripheral blood T lymphocytes (FIG. 30), are highly resistant to killing by the PTP inhibitor.

Anti-CD40 antibodies are known to protect B cells in germinal centers from undergoing apoptosis (S. Saouaf et al., (1994), supra)). Furthermore, the combination of IL-4 plus anti-CD40 has been reported to be more effective than either treatment alone in protecting B cells from apoptosis induced by hypercross-linking of surface IgM or IgD receptors (T. Furukawa et al., *Proc. Natl. Acad. Sci. USA* 91:10928–10932 (1994)). It was therefore examined whether BMLOV-induced cell death in a normal B cells could be reduced by these treatments. Treatment with anti-CD40 mAb G285 plus IL-4 protected the cells from the BMLOV-induced death, with 58% of the cells remaining viable as compared to only 27% viability for cells treated with BMLOV alone (FIG. 30). Interestingly, the viability was slightly higher than 50% viability observed in cells treated with IL-4 plus anti-CD40 alone. These results suggest that BMLOV-induced death can be blocked by appropriate biological stimulation that is known to protect against activation-induced cell death in vivo.

BMLOV increases T cell IL-2 receptor expression induced by antigen receptor stimulation.

Figure 31:
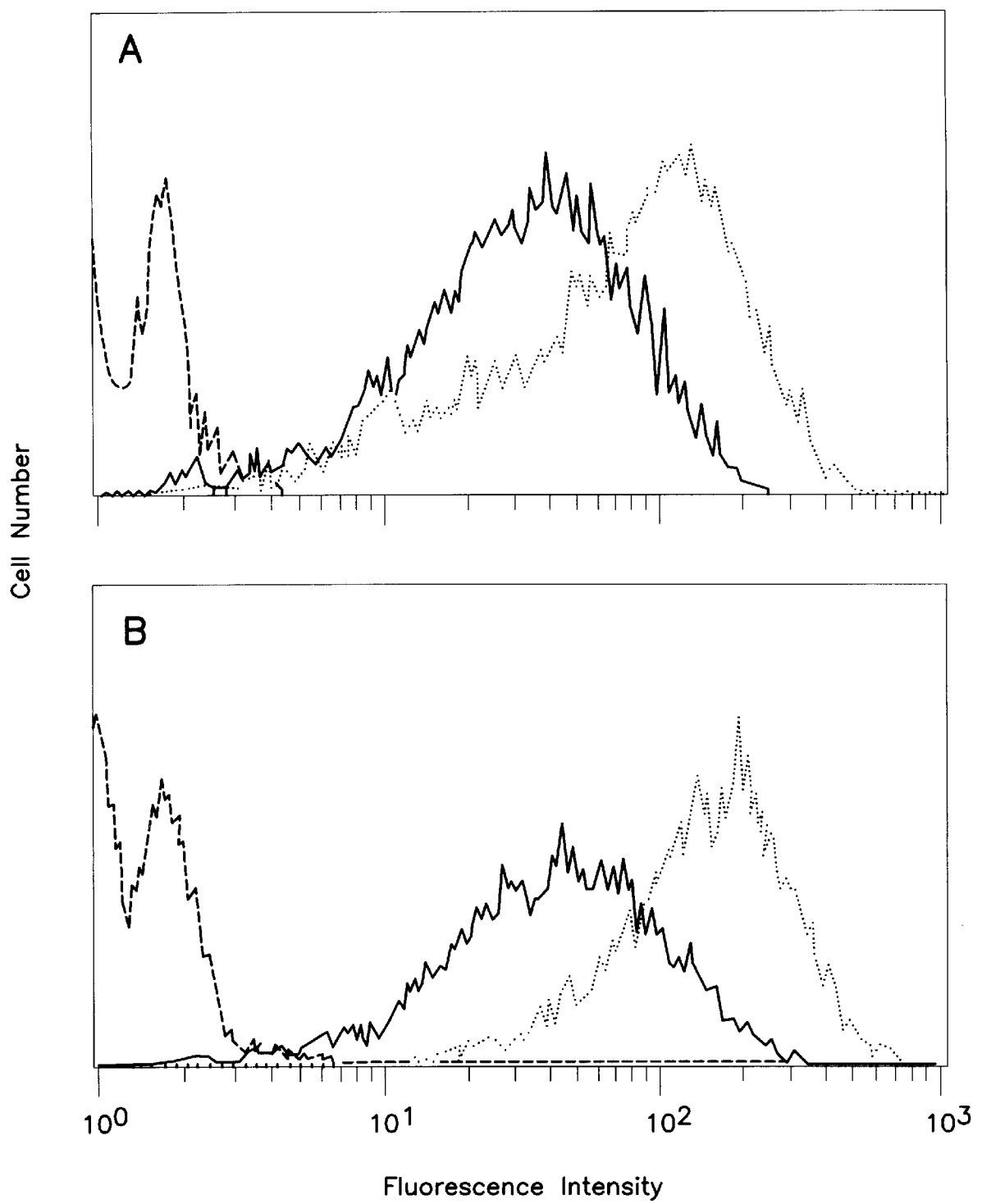
FIG. 31 shows the increase of anti-CD3 induced IL2-Rα expression by BMLOV in T cells; normal peripheral blood T cells were incubated 24 h in the presence or absence of 25 μM BMLOV in plates either precoated with 10 μg/ml anti-CD3 mAb G19-4 and then washed twice prior to addition of cells, or in uncoated plates; IL-2Rα expression was analyzed by flow cytometry after staining the cells with fluorescein-labeled anti-CD25; Cells not receiving any treatment are shown by the shaded profile, (- - -) 25 μM BMLOV only; (-) G19-4 only; ( . . . ) G 19-4 plus BMLOV; in Panel A, no IL-2 was added; in Panel B, incubations were performed with 1 ng/ml IL-2.

The expression of the IL-2 receptor a chain (IL-2Rα or CD25) is an essential biological response of T cells for productive activation following T cell receptor stimulation (K. Ullman et al., *Annu. Rev. Immunol.* 8:421–452 (1990)). In addition, the PTP inhibitor pervanadate has been reported to induce IL-2Rα expression in the absence of biological stimulation (J. J. O'Shea et al., *Proc. Natl. Acad. Sci. USA* 89:10306–10310 (1992)). Therefore, it was examined whether BMLOV could alter IL-2Rα expression alone or in combination with CD3 stimulation by solid phase anti-CD3 mAb G19-4. BMLOV alone or in combination with IL-2 did not induce IL-2Rα expression (FIG. 31). However, when used in combination with anti-CD3 stimulation, 25 µM BMLOV enhanced IL-2Rα expression, giving a 1.7-fold increase over anti-CD3 stimulation alone (FIG. 31). In the experiments shown in FIG. 31, normal peripheral blood T cells were incubated 24 h in the presence or absence of 25 µM BMLOV in plates either precoated with 10 µg/ml anti-CD3 mAb G19-4 and then washed twice prior to addition of cells, or in uncoated plates. IL-2Rα expression was analyzed by flow cytometry after staining the cells with fluorescein-labeled anti-CD25. Cells not receiving any treatment are shown by the shaded profile, (- - -) 25 µM BMLOV only; (-) G19-4 only; ( . . . ) G19-4 plus BMLOV. In Panel A, no IL-2 was added; in Panel B, incubations were performed with 1 ng/ml IL-2. The combination of anti-CD3 and IL-2 treatment gave additional IL-2Rα expression, and BMLOV treatment further enhances expression 3-fold (FIG. 31). These results indicate that the PTP inhibitor can not only increase T cell receptor-induced signals, but that it also can enhance the cells' productive biological response.

These results identify BMLOV as a PTP inhibitor with selectivity for PTP such as CD45 and PTP1B relative to serine/threonine phosphatases such as PP1 and PP2A or to alkaline phosphatase. In addition, BMLOV also appears to be active as a PTP inhibitor in cells, since it induced cellular tyrosine phosphorylation and altered antigen receptor signal transduction in a manner consistent with PTP inhibition. Most interestingly, BMLOV displayed lineage-specific effects on B versus T lymphocytes signal transduction.

The data in this example, together with the data in other examples, provide three related lines of evidence that BMLOV acted to induce signal pathways normally under control of the antigen receptor in B cells. First, BMLOV-induced cellular tyrosine phosphorylation in an overall pattern similar to that observed following sIgM cross-linking. Second, BMLOV treatment induced the activation of the Syk tyrosine kinase, which is known to be normally activated in B cells by antigen receptor stimulation (J. Hutchcroft et al., *J. Biol. Chem.* 267:8613–8619 (1992)). Third, the tyrosine phosphorylation of PLCγ2 was induced. PLCγ2 is regulated by Syk (M. Takata et al., *EMBO J.* 13:1341–1349 (1994) and is normally activated by antigen receptor stimulation in B cells (W. M. Hempel et al., *J. Immunol.* 148:3021–3027 (1992); K. M. Coggeshall et al., *Proc. Natl. Acad. Sci. USA* 89:5660–5664 (1992)). Consistent with this pathway, elevated basal $Ca^{2+}$ levels were observed.

The exact mechanism by which PTP inhibition would have these effects is not clear, particularly since normal antigen receptor signal transduction is a complex and is yet an incompletely understood process (A. Weiss & D. R. Littman, *Cell* 76:263–274 (1994)). Previous studies with phenylarsine oxide (PAO) have indicated that tyrosine phosphorylation in T cells is regulated by phosphatase activity, with the PTP counteracting constitutive levels of protein tyrosine kinase activity by dephosphorylating their substrates (P. G. Garcia-Morales et al., *Proc. Natl. Acad. Sci. USA* 87:9255–9259 (1990); M. C. Fletcher et al., *J. Biol. Chem.* 268:23697–23703 (1993)). These results support a model suggesting that inhibition of PTP activity by BMLOV leads to the accumulation of cellular tyrosine phosphorylation as a result of basal levels of tyrosine kinase activity. The increase in the amount and duration of Syk tyrosine phosphorylation observed in response to sIgM cross-linking in the presence of 10 μM BMLOV is consistent with BMLOV inhibition of PTP that normally dephosphorylate Syk. When the accumulated tyrosine phosphorylation would include direct Syk tyrosine phosphorylation, Syk would be activated, increasing the phosphorylation of its substrates such as PLCγ2.

The increase in the amount and duration of Syk tyrosine phosphorylation observed in response to sIgM cross-linking in the presence of 10 μM BMLOV is consistent with BMLOV inhibition of the PTB that normally dephosphorylate Syk. When the accumulated tyrosine phosphorylation would include direct Syk tyrosine phosphorylation, Syk would be activated, increasing the phosphorylation of its substrates such as PLCγ2. Under conditions of PTB inhibition, even moderate Syk activation could induce substantial phosphorylation. It was previously found that $H_2O_2$ activates Syk in B cells, but not following direct treatment of isolated Syk (G. L. Schieven et al., *J. Biol. Chem.* 268:16688–16692 (1993)). Hydrogen peroxide inhibits cellular PTP activity (D. Hecht & Y. Zick, *Biochem. Biophys. Res. Comm.* 188:773–779 (1992)), and this PTP inhibition may be a mechanism by which $H_2O_2$ activates Syk in B cells. Similarly, the PTP inhibitor pervanadate activates Src-family tyrosine kinases in cells (G. L. Schieven et al., *Blood* 82:1212–1220 (1993); G. A. Evans et al., *J. Biol. Chem.* 269:23407–23412 (1994)) but does not directly activate the isolated kinases (G. L. Schieven et al. (*Blood* 1993), supra). However, the possibility that BMLOV might act directly on Syk or other tyrosine kinases cannot be excluded.

While BMLOV treatment appeared to activate the B cells signal pathways, the cells' response to antigen receptor signals was inhibited. Specifically, anti-IgM mediated $Ca^{2+}$ signals were inhibited and increases in cellular tyrosine phosphorylation were impaired. These results suggest that these effects are due to an activation induced desensitization of the cells to biological signals. This unresponsiveness may be similar to the desensitization of B cells that occurs after cross-linking of a small fraction of either sIgM or sIgD receptors. Desensitized cells do not display $Ca^{2+}$ mobilization or protein kinase C translocation in response to subsequent cross-linking of the reciprocal isotype (J. Cambier et al., *Proc. Natl. Acad. Sci. USA* 85:6493–6497 (1988)). In support of this hypothesis, it was observed that BMLOV treatment of cells resulted in Syk activation and strong PLCγ2 tyrosine phosphorylation with little or no increase occurring following subsequent sIgM stimulation. In contrast to the B cells, T cells did not show basal activation but did show moderate increases in some signals, consistent with an inhibition of phosphatases that would terminate these signals. The increased IL-2 receptor expression observed following combined anti-CD3 and BMLOV treatment is consistent with the enhancement of signaling. Normal proliferation has been observed, so no long-term toxicity is apparent. This suggests that phosphotyrosine phosphatase inhibitors such as BMLOV, as well as other phosphotyrosine phosphatase inhibitors, can be used in situations in which it is desirable to amplify signals in T cells, particularly where a B cell response is not desired.

BMLOV selectively induced apoptosis in the B cells, as demonstrated by the combined results of four different experimental approaches. First, DNA ladders, a hallmark of lymphocyte apoptosis, were observed following BMLOV treatment of B cells but not T cells. Second, TUNEL analysis demonstrated that BMLOV induced apoptosis in the majority of Ramos B cells, whereas identical treatment of Jurkat T cells had little effect. Third, microscopy revealed BMLOV induced in B cells a condensation of chromatin and distortion of nuclear morphology known to occur in programmed cell death. A final measure of cell death, propidium iodide staining, demonstrated the selective killing of B versus T cells and also show that BMLOV treatment could induce the death of normal human peripheral B cells.

Previous studies have indicated that tyrosine phosphorylation plays a key role in lymphocyte apoptosis. Treatment of immature B cells lymphomas with soluble Ig antibodies often induces apoptosis (L. E. Benhamou et al., *Eur. J. Immunol.* 20:1405–1407 (1990); J. Hasbold & G. G. B. Klaus, *Eur. J. Immunol.* 20:1685–1690 (1990)), and hypercross-linking of surface IgM or IgD receptors on mature B cells also results in apoptosis (T. Furukawa et al., *Proc. Natl. Acad. Sci. USA* 91:10928–10932 (1994)). Signaling by anti-Ig antibodies requires tyrosine phosphorylation as an early and essential step (A. L. DeFranco, *Annu. Rev. Cell Biol.* 9:377–410 (1993)). Specifically, expression of the Blk tyrosine kinase has been found to be necessary for antigen receptor induced apoptosis in CH31 lymphoma cells (X. R. Yao & D. W. Scott, *Proc. Natl. Acad. Sci. USA* 90:7946–7950 (1993)). The correlation of the ability of monoclonal anti-idiotypic antibodies to induce tyrosine phosphorylation signaling and their ability to produce lymphoma regression in human patients also supports the role of tyrosine phosphorylation in these processes (W. M. J. Vuist et al., *Blood* 83:899–906 (1994)). In the case of T cells, the tyrosine kinase inhibitor herbimycin A prevented superantigen induced death that otherwise resulted from cross-linking multiple antigen receptors (N. K. Damle et al., *Eur. J. Immunol.* 23:1513–1522 (1993)). Cross-linking of Fas antigen on Jurkat T cell leukemia cells with anti-Fas antibodies induces both apoptosis and activation of tyrosine kinases leading to cellular tyrosine phosphorylation (D. L. Burg et al., *J. Biol. Chem.* 268:2304–2306 (1994)). The tyrosine kinase inhibitor herbimycin A blocked both the Fas induced tyrosine phosphorylation and death in the cells. Finally, tyrosine kinase inhibitors have been found to block tyrosine phosphorylation and apoptosis induced in B cells by ionizing radiation, while the PTP inhibitor vanadate increased these effects (F. M. Uckun et al., *Proc. Natl. Acad. Sci. USA* 89:9005–9009 (1992)).

These results suggest that BMLOV, and other analogous compounds, induce B cell apoptosis by a mechanism similar to activation induced cell death rather than by a general toxic effect. The data of this example and other examples supports this hypothesis in several ways. First, the infection of apoptosis was lineage specific and matched the specificity of tyrosine phosphorylation, whereas such specificity would not be expected for a general toxic effect. In addition to B cells, strong tyrosine phosphorylation was observed in the myeloid HL-60 cells that are killed by BMLOV. Second, the combination of IL-4 and anti-CD40 that is known to specifically rescue B cells from activation induced programmed cell death (T. Furukawa et al, (1994), supra) also rescued the cells from BMLOV induced death. Third, BMLOV activated specific pathways and molecules known to be important in B cell activation induced apoptosis. It has recently been reported that both Syk and PLCγ2 are essential for activation induced apoptosis in B cells (M. Takata et al., *J. Cell. Biochem. Suppl.* 21A:85 (1995) (abstract)) and BMLOV acted on both of these signaling molecules.

Finally, elevated intracellular $Ca^2$ is known to induce apoptosis in Ramos as well as other B cells (Z. Q. Ning & J. J. Murphy, *Eur. J. Immunol.* 23:3369–3372 (1993)), and BMLOV was found to elevate basal $Ca^{2+}$ levels. Taken together, these results suggested an important role of PTP in B cells would be to prevent apoptosis by preventing the activation of signalling molecules such as Syk and PLCγ2 in the absence of receptor activation, because this activation would tend to cause apoptosis.

The reason for the selective effects of BMLOV on B cells versus T cells or other cell types remains to be identified. The phosphatase that is regulating B cell tyrosine phosphorylation may be more sensitive to BMLOV. Alternatively, B cells might have more closely balanced levels of basal tyrosine kinase and PTP activity, making the cells more susceptible to PTP inhibition by causing the tyrosine kinase to overphosphorylate susceptible substrates. It is likely that CD45 plays an important role since immature B cells negative for CD45 are much more sensitive to apoptosis induced by anti-IgM stimulation (M. Ogimoto et al., *Intl. Immunol.* 6:647–654 (1994)). The enzyme PTP1C may also be an important target because this enzyme has been found to negatively regulate B cell antigen receptor signalling and its absence lowers the threshold for negative selection (J. G. Cyster & C. C. Goodnow, *Immunology* 2:13–24 (1995)). It is likely that multiple PTPs are involved in these effects. The expression of oncogenes and tumor suppressor genes might also be expected to influence the sensitivity of cells to PTP inhibitor induced apoptosis. HL-60 cells lack an intact p53 gene, so wild type p53 does not appear to be essential for BMLOV induced apoptosis.

These results, and the results of the other examples, suggest that BMLOV may offer several advantages relative to other PTP inhibitors such as phenylarsine oxide or pervanadate. While phenylarsine oxide is a potent inhibitor of PTPs, the high reactivity of phenylarsine oxide with protein sulfhydryl groups (S. C. Frost & M. D. Lane, *J. Biol. Chem.* 260:2646–2652 (1985)) suggests that this agent might also interfere with signaling in a manner independent of its inhibition of PTP, and the compound's high toxicity limits its biological applications (J. J. O'Shea et al., *Proc. Natl. Acad. Sci.* 89:10316–10310 (1992)). Pervanadate induces massive tyrosine phosphorylation in a wide variety of cell types due to its simultaneous strong activation of tyrosine kinases while inhibiting PTP. The strong effects on resting cells can complicate its use for the analysis of biologically induced signalling. The lineage specific effects of BMLOV on antigen receptor signalling suggest that this compound may be of value in the analysis of other receptor signal pathways. Furthermore, the lineage specific induction of apoptosis observed in this example raises the possibility that PTP inhibitors such as BMLOV, as well as other PTP inhibitors disclosed in this application, may be of value in selectively inducing programmed cell death in B cell or other malignancies.

ADVANTAGES OF THE INVENTION

The present invention provides methods for inhibiting phosphotyrosine phosphatase, particularly in B cells and T cells. This yields improved methods of inhibiting the proliferation of these cells by exploiting the occurrence of apoptosis (programmed cell death). These methods can be exploited for treatment of disorders marked by malignant proliferation of B cells or T cells, such as leukemias and lymphomas, and can be combined with other methods of treatment, including radiation. Such a combination yields synergistic effects over either radiation alone or the use of phosphotyrosine phosphatase inhibitors alone.

Methods according to the present invention can also be used for controlling proliferation of non-malignant B cells for regulation of the immune response. This is desirable for the treatment of autoimmune disease and for controlling transplant rejection, as well as for controlling class-switching in antibody-producing cells.

The methods of the present invention are further useful for studying signaling in B cells and for screening for abnormalities of B cell signaling.

In particular, the compound pV(phen) has demonstrated activity in vivo against tumors in animals that are considered to be models for the therapeutic evaluation of antitumor agents, as well as activity against tumor cell lines that are also considered to be models for the therapeutic evaluation of antitumor agents. Significantly, the activity against tumor cell lines persisted in cell sublines that exhibited resistance to other antitumor agents such as paclitaxel and topoisomerase active agents. This activity holds promise for treatment of tumors, including tumors resistant to other drugs in use. Other analogous compounds are expected to display a similar range of activities.

Additionally, the present invention encompasses methods of stimulating signaling in T cells, as well as conjugates capable of targeting modulators of phosphotyrosine metabolism to B cells. These methods and conjugates are lineage specific and are therefore useful in controlling the activity of B cells and T cells.

Although the present invention has been described with considerable detail, with reference to certain preferred versions thereof, other versions are possible. Therefore, the spirit and scope of the appended claims should not be limited to the description of the preferred versions contained herein.

I claim:

1. A conjugate comprising a modulator of phosphotyrosine metabolism covalently conjugated to a specific binding partner for a cell surface receptor found on B cells, the modulator of phosphotyrosine metabolism being selected from the group consisting of inhibitors of phosphotyrosine phosphatase and activators of tyrosine kinase.

2. The conjugate of claim 1 wherein the modulator of phosphotyrosine metabolism is an inhibitor of phosphotyrosine phosphatase.

3. A conjugate comprising an inhibitor of phosphotyrosine phosphatase covalently conjugated to a specific binding partner for a cell surface receptor found on B cells, wherein the inhibitor of phosphotyrosine phosphatase is a compound comprising a metal selected from the group consisting of vanadium (IV), copper (II) and gallium (II) coordinate-covalently bound to an organic moiety selected from the group consisting of:
(a) keto-enol tautomers with the keto and enol groups on adjacent carbon atoms that form 5-membered rings including the metal; and
(b) beta diketones in which the two keto groups are separated by one carbon atom, that form a 6-membered ring including the metal.

4. The conjugate of claim 1 wherein the metal is vanadium (IV).

5. The conjugate of claim 4 wherein the organic moiety is a keto-enol tautomer.

6. The conjugate of claim 5 wherein the organic moiety is selected from the group consisting of maltol, 2-hydroxy-2,4,6-cycloheptatrien-1-one, 3-bromo-2-hydroxy-2,4,6-cycloheptatrien-1-one, 2-hydroxy-4-isopropyl-2,4,6-cycloheptatrien-1-one, 2-hydroxy-4-methyl-2,4,6-cycloheptatrien-1-one, 3-hydroxy-1,2-dimethyl-4(1H)-pyridone, 3-ethyl-2-hydroxy-2-cyclopenten-1-one, 3,4-dihydroxy-3-cyclobuten-1,2-dione, ethyl 2-hydroxy-4-oxo-2-pentenone, 2,3,5,6-tetrahydroxy-1,4-benzoquinone, 2',4'-dihydroxy-2-methoxyacetophenone, 4-hydroxy-5-methyl-4-cyclopenten-1,3-dione, 2-chloro-3-hydroxy-1,4-naphthoquinone, 2-(4-bromophenyl)-3-hydroxymaleimide, 2-hydroxy-3-methyl-2-cyclopenten-1-one, 2',3',4'-trihydroxyacetophenone, furoin, 2-hydroxy-2-methylpropiophenone, maclurin, 6-(pyrrolidinomethyl) kojic acid, alpha-acetyl-4-hydroxy-beta-(hydroxymethyl)-3-methoxycinnamic acid gamma-lactone, 4-hydroxy-5-phenyl-4-cyclopenten-1,3-dione, 6-(morpholinomethyl) kojic acid, 1-(4,5-dimethoxy-2-hydroxyphenyl)-3-methyl-2-buten-1-one, purpurogallin, 2,3-dihydroxy-1,4-phenazinedione, alizarin orange, 1-hydroxy-1-methylnaphthalen-2(1H)-one, alizarin, 6-(piperidinomethyl) kojic acid, 1,2,7-trihydroxyanthraquinone, 6-(4-methylpiperazinomethyl) kojic acid, fisetin, 3-oxo-4,5,6-trihydroxy-3(H)-xanthene-9-propionic acid, benzoin, 4'-chlorobenzoin, quercetin, morin, myricetin, and 4,4'-dimethylbenzoin.

7. The conjugate of claim 6 wherein the organic moiety is maltol.

8. The conjugate of claim 4 wherein the organic moiety is a beta diketone.

9. The conjugate of claim 8 wherein the organic moiety is selected from the group consisting of acetylacetone, 2-acetyl-1-tetralone, benzoylacetone, 1-benzoylacetylacetone, 1,1,1-trifluoro-2,4-pentanedione, S-methyl-4,4,4-trifluoro-3-oxothiobutyrate, 2-acetyl-1,3-cyclopentanedione, 3-chloro-2,4-pentanedione, 1,1,1,5,5,5-hexafluoro-2,4-pentanedione, 3-ureidomethylene-2,4-pentanedione, 2-acetylcyclopentanone, 2-acetylcyclohexanone, 3-methyl-2,4-pentanedione, 2,4,6-heptatrione, 3-ethyl-2,4-pentanedione, thianoyltrifluoroacetone, S-t-butyl-acetothioacetate, 3-acetyl-5-methylhexan-2-one, 3-acetyl-2-heptanone, 2,2-dimethyl-6,6,7,7,8,8,8-heptafluoro-3,5-octanedione, 4-hydroxy-5-phenyl-4-cyclopenten-1,3-dione, 4,4,4-trifluoro-1-phenyl-1,3-butanedione, 3-acetyl-2-octanone, 1(2-hydroxy-4-methylphenyl)-1,3-butanedione, 1-(2-hydroxy-5-methylphenyl)-1,3-butanedione, 3-benzylidene-2,4-pentanedione, 1-(2-hydroxy-5-methylphenyl)-1,3-pentanedione, 2,2,6,6-tetramethyl-3,5-heptanedione, 3-acetyl-5-hydroxy-2-methylchromone, (+)-3-(trifluoroacetyl)camphor, 4,9-dihydro-6-methyl-5H-furo(3,2-g) (1) benzopyran-4,5,9-trione, 3-(2-nitrobenzylidene)-2,4-pentanedione, 1,3-bis-(4-chlorophenyl)-1,3-propanedione, 1,3-bis-(4-fluorophenyl)-1,3-propanedione, 4,4,4-trifluoro-1-(2-naphthyl)-1,3-butanedione, 1-(2-hydroxyphenyl)-3-(4-methoxyphenyl)-1,3-propanedione, 2-bromo-1,3-diphenyl-1,3-propanedione, dibenzoylmethane, 2-(4-chlorobenzylidene)-1-phenyl-1,3-butanedione, 2-(2-nitrobenzylidene)-1-phenyl-1,3-butanedione, bis(4-methoxybenzoyl) methane, and curcumin.

10. The conjugate of claim 9 wherein the organic moiety is 2-acetyl 1-tetralone.

11. A conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex including:
(a) a vanadium (V) metal ion;
(b) an oxo group coordinate-covalently bound to the metal ion;
(c) two peroxo groups coordinate-covalently bound to the metal ion; and
(d) at least one organic moiety coordinate-covalently bound to the metal ion through at least one N-containing or O-containing functional group capable of donating electrons through a coordinate-covalent bond, the coordinate-covalent complex having an affinity for the active site of a phosphotyrosine phosphatase sufficient to detectably inhibit the activity of one or more phosphotyrosine phosphatases, the specific binding partner for the cell surface receptor being selected from the group consisting of a monoclonal antibody for one of CD19, CD10, CD20, CD21, CD22, CD24, CD37, CD40, CDw75, CDw78, and B7, wherein the coordinate-covalent complex is selected from the group consisting of (1,10-phenanthroline) (oxodiperoxovanadium(V), oxalato-oxodiperoxovanadium(V), (2,2'-bipyridine) oxodiperoxovanadium(V), (4,7-dimethyl-1,10-phenanthroline) oxodiperoxovanadium(V), (3,4,7,8-tetramethyl-1,10-phenanthroline) oxodiperoxovanadium(V), (pyridine-2-carboxylic acid) oxodiperoxovanadium(V), (5-hydroxypyridine-2-carboxylic acid) oxodiperoxovanadium(V), (pyridine-2,6-dicarboxylic acid) oxodiperoxovanadium (V), and derivatives thereof possessing substantially equivalent affinity for the active site of phosphotyrosine phosphatase.

12. The conjugate of claim 11 wherein the coordinate-covalent complex is (1,10-phenanthroline) oxodiperoxovanadium (V).

13. A conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex including:
(a) a vanadium(V) metal ion;
(b) an oxo group coordinate-covalently bound to the metal ion;
(c) one peroxo group coordinate-covalently bound to the metal ion; and (d) at least one organic moiety coordinate-covalently bound to the metal ion through at least one N-containing or O-containing functional group capable of donating electrons through a coordinate-covalent bond, the coordinate-covalent complex having an affinity for the active site of a phosphotyrosine phosphatase sufficient to detectably inhibit the activity of one or more phosphotyrosine phosphatases, the specific binding partner for the cell surface receptor being selected from the group consisting of a monoclonal antibody for one of CD19, CD10, CD20, CD21, CD22, CD24, CD37, CD40, CDw75, CDw78, and B87, wherein the coordinate-covalent complex is (pyridine-2,6-dicarboxylato) (hydrato) oxoperoxovanadium(V).

14. A conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex including:

(a) a molybdenum (VI) metal ion;

(b) an oxo group coordinate-covalently bound to the metal ion;

(c) two peroxo groups coordinate-covalently bound to the metal ion; and (d) at least one organic moiety coordinate-covalently bound to the metal ion through at least one N-containing or O-containing functional group capable of donating electrons through a coordinate-covalent bond, the coordinate-covalent complex having an affinity for the active site of a phosphotyrosine phosphatase sufficient to detectably inhibit the activity of one or more phosphotyrosine phosphatases, the specific binding partner for the cell surface receptor being selected from the group consisting of a monoclonal antibody for one of CD19, CD10, CD20, CD21, CD22, CD24, CD37, CD40, CDw75, CDw78, and B7, wherein the coordinate-covalent complex is selected from the group consisting of bis(dimethylformamido) oxodiperoxomolybdenum(VI) and hydrogen (pyridine-2 carboxylato) oxodiperoxomolybdenum (VI) hydrate.

15. The conjugate of claim 1 wherein the specific binding partner for the cell surface receptor found on B cells is selected from the group consisting of a monoclonal antibody for one of CD19, CD10, CD20, CD21, CD22, CD24, CD37, CD40, CDw75, CDw78, and B7.

16. The conjugate of claim 15 wherein the specific binding partner for the cell surface receptor found on B cells is anti-CD19 monoclonal antibody.

17. A method for inhibiting proliferation of B cells comprising the step of contacting proliferating B cells with the conjugate of claim 1.

18. A method for inhibiting proliferation of B cells comprising the step of contacting proliferating B cells with the conjugate of claim 3.

19. A conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex selected from the group consisting of: (1,10-phenanthroline) oxodiperoxovanadium (IV), oxalatooxodiperoxovanadium (V), (2,2'-bipyridine) oxodiperoxovanadium (V), (4,7-dimethyl-1,10-phenanthroline) oxodiperoxovanadium (V), (3,4,7,8-tetramethyl-1,10-phenanthroline) oxodiperoxovanadium (V), (pyridine-2-carboxylic acid) oxodiperoxovanadium (V), (5-hydroxypyridine-2-carboxylic acid) oxodiperoxovanadium (V), (pyridine-2,6-dicarboxylic acid) oxodiperoxovanadium (V), (pyridine-2,6-dicarboxylato) (hydrato) oxoperoxovanadium (V), bis (dimethylformamido) oxodiperoxomolybdenum (VI), hydrogen (pyridine-2-carboxylato) oxodiperoxomolybdenum (VI) hydrate, [(N-salicylidene)-2-hydroxybenzeneamine] [ethanol] oxoperoxomolybdenum (VI), (pyridine-2–6-dicarboxylato) oxoperoxomolybdenum (VI), bis (N-phenylbenzohydroxamato) oxodiperoxomolybdenum (VI), (bis) (benzene-1,2-di[dimethylarsino]) [chloro] oxomolybdenum (VI), meso-tartrato oxovanadium (V), oxalato-oxodiperoxomolybdenum (VI), (1,10-phenanthroline) oxodiperoxotungsten (VI), (pyridine-2-carboxylic acid) oxodiperoxotungsten (VI), and derivatives thereof substituted with hydroxy or lower alkyl substituents that do not interfere with the formation of coordinate-covalent bonds, the coordinate-covalent complex having an affinity for the active site of a phosphotyrosine phosphatase sufficient to detectably inhibit the activity of one or more phosphotyrosine phosphatases.

20. The conjugate of claim 19 wherein the specific binding partner for the cell surface receptor found on B cells is selected from the group consisting of a monoclonal antibody from one of CD19, CD10, CD20, CD21, CD 22, CD24, CD37, CD40, CDw75, CDw78, and B7.

21. The conjugate of claim 20 wherein the specific binding partner for the cell surface receptor found on B cells is anti-CD19 monoclonal antibody.

22. A conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex including:

(a) a molybdenum(VI) metal ion;

(b) an oxo group coordinate-covalently bound to the metal ion;

(c) one peroxo group coordinate-covalently bound to the metal ion; and (d) at least one organic moiety coordinate-covalently bound to the metal ion through at least one N-containing or O-containing functional group capable of donating electrons through a coordinate-covalent bond, the coordinate-covalent complex having an affinity for the active site of a phosphotyrosine phosphatase sufficient to detectably inhibit the activity of one or more phosphotyrosine phosphatases, the specific binding partner for the cell surface receptor being selected from the group consisting of a monoclonal antibody for one of CD19, CD10, CD20, CD21, CD22, CD24, CD37, CD40, CDw75, CDw78, and B7, wherein the coordinate-covalent complex is selected from the group consisting of [(N-salicylidene)-2-hydroxybenzeneamine][ethanol] oxoperoxymolybdenum(VI), (pyridine-2,6-dicarboxylato)(hydrato)(oxoperoxomolybdenum(VI)), and bis(N-phenylbenzohydroxamato) oxoperoxomolybdenum(VI).

23. A conjugate comprising an inhibitor of phosphotyrosine phosphatase conjugated to a specific binding partner for a cell surface receptor found on B cells, wherein the inhibitor of phosphotyrosine phosphatase comprises a coordinate-covalent complex including:

(a) a molybdenum(VI) metal ion;

(b) an oxo group coordinate-covalently bound to the metal ion; and (c) at least one organic moiety coordinate-covalently bound to the metal ion through at least one N-containing or O-containing moiety capable of donating electrons to a coordinate-covalent bond, the coordinate-covalent complex having an affinity for an active site of a phosphotyrosine phosphatase sufficient to detectably inhibit the activity of one or more phosphotyrosine phosphatases, the specific binding partner for the cell surface receptor being selected from the group consisting of a monoclonal antibody for one of CD19, CD10, CD20, CD21, CD22, CD24, CD37, CD40, CDw75, CDw78, and B7, wherein the coordinate-covalent complex is bis[benzene-1,2-di(dimethylarsino)][chloro]oxomolybdenum(VI).

24. A conjugate comprising an inhibitor of phosphotyrosine phosphatase conjugated to a specific binding partner for a cell surface receptor found on B cells, wherein the inhibitor of phosphotyrosine phosphatase comprises a coordinate-covalent complex including:

(a) a vanadium(V) metal ion;

(b) an oxo group coordinate-covalently bound to the metal ion; and (c) at least one organic moiety coordinate-covalently bound to the metal ion through at least one N-containing or O-containing moiety capable of donating electrons to a coordinate-covalent bond, the coordinate-covalent complex having an affinity for an active site of a phosphotyrosine phosphatase sufficient to detectably inhibit the activity of one or more phosphotyrosine phosphatases, the specific binding partner being selected from the group consisting of a monoclonal antibody from one of CD19, CD10, CD20, CD21, CD22, CD24, CD37, CD40, CDw75, CDw78, and B7, wherein the coordinate-covalent complex is meso-tartrato oxovanadium(V).

25. A method for inhibiting proliferation of B cells comprising the step of contacting proliferating B cells with a conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex selected from the group consisting of (1,10-phenanthroline)oxodiperoxovanadium (V), oxalato-oxodiperoxovanadium (V), (2,2'-bipyridine)oxodiperoxovanadium (V), (4,7-dimethyl-1,10-phenanthroline)oxodiperoxovanadium (V), (3,4,7,8-tetramethyl-1,10-phenanthroline)oxodiperoxovanadium (V), (pyridine-2-carboxylic acid)oxodiperoxovanadium (V), (5-hydroxypyridine-2-carboxylic acid) oxodiperoxovanadium (V), (pyridine 2,6-dicarboxylic acid) oxodiperoxovanadium (V), (pyridine-2,6-dicarboxylato)(hydrato)oxoperoxovanadium(V), bis(dimethylformamido) oxodiperoxomolybdenum(VI), hydrogen (pyridine-2-carboxylato) oxodiperoxomolybdenum (VI) hydrate, [(N-salicylidene)-2-hydroxybenzeneamine] [ethanol] oxoperoxomolybdenum (VI), (pyridine-2,6-dicarboxylato) (hydrato) oxoperoxomolybdenum (VI), bis(N-phenylbenzohydroxamato) oxoperoxomolybdenum (VI), and derivatives thereof possessing substantially equivalent affinity for the active site of phosphotyrosine phosphatase, the coordinate-covalent complex having an affinity for an active site of a phosphotyrosine phosphatase sufficient to detectably inhibit the activity of one or more phosphotyrosine phosphatases, and wherein the specific binding partner for the cell surface receptor found on B cells is selected from the group consisting of a monoclonal antibody for one of CD19, CD10, CD20, CD21, CD22, CD24, CD37, CD40, CDw75, CDw78, and B7.

26. A method for inhibiting proliferation of B cells comprising the step of contacting proliferating B cells with a conjugate comprising an inhibitor of phosphotyrosine phosphatase covalently conjugated to a specific binding partner for a cell surface receptor found on B cells, wherein the inhibitor of phosphotyrosine phosphatase comprises a coordinate-covalent complex selected from the group consisting of bis[benzene-1,2-di(dimethylarsino)] [chloro] oxomolybdenum (VI), and meso-tartrato oxovanadium (V), the coordinate-covalent complex having an affinity for an active site of a phosphotyrosine phosphatase sufficient to detectably inhibit the activity of one or more phosphotyrosine phosphatases, and wherein the specific binding partner for the cell surface receptor found on B cells is selected from the group consisting of a monoclonal antibody for one of CD19. CD10, CD20, CD21, CD22, CD24, CD37, CD40, CDw75, CDw78, and B7.

* * * * *